United States Patent
Rogers et al.

(10) Patent No.: US 9,554,484 B2
(45) Date of Patent: Jan. 24, 2017

(54) APPENDAGE MOUNTABLE ELECTRONIC DEVICES CONFORMABLE TO SURFACES

(71) Applicant: The Board of Trustees of the University of Illinois, Urbana, IL (US)

(72) Inventors: John A Rogers, Champaign, IL (US); Ming Ying, Urbana, IL (US); Andrew Bonifas, Urbana, IL (US); Nanshu Lu, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 972 days.

(21) Appl. No.: 13/853,770

(22) Filed: Mar. 29, 2013

(65) Prior Publication Data

US 2013/0333094 A1    Dec. 19, 2013

Related U.S. Application Data

(60) Provisional application No. 61/794,004, filed on Mar. 15, 2013, provisional application No. 61/636,527, (Continued)

(51) Int. Cl.
*H05K 1/00* (2006.01)
*H05K 7/02* (2006.01)
(Continued)

(52) U.S. Cl.
CPC ............. *H05K 7/02* (2013.01); *A41D 19/015* (2013.01); *A61B 5/1125* (2013.01); *A61B 5/483* (2013.01);
(Continued)

(58) Field of Classification Search
USPC ................................. 361/749, 748, 679.01
See application file for complete search history.

(56) References Cited

U.S. PATENT DOCUMENTS 3,949,410 A    4/1976  Bassous
4,058,418 A    11/1977 Lindmayer
(Continued)

FOREIGN PATENT DOCUMENTS

CN    1222758    7/1999
CN    1454045    11/2003
(Continued)

OTHER PUBLICATIONS

Supplementary European Search Report corresponding to European Patent Application No. EP13769707, dated Oct. 15, 2015.
(Continued)

*Primary Examiner* — Andargie M Aychillhum
(74) *Attorney, Agent, or Firm* — Lathrop & Gage LLP

(57) ABSTRACT

Disclosed are appendage mountable electronic systems and related methods for covering and conforming to an appendage surface. A flexible or stretchable substrate has an inner surface for receiving an appendage, including an appendage having a curved surface, and an opposed outer surface that is accessible to external surfaces. A stretchable or flexible electronic device is supported by the substrate inner and/or outer surface, depending on the application of interest. The electronic device in combination with the substrate provides a net bending stiffness to facilitate conformal contact between the inner surface and a surface of the appendage provided within the enclosure. In an aspect, the system is capable of surface flipping without adversely impacting electronic device functionality, such as electronic devices comprising arrays of sensors, actuators, or both sensors and actuators.

34 Claims, 20 Drawing Sheets

Related U.S. Application Data filed on Apr. 20, 2012, provisional application No. 61/618,371, filed on Mar. 30, 2012.

(51) Int. Cl.
| | | |
|---|---|---|
| *A61B 5/00* | (2006.01) | |
| *A41D 19/015* | (2006.01) | |
| *H05K 3/00* | (2006.01) | |
| *A61B 5/11* | (2006.01) | |
| *H01L 23/538* | (2006.01) | |
| *A61B 5/01* | (2006.01) | |
| *H05K 1/02* | (2006.01) | |

(52) U.S. Cl.
CPC .......... *A61B 5/6806* (2013.01); *A61B 5/6826* (2013.01); *A61B 5/6843* (2013.01); *A61B 5/7455* (2013.01); *A61B 34/35* (2016.02); *A61B 34/76* (2016.02); *H01L 23/5388* (2013.01); *H05K 3/0014* (2013.01); *A61B 5/01* (2013.01); *A61B 5/4875* (2013.01); *A61B 2034/741* (2016.02); *A61B 2505/05* (2013.01); *A61B 2562/028* (2013.01); *A61B 2562/0209* (2013.01); *A61B 2562/029* (2013.01); *A61B 2562/0233* (2013.01); *A61B 2562/0247* (2013.01); *A61B 2562/0261* (2013.01); *A61B 2562/0271* (2013.01); *A61B 2562/0285* (2013.01); *A61B 2562/046* (2013.01); *A61B 2562/12* (2013.01); *A61B 2562/164* (2013.01); *A61B 2562/227* (2013.01); *H01L 2224/95* (2013.01); *H01L 2924/0002* (2013.01); *H05K 1/0283* (2013.01); *Y10T 29/49124* (2015.01)

(56) References Cited

U.S. PATENT DOCUMENTS

| | | |
|---|---|---|
| 4,392,451 A | 7/1983 | Mickelsen et al. |
| 4,471,003 A | 9/1984 | Cann |
| 4,487,162 A | 12/1984 | Cann |
| 4,663,828 A | 5/1987 | Hanak |
| 4,761,335 A | 8/1988 | Aurichio et al. |
| 4,766,670 A | 8/1988 | Gazdik et al. |
| 4,784,720 A | 11/1988 | Douglas |
| 4,855,017 A | 8/1989 | Douglas |
| 5,041,973 A | 8/1991 | Lebron et al. |
| 5,086,785 A | 2/1992 | Gentile et al. |
| 5,118,400 A | 6/1992 | Wollam |
| 5,178,957 A | 1/1993 | Kolpe et al. |
| 5,204,144 A | 4/1993 | Cann et al. |
| 5,313,094 A | 5/1994 | Beyer et al. |
| 5,316,017 A | 5/1994 | Edwards et al. |
| 5,339,180 A | 8/1994 | Katoh |
| 5,403,700 A | 4/1995 | Heller et al. |
| 5,427,096 A | 6/1995 | Bogusiewicz et al. |
| 5,434,751 A | 7/1995 | Cole, Jr. et al. |
| 5,455,178 A | 10/1995 | Fattnger |
| 5,469,845 A | 11/1995 | Delonzor et al. |
| 5,501,893 A | 3/1996 | Laermer et al. |
| 5,525,815 A | 6/1996 | Einset |
| 5,545,291 A | 8/1996 | Smith et al. |
| 5,625,471 A | 4/1997 | Smith |
| 5,648,148 A | 7/1997 | Simpson |
| 5,678,737 A | 10/1997 | White |
| 5,687,737 A | 11/1997 | Branham et al. |
| 5,691,245 A | 11/1997 | Bakhit |
| 5,753,529 A | 5/1998 | Chang et al. |
| 5,757,081 A | 5/1998 | Chang et al. |
| 5,767,578 A | 6/1998 | Chang et al. |
| 5,772,905 A | 6/1998 | Chou |
| 5,783,856 A | 7/1998 | Smith et al. |
| 5,790,151 A | 8/1998 | Mills |
| 5,817,242 A | 10/1998 | Biebuyck et al. |
| 5,824,186 A | 10/1998 | Smith et al. |
| 5,904,545 A | 5/1999 | Smith et al. |
| 5,907,189 A | 5/1999 | Mertol |
| 5,915,180 A | 6/1999 | Hara et al. |
| 5,917,534 A | 6/1999 | Rajeswaran |
| 5,928,001 A | 7/1999 | Gilette et al. |
| 5,955,781 A | 9/1999 | Joshi et al. |
| 5,976,683 A | 11/1999 | Liehrr et al. |
| 5,998,291 A | 12/1999 | Bakhit et al. |
| 6,024,702 A | 2/2000 | Iverson |
| 6,057,212 A | 5/2000 | Chan et al. |
| 6,080,608 A | 6/2000 | Nowak |
| 6,097,984 A | 8/2000 | Douglas |
| 6,165,391 A | 12/2000 | Vedamuttu |
| 6,171,730 B1 | 1/2001 | Kuroda et al. |
| 6,225,149 B1 | 5/2001 | Gan et al. |
| 6,236,883 B1 | 5/2001 | Ciaccio et al. |
| 6,265,326 B1 | 7/2001 | Ueno |
| 6,274,508 B1 | 8/2001 | Jacobsen et al. |
| 6,276,775 B1 | 8/2001 | Schulte |
| 6,277,712 B1 | 8/2001 | Kang et al. |
| 6,281,038 B1 | 8/2001 | Jacobsen et al. |
| 6,284,418 B1 | 9/2001 | Trantolo |
| 6,291,896 B1 | 9/2001 | Smith |
| 6,316,278 B1 | 11/2001 | Jacobsen et al. |
| 6,316,283 B1 | 11/2001 | Saurer |
| 6,317,175 B1 | 11/2001 | Salerno et al. |
| 6,322,895 B1 | 11/2001 | Canham |
| 6,334,960 B1 | 1/2002 | Wilson et al. |
| 6,380,729 B1 | 4/2002 | Smith |
| 6,403,397 B1 | 6/2002 | Katz |
| 6,413,790 B1 | 7/2002 | Duthaler et al. |
| 6,417,025 B1 | 7/2002 | Gengel |
| 6,420,266 B1 | 7/2002 | Smith et al. |
| 6,433,401 B1 | 8/2002 | Clark et al. |
| 6,451,191 B1 | 9/2002 | Bentsen et al. |
| 6,459,418 B1 | 10/2002 | Comiskey et al. |
| 6,468,638 B2 | 10/2002 | Jacobsen et al. |
| 6,479,395 B1 | 11/2002 | Smith et al. |
| 6,487,906 B1 | 12/2002 | Hock |
| 6,517,995 B1 | 2/2003 | Jacobson et al. |
| 6,527,964 B1 | 3/2003 | Smith et al. |
| 6,555,408 B1 | 4/2003 | Jacobsen et al. |
| 6,559,905 B1 | 5/2003 | Akiyama |
| 6,566,744 B2 | 5/2003 | Gengel |
| 6,580,151 B2 | 6/2003 | Vandeputte et al. |
| 6,586,338 B2 | 7/2003 | Smith et al. |
| 6,590,346 B1 | 7/2003 | Hadley et al. |
| 6,606,079 B1 | 8/2003 | Smith |
| 6,606,247 B2 | 8/2003 | Credelle et al. |
| 6,608,370 B1 | 8/2003 | Chen et al. |
| 6,623,579 B1 | 9/2003 | Smith et al. |
| 6,639,578 B1 | 10/2003 | Comiskey et al. |
| 6,655,286 B2 | 12/2003 | Rogers |
| 6,657,289 B1 | 12/2003 | Craig et al. |
| 6,661,037 B2 | 12/2003 | Pan et al. |
| 6,665,044 B1 | 12/2003 | Jacobsen et al. |
| 6,666,821 B2 | 12/2003 | Keimel |
| 6,683,663 B1 | 1/2004 | Hadley et al. |
| 6,693,384 B1 | 2/2004 | Vicentini et al. |
| 6,706,402 B2 | 3/2004 | Rueckes et al. |
| 6,720,469 B1 | 4/2004 | Curtis et al. |
| 6,723,576 B2 | 4/2004 | Nozawa et al. |
| 6,730,990 B2 | 5/2004 | Kondo et al. |
| 6,731,353 B1 | 5/2004 | Credelle et al. |
| 6,743,982 B2 | 6/2004 | Biegelsen et al. |
| 6,780,696 B1 | 8/2004 | Schatz |
| 6,784,450 B2 | 8/2004 | Pan et al. |
| 6,814,898 B1 | 11/2004 | Deeman et al. |
| 6,816,380 B2 | 11/2004 | Credelle et al. |
| 6,844,673 B1 | 1/2005 | Bernkopf |
| 6,848,162 B2 | 2/2005 | Arneson et al. |
| 6,850,312 B2 | 2/2005 | Jacobsen et al. |
| 6,856,830 B2 | 2/2005 | He |
| 6,863,219 B1 | 3/2005 | Jacobsen et al. |
| 6,864,435 B2 | 3/2005 | Hermanns et al. |
| 6,864,570 B2 | 3/2005 | Smith |
| 6,872,645 B2 | 3/2005 | Duan et al. |
| 6,878,871 B2 | 4/2005 | Scher et al. |
| 6,881,979 B2 | 4/2005 | Starikov et al. |

(56) References Cited

U.S. PATENT DOCUMENTS

| | | |
|---|---|---|
| 6,887,450 B2 | 5/2005 | Chen et al. |
| 6,900,094 B2 | 5/2005 | Hammond et al. |
| 6,917,061 B2 | 7/2005 | Pan et al. |
| 6,936,181 B2 | 8/2005 | Bulthaup et al. |
| 6,949,199 B1 | 9/2005 | Gauzner et al. |
| 6,949,206 B2 | 9/2005 | Whiteford |
| 6,950,220 B2 | 9/2005 | Abramson et al. |
| 6,984,934 B2 | 1/2006 | Moller et al. |
| 6,989,285 B2 | 1/2006 | Ball |
| 7,029,951 B2 | 4/2006 | Chen et al. |
| 7,033,961 B1 | 4/2006 | Smart et al. |
| 7,067,903 B2 | 6/2006 | Tachibana et al. |
| 7,116,318 B2 | 10/2006 | Amundson et al. |
| 7,132,313 B2 | 11/2006 | O'Connor et al. |
| 7,148,512 B2 | 12/2006 | Leu et al. |
| 7,158,277 B2 | 1/2007 | Berggren et al. |
| 7,169,546 B2 | 1/2007 | Suzuki et al. |
| 7,169,669 B2 | 1/2007 | Blakers et al. |
| 7,170,164 B2 | 1/2007 | Chen et al. |
| 7,186,624 B2 | 3/2007 | Welser et al. |
| 7,190,051 B2 | 3/2007 | Mech et al. |
| 7,195,733 B2 | 3/2007 | Rogers et al. |
| 7,223,609 B2 | 5/2007 | Anvar et al. |
| 7,253,442 B2 | 8/2007 | Huang et al. |
| 7,255,919 B2 | 8/2007 | Sakata et al. |
| 7,291,540 B2 | 11/2007 | Mech et al. |
| 7,374,968 B2 | 5/2008 | Kornlivich et al. |
| 7,425,523 B2 | 9/2008 | Ikemizu et al. |
| 7,521,292 B2 | 4/2009 | Rogers et al. |
| 7,557,367 B2 | 7/2009 | Rogers et al. |
| 7,622,367 B1 | 11/2009 | Nuzzo et al. |
| 7,629,691 B2 | 12/2009 | Roush et al. |
| 7,635,755 B2 | 12/2009 | Kaplan et al. |
| 7,674,882 B2 | 3/2010 | Kaplan et al. |
| 7,700,402 B2 | 4/2010 | Wild et al. |
| 7,704,684 B2 | 4/2010 | Rogers et al. |
| 7,705,280 B2 | 4/2010 | Nuzzo et al. |
| 7,709,961 B2 | 5/2010 | Greenberg et al. |
| 7,727,575 B2 | 6/2010 | Kaplan et al. |
| 7,799,699 B2 | 9/2010 | Nuzzo et al. |
| 7,842,780 B2 | 11/2010 | Kaplan et al. |
| 7,896,807 B2 | 3/2011 | Clancy et al. |
| 7,932,123 B2 | 4/2011 | Rogers et al. |
| 7,943,491 B2 | 5/2011 | Nuzzo et al. |
| 7,972,875 B2 | 7/2011 | Rogers et al. |
| 7,982,296 B2 | 7/2011 | Nuzzo et al. |
| 8,039,847 B2 | 10/2011 | Nuzzo et al. |
| 8,198,621 B2 | 6/2012 | Rogers et al. |
| 8,217,381 B2 | 7/2012 | Rogers et al. |
| 8,367,035 B2 | 2/2013 | Rogers et al. |
| 8,394,706 B2 | 3/2013 | Nuzzo et al. |
| 8,440,546 B2 | 5/2013 | Rogers et al. |
| 8,470,701 B2 | 6/2013 | Rogers et al. |
| 8,552,299 B2 | 10/2013 | Rogers et al. |
| 8,562,095 B2 | 10/2013 | Alleyne et al. |
| 8,664,699 B2 | 3/2014 | Nuzzo et al. |
| 8,666,471 B2 | 3/2014 | Rogers et al. |
| 8,679,888 B2 | 3/2014 | Rogers et al. |
| 8,722,458 B2 | 5/2014 | Rogers et al. |
| 8,729,524 B2 | 5/2014 | Rogers et al. |
| 8,754,396 B2 | 6/2014 | Rogers et al. |
| 2001/0003043 A1 | 6/2001 | Metspalu et al. |
| 2002/0021445 A1 | 2/2002 | Boxhevolnyi et al. |
| 2002/0094701 A1 | 7/2002 | Biegelsen et al. |
| 2002/0110766 A1 | 8/2002 | Tsai et al. |
| 2003/0006527 A1 | 1/2003 | Rabolt et al. |
| 2003/0032892 A1 | 2/2003 | Erlach et al. |
| 2003/0082889 A1 | 5/2003 | Maruyama et al. |
| 2003/0087476 A1 | 5/2003 | Oohata et al. |
| 2003/0138704 A1 | 7/2003 | Mei et al. |
| 2003/0149456 A1 | 8/2003 | Rottenberg et al. |
| 2003/0178316 A1 | 9/2003 | Jacobs et al. |
| 2003/0222282 A1 | 12/2003 | Fjelstad et al. |
| 2003/0227116 A1 | 12/2003 | Halik et al. |
| 2004/0005723 A1 | 1/2004 | Empedocles et al. |
| 2004/0026684 A1 | 2/2004 | Empedocles et al. |
| 2004/0079464 A1 | 4/2004 | Kumakura |
| 2004/0081384 A1 | 4/2004 | Datesman et al. |
| 2004/0095658 A1 | 5/2004 | Buretea et al. |
| 2004/0112964 A1 | 6/2004 | Empedocles et al. |
| 2004/0136866 A1 | 7/2004 | Pontis et al. |
| 2004/0146560 A1 | 7/2004 | Whiteford et al. |
| 2004/0155290 A1 | 8/2004 | Mech et al. |
| 2004/0178390 A1 | 9/2004 | Whiteford |
| 2004/0192082 A1 | 9/2004 | Wagner et al. |
| 2004/0200734 A1 | 10/2004 | Co et al. |
| 2004/0206448 A1 | 10/2004 | Dubrow |
| 2004/0211458 A1 | 10/2004 | Gui et al. |
| 2004/0211459 A1 | 10/2004 | Suenaga et al. |
| 2004/0250950 A1 | 12/2004 | Dubrow |
| 2004/0252559 A1 | 12/2004 | Gupta |
| 2005/0020094 A1 | 1/2005 | Forbes et al. |
| 2005/0038498 A1 | 2/2005 | Dubrow et al. |
| 2005/0082526 A1 | 4/2005 | Bedell et al. |
| 2005/0124712 A1 | 6/2005 | Anderson et al. |
| 2005/0133954 A1 | 6/2005 | Homola |
| 2005/0214962 A1 | 9/2005 | Daniels et al. |
| 2005/0227389 A1 | 10/2005 | Bhattacharya et al. |
| 2005/0233546 A1 | 10/2005 | Oohata et al. |
| 2005/0238967 A1 | 10/2005 | Rogers et al. |
| 2005/0255686 A1 | 11/2005 | Yamano et al. |
| 2005/0260706 A1 | 11/2005 | Kaplan et al. |
| 2005/0261561 A1 | 11/2005 | Jones et al. |
| 2006/0038182 A1 | 2/2006 | Rogers et al. |
| 2006/0049485 A1 | 3/2006 | Pan et al. |
| 2006/0084012 A1 | 4/2006 | Nuzzo et al. |
| 2006/0085976 A1 | 4/2006 | Eldridge et al. |
| 2006/0102525 A1 | 5/2006 | Volkel et al. |
| 2006/0119853 A1 | 6/2006 | Baumberg et al. |
| 2006/0127817 A1 | 6/2006 | Ramanujan et al. |
| 2006/0129056 A1 | 6/2006 | Leuthardt et al. |
| 2006/0132025 A1 | 6/2006 | Gao et al. |
| 2006/0134893 A1 | 6/2006 | Savage et al. |
| 2006/0159837 A1 | 7/2006 | Kaplan et al. |
| 2006/0169989 A1 | 8/2006 | Bhatacharya |
| 2006/0173364 A1 | 8/2006 | Clancy et al. |
| 2006/0177479 A1 | 8/2006 | Giachelli et al. |
| 2006/0178655 A1 | 8/2006 | Santini et al. |
| 2006/0186492 A1* | 8/2006 | Boettiger .......... H01L 27/14601 257/414 |
| 2006/0244105 A1 | 11/2006 | Forbes et al. |
| 2006/0255341 A1 | 11/2006 | Pinnington et al. |
| 2006/0273279 A1 | 12/2006 | Kaplan et al. |
| 2006/0279191 A1 | 12/2006 | Gehegan et al. |
| 2006/0286488 A1 | 12/2006 | Rogers et al. |
| 2006/0286785 A1 | 12/2006 | Rogers et al. |
| 2007/0009968 A1 | 1/2007 | Cunningham et al. |
| 2007/0031607 A1 | 2/2007 | Dubson et al. |
| 2007/0032089 A1 | 2/2007 | Nuzzo et al. |
| 2007/0043416 A1 | 2/2007 | Callas et al. |
| 2007/0058254 A1 | 3/2007 | Kim |
| 2007/0073130 A1 | 3/2007 | Finch et al. |
| 2007/0187862 A1 | 8/2007 | Kaplan et al. |
| 2007/0212730 A1 | 9/2007 | Vepari et al. |
| 2007/0227586 A1 | 10/2007 | Zapalac |
| 2007/0233208 A1 | 10/2007 | Kurtz et al. |
| 2007/0257821 A1 | 11/2007 | Son et al. |
| 2008/0000871 A1 | 1/2008 | Suh et al. |
| 2008/0038236 A1 | 2/2008 | Gimble et al. |
| 2008/0055581 A1 | 3/2008 | Rogers et al. |
| 2008/0085272 A1 | 4/2008 | Kaplan et al. |
| 2008/0090322 A1 | 4/2008 | Mech et al. |
| 2008/0102096 A1 | 5/2008 | Molin et al. |
| 2008/0108171 A1 | 5/2008 | Rogers et al. |
| 2008/0152281 A1 | 6/2008 | Lundquist et al. |
| 2008/0157235 A1 | 7/2008 | Rogers et al. |
| 2008/0183076 A1 | 7/2008 | Witte et al. |
| 2008/0203431 A1 | 8/2008 | Garcia et al. |
| 2008/0212102 A1 | 9/2008 | Nuzzo et al. |
| 2008/0237443 A1* | 10/2008 | Oliver .............. H01L 27/14618 250/200 |
| 2008/0239755 A1 | 10/2008 | Parker et al. |
| 2008/0280360 A1 | 11/2008 | Kaplan et al. |
| 2008/0288037 A1 | 11/2008 | Neysmith et al. |

(56) References Cited

U.S. PATENT DOCUMENTS

| | | |
|---|---|---|
| 2008/0293919 A1 | 11/2008 | Kaplan et al. |
| 2009/0004737 A1 | 1/2009 | Borenstein et al. |
| 2009/0012533 A1 | 1/2009 | Barbagli et al. |
| 2009/0028910 A1 | 1/2009 | Desimone et al. |
| 2009/0149930 A1 | 6/2009 | Schenck |
| 2009/0198293 A1 | 8/2009 | Cauller et al. |
| 2009/0199960 A1 | 8/2009 | Nuzzo et al. |
| 2009/0202614 A1 | 8/2009 | Kaplan et al. |
| 2009/0208555 A1 | 8/2009 | Kuttler et al. |
| 2009/0221896 A1 | 9/2009 | Rickert et al. |
| 2009/0232963 A1 | 9/2009 | Kaplan et al. |
| 2009/0234026 A1 | 9/2009 | Kaplan et al. |
| 2009/0289246 A1 | 11/2009 | Schneider et al. |
| 2009/0293664 A1 | 12/2009 | Aabloo et al. |
| 2009/0294803 A1 | 12/2009 | Nuzzo et al. |
| 2010/0002402 A1 | 1/2010 | Rogers et al. |
| 2010/0028451 A1 | 2/2010 | Kaplan et al. |
| 2010/0046902 A1 | 2/2010 | Kaplan et al. |
| 2010/0052112 A1 | 3/2010 | Rogers et al. |
| 2010/0055438 A1 | 3/2010 | Kaplan et al. |
| 2010/0059863 A1 | 3/2010 | Rogers et al. |
| 2010/0063404 A1 | 3/2010 | Kaplan et al. |
| 2010/0065784 A1 | 3/2010 | Kaplan et al. |
| 2010/0068740 A1 | 3/2010 | Kaplan et al. |
| 2010/0070068 A1 | 3/2010 | Kaplan et al. |
| 2010/0072577 A1 | 3/2010 | Nuzzo et al. |
| 2010/0096763 A1 | 4/2010 | Kaplan et al. |
| 2010/0120116 A1 | 5/2010 | Kaplan et al. |
| 2010/0121420 A1 | 5/2010 | Fiset et al. |
| 2010/0141407 A1 | 6/2010 | Heubel et al. |
| 2010/0178304 A1 | 7/2010 | Wang et al. |
| 2010/0191328 A1 | 7/2010 | Kaplan et al. |
| 2010/0196447 A1 | 8/2010 | Kaplan et al. |
| 2010/0200752 A1 | 8/2010 | Lee et al. |
| 2010/0203226 A1 | 8/2010 | Kaplan et al. |
| 2010/0224950 A1 | 9/2010 | Dinyari et al. |
| 2010/0279112 A1 | 11/2010 | Kaplan et al. |
| 2010/0283069 A1 | 11/2010 | Rogers et al. |
| 2010/0289124 A1 | 11/2010 | Nuzzo et al. |
| 2010/0317132 A1 | 12/2010 | Rogers et al. |
| 2011/0034912 A1 | 2/2011 | DeGraff et al. |
| 2011/0071439 A1 | 3/2011 | Bach-y-Rita et al. |
| 2011/0129158 A1 | 6/2011 | Sato |
| 2011/0147715 A1 | 6/2011 | Rogers et al. |
| 2011/0168403 A1 | 7/2011 | Patel |
| 2011/0170225 A1 | 7/2011 | Rogers et al. |
| 2011/0171813 A1 | 7/2011 | Rogers et al. |
| 2011/0187798 A1 | 8/2011 | Rogers et al. |
| 2011/0220890 A1 | 9/2011 | Nuzzo et al. |
| 2011/0230747 A1 | 9/2011 | Rogers et al. |
| 2011/0266561 A1 | 11/2011 | Rogers et al. |
| 2011/0276112 A1 | 11/2011 | Simon et al. |
| 2011/0277813 A1 | 11/2011 | Rogers et al. |
| 2011/0316120 A1 | 12/2011 | Rogers et al. |
| 2012/0157804 A1 | 6/2012 | Rogers et al. |
| 2012/0165759 A1 | 6/2012 | Rogers et al. |
| 2012/0261551 A1 | 10/2012 | Rogers et al. |
| 2012/0320581 A1 | 12/2012 | Rogers et al. |
| 2012/0327608 A1 | 12/2012 | Rogers et al. |
| 2013/0036928 A1 | 2/2013 | Rogers et al. |
| 2013/0041235 A1 | 2/2013 | Rogers et al. |
| 2013/0072775 A1 | 3/2013 | Rogers et al. |
| 2013/0100618 A1 | 4/2013 | Rogers et al. |
| 2013/0140649 A1 | 6/2013 | Rogers et al. |
| 2013/0333094 A1 | 12/2013 | Rogers et al. |
| 2014/0163390 A1 | 6/2014 | Rogers et al. |
| 2014/0191236 A1 | 7/2014 | Nuzzo et al. |
| 2014/0216524 A1 | 8/2014 | Rogers et al. |
| 2014/0220422 A1 | 8/2014 | Rogers et al. |

FOREIGN PATENT DOCUMENTS

| | | |
|---|---|---|
| CN | 101772348 A | 7/2010 |
| DE | 4241045 C1 | 5/1994 |
| DE | 19748173 | 5/1999 |
| EP | 0 929 097 | 7/1999 |
| EP | 1 357 773 | 10/2003 |
| EP | 1 467 224 | 10/2004 |
| EP | 1 477 230 | 11/2004 |
| EP | 1 498 456 | 1/2005 |
| EP | 1 511 096 | 3/2005 |
| EP | 1 558 444 | 8/2005 |
| EP | 1 613 796 | 1/2006 |
| EP | 1 773 240 | 4/2007 |
| EP | 1 915 436 | 4/2008 |
| EP | 1 726 329 | 8/2009 |
| EP | 2 086 749 | 8/2009 |
| EP | 2 101 975 | 9/2009 |
| EP | 2 107 964 | 10/2009 |
| EP | 2 109 634 | 10/2009 |
| EP | 2 129 772 | 12/2009 |
| EP | 2 206 017 | 7/2010 |
| EP | 2 211 876 | 8/2010 |
| EP | 2 249 886 | 11/2010 |
| JP | 06-118441 | 4/1994 |
| JP | 6-163365 | 6/1994 |
| JP | 11-026344 | 1/1999 |
| JP | 11-142878 | 5/1999 |
| JP | 2001-007340 | 1/2001 |
| JP | 2002092984 | 3/2002 |
| JP | 2006-504450 | 2/2006 |
| JP | 2006-186294 | 7/2006 |
| JP | 2007-515391 | 6/2007 |
| JP | 2008-502739 | 1/2008 |
| JP | 2010-508852 | 3/2010 |
| JP | 2010-509593 | 3/2010 |
| JP | 2010-509644 | 3/2010 |
| JP | 2010-509645 | 3/2010 |
| JP | 2010-522583 | 7/2010 |
| JP | 2010-529230 | 8/2010 |
| KR | 10-2008-0069553 | 7/2008 |
| TW | 367570 | 8/1999 |
| TW | 494257 | 7/2002 |
| TW | 200836353 | 9/2008 |
| WO | WO 98/49936 | 11/1998 |
| WO | WO 99/45860 | 9/1999 |
| WO | WO 00/46854 | 8/2000 |
| WO | WO 00/49421 | 8/2000 |
| WO | WO 00/49658 | 8/2000 |
| WO | WO 00/55915 | 9/2000 |
| WO | WO 00/55916 | 9/2000 |
| WO | WO 01/31082 | 5/2001 |
| WO | WO 01/33621 | 5/2001 |
| WO | WO 01/66833 | 9/2001 |
| WO | WO 01/98838 | 12/2001 |
| WO | WO 02/27701 | 4/2002 |
| WO | WO 02/43032 | 5/2002 |
| WO | WO 02/073699 | 9/2002 |
| WO | WO 02/092778 | 11/2002 |
| WO | WO 02/097708 | 12/2002 |
| WO | WO 02/097724 | 12/2002 |
| WO | WO 2004/099068 | 12/2002 |
| WO | WO 03/030194 | 4/2003 |
| WO | WO 03/032240 | 4/2003 |
| WO | WO 03/049201 | 6/2003 |
| WO | WO 03/063211 | 7/2003 |
| WO | WO 03/085700 | 10/2003 |
| WO | WO 03/085701 | 10/2003 |
| WO | WO 03/092073 | 11/2003 |
| WO | WO 2004/000915 | 12/2003 |
| WO | WO 2004/001103 | 12/2003 |
| WO | WO 2004/003535 | 1/2004 |
| WO | WO 2004/022637 | 3/2004 |
| WO | WO 2004/022714 | 3/2004 |
| WO | WO 2004/023527 | 3/2004 |
| WO | WO 2004/024407 | 3/2004 |
| WO | WO 2004/027822 | 4/2004 |
| WO | WO 2004/032190 | 4/2004 |
| WO | WO 2004/032191 | 4/2004 |
| WO | WO 2004/032193 | 4/2004 |
| WO | WO 2004/034025 | 4/2004 |
| WO | WO 2004/062697 | 7/2004 |
| WO | WO 2004/086289 | 10/2004 |
| WO | WO 2004/094303 | 11/2004 |

(56) References Cited

FOREIGN PATENT DOCUMENTS

| | | |
|---|---|---|
| WO | WO 2004/100252 | 11/2004 |
| WO | WO 2004/105456 | 12/2004 |
| WO | WO 2005/000483 | 1/2005 |
| WO | WO 2005/005679 | 1/2005 |
| WO | WO 2005/012606 | 2/2005 |
| WO | WO 2005/015480 | 2/2005 |
| WO | WO 2005/017962 | 2/2005 |
| WO | WO 2005/022120 | 3/2005 |
| WO | WO 2005/029578 | 3/2005 |
| WO | WO 2005/054119 | 6/2005 |
| WO | WO 2005/104756 | 11/2005 |
| WO | WO 2005/122285 | 12/2005 |
| WO | WO 2005/123114 | 12/2005 |
| WO | WO 2006/028996 | 3/2006 |
| WO | WO 2006/042287 | 4/2006 |
| WO | WO 2006/076711 | 7/2006 |
| WO | WO 2006/104069 | 10/2006 |
| WO | WO 2006/130721 | 12/2006 |
| WO | WO 2007/000037 | 1/2007 |
| WO | WO 2007/016524 | 2/2007 |
| WO | WO 2007/028003 | 3/2007 |
| WO | WO 2007/056183 | 5/2007 |
| WO | WO 2007/126412 | 11/2007 |
| WO | WO 2008/030666 | 3/2008 |
| WO | WO 2008/030960 | 3/2008 |
| WO | WO 2008/036837 | 3/2008 |
| WO | WO 2008/055054 | 5/2008 |
| WO | WO 2008/085904 | 7/2008 |
| WO | WO 2008/103464 | 8/2008 |
| WO | WO 2008/106485 | 9/2008 |
| WO | WO 2008/108838 | 9/2008 |
| WO | WO 2008/118133 | 10/2008 |
| WO | WO 2008/118211 | 10/2008 |
| WO | WO 2008/127401 | 10/2008 |
| WO | WO 2008/127402 | 10/2008 |
| WO | WO 2008/127403 | 10/2008 |
| WO | WO 2008/127404 | 10/2008 |
| WO | WO 2008/127405 | 10/2008 |
| WO | WO 2008/140562 | 11/2008 |
| WO | WO 2008/143635 | 11/2008 |
| WO | WO 2008/150861 | 12/2008 |
| WO | WO 2009/011709 | 1/2009 |
| WO | WO 2009/023615 | 2/2009 |
| WO | WO 2009/061823 | 5/2009 |
| WO | WO 2009/075625 | 6/2009 |
| WO | WO 2009/076088 | 6/2009 |
| WO | WO 2009/090398 | 7/2009 |
| WO | WO 2009/100280 | 8/2009 |
| WO | WO 2009/111641 | 9/2009 |
| WO | WO 2009/114115 | 9/2009 |
| WO | WO 2009/114689 | 9/2009 |
| WO | WO 2009/118678 | 10/2009 |
| WO | WO 2009/126689 | 10/2009 |
| WO | WO 2009/140588 | 11/2009 |
| WO | WO 2009/155397 | 12/2009 |
| WO | WO 2010/005707 | 1/2010 |
| WO | WO 2010/036807 | 4/2010 |
| WO | WO 2010/036992 | 4/2010 |
| WO | WO 2010/040528 | 4/2010 |
| WO | WO 2010/042798 | 4/2010 |
| WO | WO 2010/049881 | 5/2010 |
| WO | WO 2010/057142 | 5/2010 |
| WO | WO 2010/065957 | 6/2010 |
| WO | WO 2010/081989 | 7/2010 |
| WO | WO 2010/126640 | 11/2010 |
| WO | WO 2010/132552 | 11/2010 |
| WO | WO 2010/141133 | 12/2010 |
| WO | WO 2011/005381 | 1/2011 |
| WO | WO 2011/006133 | 1/2011 |
| WO | WO 2011/008842 | 1/2011 |
| WO | WO 2011/011347 | 1/2011 |
| WO | WO 2011/026101 | 3/2011 |
| WO | WO 2011/038401 | 3/2011 |
| WO | WO 2011/041395 | 4/2011 |
| WO | WO 2011/046652 | 4/2011 |
| WO | WO 2011/084450 | 7/2011 |
| WO | WO 2011/112931 | 9/2011 |
| WO | WO 2011/115643 | 9/2011 |
| WO | WO 2012/167096 | 12/2012 |
| WO | WO 2014/124044 | 8/2014 |
| WO | WO 2014/124049 | 8/2014 |
| WO | WO 2014/126927 | 8/2014 |
| WO | WO 2014/138465 | 9/2014 |

OTHER PUBLICATIONS

Abbaschian et al. (Dec. 2005) "High Pressure-High Temperature Growth of Diamond Crystals Using Split Sphere Apparatus," *Diamond Relat. Mater.* 14(11-12):1916-1919.

Adachi et al (1982) "Chemical Etching of InGaAsP/InP DH Wafer," *J. Electrochem. Soc.* 129:1053-1062.

Adachi et al. (1983) "Chemical Etching Characteristics of (001)GaAs," *J. Electrochem. Soc.* 130:2427-2435.

Adrega et al. (2010) "Stretchable Gold Conductors Embedded in PDMS and Patterned by Photolithography: Fabrication and Electromechanical Characterization," *J. Micromech. Microeng.* 20:055025.

Ago et al. (2005) "Aligned Growth of Isolated Single-Walled Carbon Nanotubes Programmed by Atomic Arrangement of Substrate Surface," *Chem. Phys. Lett.* 408:433-438.

Ago et al. (2006) "Synthesis of Horizontally-Aligned Single-Walled Carbon Nanotubes with Controllable Density on Sapphire Surface and Polarized Raman Spectroscopy," *Chem. Phys. Lett.* 421:399-403.

Ahmed et al. (Web Release Oct. 11, 2005) "Extending the 3ω-Method to the MHz Range for Thermal Conductivity Measurements of Diamond Thin Films," *Diamond Relat. Mater.* 15(2-3):389-393.

Ahn et al. (2007) "Bendable Integrated Circuits on Plastic Substrates by Use of Printed Ribbons of Single-Crystalline Silicon," *Appl. Phys. Lett.* 90:213501.

Ahn et al. (Dec. 15, 2006) "Heterogeneous Three-Dimensional Electronics by Use of Printed Semiconductor Nanomaterials," *Science* 314:1754-1757.

Ahn et al. (Jun. 2006) "High-Speed Mechanically Flexible Single-Crystal Silicon Thin-Film Transistors on Plastic Substrates," *IEEE Electron Dev. Lett.* 27(6):460-462.

Alanen et al. (2004) "Measurement of Hydration in the Stratum Corneum with the Moisturemeter and Comparison with the Corneometer," *Skin Research and Technology.* 10:32-37.

Alekseev, et al. (2008) "Millimeter Wave Reflectivity Used for Measurement of Skin Hydration with Different Moisturizers," *Skin Res. Technol*, 14:390-396.

Al-Halhouli et al. (2008) "Nanoindentation Testing of SU-8 Photoresist Mechanical Properties," *Microelectronic Eng.* 85:942-944.

Al-Hardan et al. (2010) "The Effect of Oxygen Ratio on the Crystallography and Optical Emission Properties of Reactive RF Sputtered ZnO Films," *Physica B.* 405:1081.

Aliot, E. M. et al. (2009) "EHRA/HRS Expert Consensus on Catheter Ablation of Ventricular Arrhythmias: Developed in a partnership with the European Heart Rhythm Association (EHRA), a Registered Branch of the European Society of Cardiology (ESC), and the Heart Rhythm Society (HRS); in collaboration with the American College of Cardiology (ACC) and the American Heart Association (AHA)," *Europace* 11:771-817.

Alivisatos et al. (1996) "Semiconductor Clusters, Nanocrystals, and Quantum Dots," *Science* 271:933-937.

Alivisatos et al. (1998) "From Molecules to Materials: Current Trends and Future Directions," *Adv. Mater.* 10:1297-1336.

Allen et al. (Feb. 20, 2006) "Nanomaterial Transfer Using Hot Embossing for Flexible Electronic Devices," *Appl. Phys. Lett.* 88:083112.

Al-Sarawi et al. (Feb. 1998) "A Review of 3-D Packaging Technology," *IEEE Trans. Comp. Packag. Manufac. Technol. B* 21(1):2-14.

Altman et al. (2003) "Silk-Based Biomaterials," *Biomaterials* 24:401-416.

(56) References Cited

OTHER PUBLICATIONS

Amano et al. (Feb. 3, 1986) "Metalorganic Vapor Phase Epitaxial Growth of a High Quality GaN Film Using an AlN Buffer Layer," *Appl. Phys. Lett.* 48(5):353-355.
Ambrosy et al. (1996) "Silicon Motherboards for Multichannel Optical Modules," *IEEE Trans. Compon. Pack. A* 19:34-40.
Amir et al. (2000) "The Influence of Helium-Neon Irradiation on the Viability of Skin Flaps in the Rat," *Br. J. Plast. Surg.* 53:58-62.
Amsden et al. (Nov. 9, 2009) "Spectral Analysis of Induced Color Change on Periodically Nanopatterned Silk Films," *Opt. Express* 17(23):21271-21279.
Andersen et al. (2004) "Selecting the Signals for a Brain-Machine Interface," *Curr. Opin. Neurobiol.* 14:720-726.
Andersson et al. (Oct. 16, 2002) "Active Matrix Displays Based on All-Organic Electrochemical Smart Pixels Printed on Paper," *Adv. Mater.* 14:1460-1464.
Ando et al. (2004) "Self-Aligned Self-Assembly Process for Fabricating Organic Thin-Film Transistors," *Appl. Phys. Lett.* 85:1849-1851.
Andosca et al. (2012) "Experimental and Theoretical Studies on MEMS Piezoelectric Vibrational Energy Harvesters with Mass Loading," *Sensors and Actuators A*. 178:76.
Angadi et al. (Web Release Jun. 1, 2006) "Thermal Transport and Grain Boundary Conductance in Ultrananocrystalline Diamond Thin Films," *J. Appl. Phys.* 99:114301.
Angelopoulos et al. (Sep. 17-21, 2012) "Manufacturing aspects of an ultra-thin chip technology," In; Solid-State Device Research Conference (ESSDERC) 2012: Proceedings of the European. Bordeaux, France. Ed.: Yann Deval pp. 141-144.
Aoki et al. (2003) "Microassembly of Semiconductor Three Dimensional Photonic Crystals," *Nat. Mater.* 2:117-121.
Arnold et al. (2003) "Field-Effect Transistors Based on Single Semiconducting Oxide Nanobelts," *J. Phys. Chem. B* 107(3):659-663.
Arumugam et al. (1994) "Effect of Strain Rate on the Fracture Behaviour of Skin," *J. Bioscience*. 19(3):307-313.
Attas et al. (2002) "Near-IR Spectroscopic Imaging for Skin Hydration: The Long and the Short of it," *Biopolymers.* 67:96-106.
Ayón et al. (Jan. 1999) "Characterization of a Time Multiplexed Inductively Coupled Plasma Etcher," *J. Electrochem. Soc.* 146(1)339-349.
Baca et al. (2007) "Printable Single-Crystal Silicon Micro/Nanoscale Ribbons, Platelets and Bars Generated from Bulk Wafers," *Adv. Funct. Mater.* 17:3051-3062.
Baca et al. (2008) "Semiconductor Wires and Ribbons for High-Performance Flexible Electronics," *Angew. Chem. Int. Ed.* 47:5524-5542.
Bachtold et al. (Nov. 9, 2001) "Logic Circuits with Carbon Nanotube Transistors," *Science* 294:1317-1320.
Bach-y-Rita et al. (2003) "Seeing with the Brain," *Int. J. Hum-Comput. Int.*15:285-296.
Bae et al. (Jul. 1, 2002) "Single-Crystalline Gallium Nitride Nanobelts," *Appl. Phys. Lett.* 81(1):126-128.
Baek et al. (2008) "Flexible polymeric dry electrodes for the long-term monitoring of ECG," *Sensor Actuat. A: Phys.* 143:423-429.
Ball et al. (2004) "Towards an Implantable Brain-Machine Interface Based on Epicortical Field Potentials," *Biomed. Tech.* 49:756-759.
Balmer et al. (2005) "Diffusion of Alkanethiols in PDMS and Its Implications on Microcontact Printing (µCP)," *Langmuir* 21(2):622-632.
Banerjee et al. (May 2001) "3-D ICs: A Novel Chip Design for Improving Deep-Submicrometerinterconnect Performance and Systems-on-Chip Integration," *Proc. IEEE* 89(5):602-633.
Bao et al. (1997) "High-Performance Plastic Transistors Fabricated by Printing Techniques," *Chem. Mater.* 9:1299-1301.
Bao et al. (1999) "Printable Organic and Polymeric Semiconducting Materials and Devices," *J. Mater. Chem.* 9:1895-1904.
Barbottin (1989) Ch. 15 In; Instabilities in Silicon Devices. vol. 2 *Elsevier.* Amsterdam, The Netherlands.

Barel et al. (1997) "In Vitro Calibration of the Capacitance Method (Corneometer CM 825) and Conductance Method (Skicon-200) for the Evaluation of the Hydration State of the Skin," *Skin Research and Technology.* 3:107-113.
Barfield et al. (1995) "Comparison of Human Sensory Capabilities with Technical Specifications for Virtual Environment Equipment," *Presence-Teleoperators and Virtual Environments.* 4:329-356.
Barquins, M. (1992) "Adherence, Friction and Wear of Rubber-Like Materials," *Wear* 158:87-117.
Barrandon et al. (1985) "Cell size as a determinant of the clone-forming ability of human keratinocytes," *Proc. Natl. Acad. Sci. USA* 82:5390-5394.
Baskoutas et al. (2011) "Transition in the Optical Emission Polarization of ZnO Nanorods," *J. Phys. Chem. C.* 115:15862.
Bates, F.S. (1991) "Polymer-Polymer Phase Behavior," *Science* 251:898-905.
Battaglia et al. (2003) "Colloidal Two-Dimensional Systems: CdSe Quantum Shells and Wells," Angew. Chem. Int. Ed. 442:5035-5039.
Bauer et al. (2004) "Biological Applications of High Aspect Ratio Nanoparticles," *J. Mater. Chem.* 14:517-526.
Benfield et al. (2007) "Waterproofing EMG Instrumentation," *Biol. Res. Nurs.* 8:195.
Berg et al. (2003) "Tailored Micropatters Through Weak Polyelectrolyte Stamping," Langmuir 19:2231-2237.
Berger (1929) "Über das Elektrenkephalogram des. Menschen." *Arch Psychiatr Nervenkr.* 87:527-570.
Bernard et al. (1998) "Printing Patterns of Proteins," *Langmuir* 14(9):2225-2229.
Bernardini et al. (1997) "Spontaneous Polarization and Piezoelectric Constants of III-V nitrides," *Physics Review B.* 56:10024.
Bett et al. (Aug. 1999) "III-V Compounds for Solar Cell Applications," *Appl. Phys. A. Mater. Sci.* 69(2):119-129.
Bettinger et al. (2010) "Biomaterials-Based Organic Electronic Devices," *Polym. Int.* 59:563.
Bettinger et al. (2010) "Organic Thin-Film Transistors Fabricated on Resorbable Biomaterial Substrates," *Adv. Mater.* 22:651.
Bhunia et al. (2004) "Free-Standing and Vertically Aligned InP Nanowires Grown by Metalorganic Vapor Phase Epitaxy," *Physica E* 21:583-587.
Bhushan et al. (Nov. 2004) "Multiwalled Carbon Nanotube AFM Probes for Surface Characterization of Micro/Nanostructures," *Microsyst. Technol.* 10(8-9):633-639.
Bietsch et al. (Oct. 1, 2000) "Conformal Contact and Pattern Stability of Stamps Used for Soft Lithography," *J. Appl. Phys.* 88(7):4310-4318.
BIOFLEX—Biocompatible Flexible Electronic Circuits. Available at http://tfcg.elis.ugent.be/projects/bioflex. Accessed Feb. 8, 2012.
Biot. (1963) "Surface Instability of Rubber in Compression," *Appl. Sci. Res. A.* 12:168-182.
Bishay et al. (2000) "Temperature Coefficient of the Surface Resistivity of Two-Dimensional Island Gold Films," *J. Phys. D. Appl. Phys.* 33(18):2218-2222.
Blanchet et al. (2003) "Large Area, High Resolution, Dry Printing of Conducting Polymers for Organic Electronics," *Appl. Phys. Lett.* 82:463-465.
Blanchet et al. (2003) "Printing Techniques for Plastic Electronics," *J. Imag. Sci. Tech.* 47(4):296-303.
Blazdell et al. (Nov. 1999) "Preparation of Ceramic Inks for Solid Freeforming Using a Continuous Jet Printer," *J. Mat. Syn. Process.* 7(6):349-356.
Blichmann et al. (1987) "Hydration Studies on Scaly Hand Eczema," *Contact Dermatitis.* 16:155-159.
Blom et al. (1990) "Thin-film ZnO as Micromechanical Actuator at Low Frequencies," *Sensors and Actuators.* 21:226.
Boguniewicz, et al. (2008) "A Multidisciplinary Approach to Evaluation and Treatment of Atopic Dermatitis," *Seminars in Cutaneous Medicine and Surgery.* 27:115-127.
Boltau et al. (1998) "Surface-Induced Structure Formation of Polymer Blends on Patterned Substrates," *Nature* 391:877-879.
Boncheva et al. (Mar. 15, 2005) "Magnetic Self-Assembly of Three-Dimensional Surfaces from Planar Sheets," *Proc. Natl. Acad. Sci. USA* 102(11):3924-3929.

(56) References Cited

OTHER PUBLICATIONS

Boncheva et al. (Mar. 8, 2005) "Templated Self-Assembly: Formation of Folded Structures by Relaxation of Pre-Stressed, Planar Tapes," *Adv. Mater.* 17(5):553-557.

Bourzac, K. (May/Jun. 2010) "TR10: Implantable Electronics," *Technology Review*, Published by MIT, http://www.technologyreview.com/biomedicine/25086/?a=f.

Bowden et al. (1997) "Self Assembly of Mesoscale Objects into Ordered Two-Dimensional Arrays," *Science* 276:233-235.

Bowden et al. (1998) "Spontaneous Formation of Ordered Structures in Thin Films of Metals Supported on an Elastomeric Polymer," *Nature* 393:146-149.

Bowden et al. (2001) "Molecule-Mimetic Chemistry and Mesoscale Self-Assembly," *Acc. Chem. Res.* 34:231-238.

Bracher et al. (2009) "Shaped Films of Ionotropic Hydrogels Fabricated Using Templates of Patterns Paper," *Adv. Mater.* 21:445-450.

Bradley et al. (2003) "Flexible Nanotube Electronics," *Nano Lett.*, vol. 3, No. 10, pp. 1353-1355.

Braun et al. (1999) "Electrochemically Grown Photonic Crystals," *Nature* 402:603-604.

Briscoe (2012) "Measured Efficiency of a ZnO Nanostructured Diode Piezoelectric Energy Harvesting Device," *Appl. Phys. Lett* 101:093902.

Britton et al. (Web Release Oct. 25, 2005) "Microstructural Defect Characterization of a Si:H Deposited by Low Temperature HW-CVD on Paper Substrates," *Thin Solid Films* 501(1-2):79-83.

Brown et al. (2005) "Evaluation of Polydimethylsiloxane Scaffolds with Physiologically-Relevant Elastic Moduli: Interplay of Substrate Mechanics and Surface Chemistry Effects on Vascular Smooth Muscle Cell Response," *Biomaterials* 26:3123-3129.

Brown et al. (Dec. 19, 2001) "Heterogeneous Materials Integration: Compliant Substrates to Active Device and Materials Packaging," *Mater. Sci. Eng. B* 87(3):317-322.

Brown, H.R. (1991) "The Adhesion Between Polymers," *Ann. Rev. Mater. Sci.* 21:463-489.

Bruschi et al. (2001) "Micromachined Silicon Suspended Wires With Submicrometric Dimensions," *Microelectron. Eng.* 57-58:959-965.

Buma et al. (2001) "High-Frequency Ultrasound Array Element Using Thermoelastic Expansion in an Elastomeric Film," *Appl. Phys. Lett.* 79:548-550.

Burdinski et al. (2005) "Single Etch Patterning of Stacked Silver and Molybdenum Alloy Layers on Glass Using Microcontat Wave Printing," *J. Am. Chem. Soc.* 127(31):10786-10787.

Burdinski, D. (non-dated) "Soft Lithography and Microcontact Wave Printing," http://www.research.philips.com/technologies/light_dev_microsys/softlitho/index.html, Downloaded May 23, 2007.

Burge et al. (Jun. 25, 1997) "X-Ray Holography for VLSI Using Synthetic Bilevel Holograms," *Proc. Int. Soc. Opt. Eng.* 3183:2-13.

Burghartz et al. (2009) "A new fabrication and assembly process for ultra-thin chips," *IEEE T. Electron Dev.* 56:321-327.

Burgin et al. (2000) "Large Area Submicrometer Contact Printing Using a Contact Aligner," *Langmuir* 16:5371-5375.

Burns et al. (2003) "Printing of Polymer Thin-Film Transistors for Active-Matrix-Display Applications," *J. Soc. Inf. Display* 11:599-604.

Camacho et al. (2011) "Structural, Optical and Electrical Properties of ZnO Thin Films Grown by Radio Frequency (Rf) Sputtering in Oxygen Atmosphere," *International Journal of Physical Sciences.* 6:6660.

Campbell et al. (2000) "Fabrication of Photonic Crystals for the Visible Spectrum by Holographic Lithography," *Nature* 404:53-56.

Cantatore et al. (2007) "13.56-MHz RFID system based on organic transponders," *IEEE Journal of Solid-State Circuits.* 42:84-92.

Cao et al. (2006) "Bilayer Organic-Inorganic Gate Dielectrics for High-Performance, Low-Voltage, Single-Walled Carbon Nanotube Thin-Film Transistors, Complementary Logic Gates, and p-n Diodes on Plastic Substrates," *Adv. Funct. Mater.* 16:2355-2362.

Cao et al. (2006) "Highly Bendable, Transparent Thin-Film Transistors That Use Carbon-Nanotube-Based Conductors and Semiconductors with Elastomeric Delectrics," *Adv. Mater.* 18(3):304-309.

Cao et al. (2006) "Transparent flexible organic thin-film transistors that use printed single-walled carbon nanotube electrodes," *Applied Physics Letters* 88:113511.

Cao et al. (Jan. 5, 2009) "Ultrathin Films of Single-Walled Carbon Nanotubes for Electronics and Sensors: A Review of Fundamental and Applied Aspects," *Adv. Mater.* 21(1):29-53.

Cao et al. (Jul. 24, 2008) "Medium-Scale Carbon Nanotube Thin-Film Integrated Circuits on Flexible Plastic Substrates," *Nature* 454:495-500.

Carcia et al. (2006) "High-Performance ZnO Thin-Film Transistors on Gate Dielectrics Grown by Atomic Layer Deposition," *Appl. Phys. Lett.* 88:123509.

Carlson et al. (2012) "Transfer printing techniques for materials assembly and micro/nanodevice fabrication," *Adv. Mater.* 24:5284-5318.

Carr et al. (1998) "Measurement of Nanomechanical Resonant Structures in Single-Crystal Crystal Silicon," *J. Vac. Sci. Technol. B* 16:3821-3824.

Chang et al. (1994) "Process Techniques," "Lithography," and "Device-Related Physics and Principles " In; *GaAs High-Speed Devices: Physics, Technology and Circuit Application*, John Wiley and Sons, New York, pp. 115-278.

Chang et al. (2010) "Direct-Write Piezoelectric Polymeric Nanogenerator with High Energy Conversion Efficiency," *Nano Lett.*10:726.

Chaudhury et al. (1991) "Direct Measurement of Interfacial Interactions Between Semispherical Lenses and Flat Sheets of Poly(Dimethylsiloxane) and their Chemical Derivatives," *Langmuir.* 7:1013-1025.

Chen et al. (2003) "Characterization of Pd-GaAs Schottly Diodes Prepared by the Electrodes Plating Technique," *Semiconductor. Sci. Technol.* 18:620-626.

Chen et al. (2003) "Electronic Paper: Flexible Active-Matrix Electronics Ink Display," *Nature* 423:136.

Chen et al. (2005) "Humidity Sensors: A Review of Materials and Mechanisms," *Sensor Letters.* 3:274-295.

Chen et al. (2005) "InGaN Nanorings and Nanodots by Selective Area Epitaxy," *Appl. Phys. Lett.* 87:143111.

Chen et al. (2005) "The Role of Metal-Nanotube Caontact in the Performance of Carbon Nanotube Field-Effect Transistors," *Nano Lett.* 5(7):1497-1502.

Chen et al. (Feb. 27, 2006) "Complementary Carbon Nanotube-Gated Carbon Nanotube Thin-Fim Transistor," *Appl. Phys. Lett.* 88:093502.

Chen et al. (Jun. 2002) Effect of Process Parameters on the Surface Morphology and Mechanical Performance of Silicon Structures After Deep Reactive Ion Etching (DRIE) *J. Microelectromech. Syst.* 11(3):264-275.

Chen et al. (Mar. 2004) "A Family of Herringbone Patterns in Thin Films," *Scr. Mater.* 50(6):797-801.

Chen et al. (Mar. 24, 2006) "An Integrated Logic Crcuit Assembled on a Single Carbon Nanotube," *Science* 311:1735.

Chen et al. (Sep. 2004) "Herringbone Buckling Patterns of Compressed Thin Films on Compliant Substrates," *J. Appl. Mech.* 71:597-603.

Cheng et al. (2005) "Ink-Jet Printing, Self-Assembled Polyelectrolytes, and Electroless Plating: Low Cost Fabrication of Circuits on a Flexible Substrate at Room Temperature," *Macromol. Rapid Commun.* 26:247-264.

Cheung et al. (2007) "Flexible polyimide microelectrode array for in vivo recordings and current source density analysis," *Biosens. Bioelectron.* 22:1783.

Childs et al. (2002) "Decal Transfer Microlithography: A New Soft-Lithographic Patterning Method," *J. Am. Chem. Soc.* 124:13583-13596.

Childs et al. (2005) "Masterless Soft-Lithography: Patterning UV/Ozone-Induced Adhesion on Poly(dimethylsiloxane) Surfaces," *Langmuir* 21:10096-10105.

(56) References Cited

OTHER PUBLICATIONS

Childs et al. (Aug. 14, 2004) "Patterning of Thin-Film Microstructures on Non-Planar Substrate Surfaces Using Decal Transfer Lithography," *Adv. Mater.* 16(15):1323-1327.

Choi et al. (2003) "Investigation of Gate-Induced Drain Leakage (GIDL) Current in Thin Body Devices: Single-Gate Ultra-Thin Body, Symmetrical Double-Gate, and Asymmetrical Double-Gate MOSFETs," *Jpn. J. Appl. Phys.* 42:2073-2076.

Choi et al. (2007) "Biaxially Stretchable 'Wavy' Silicon Nanomembranes," *Nano Lett.* 7(6):1655-1663.

Choi et al. (2011) "Synthesis and properties of polyurethane-urea-based liquid bandage materials," *J. Appl. Polym. Sci.* 121:3516-3524.

Choi et al. (2012) "The influences of skin visco-elasticity, hydration level and aging on the formation of wrinkles: a comprehensive and objective approach," *Skin Res. Technol.* 19(1):e349-55.

Choi et al. (Web Release Jan. 25, 2005) "Simple Detachment Patterning of Organic Layers and Its Applications to Organic Light-Emitting Diodes," *Adv. Mater.* 17(2):166-171.

Choi-Yim et al. (1998) "The Effect of Silicon on the Glass Forming Ability of the $Cu_{47} Ti_{34} Zr_{11} Ni_8$ Bulk Metallic Glass Forming Alloy During Processing of Composites," *J. Appl. Phys.* 83:7993.

Chou et al. (2004) "An Orientation-Controlled Pentacene Film Aligned by Photoaligned Polyimide for Organic Thin-Film Transistor Applications," *Adv. Func. Mater.* 14:811-815.

Chou et al. (Jun. 8, 1999) "Micromachining on (111)-Oriented Silicon," *Sens. Actuators A* 75(3):271-277.

Chu et al. (2005) "High-Performance Organic Thin-Film Transistors with Metal Oxide/Metal Bilayer Electrode," *Appl. Phys. Lett.* 87:193508.

Chung et al. (2000) Silicon Nanowire Devices *Appl. Phys. Lett.* 76(15):2068-2070.

Chung et al. (2011) "Fabrication of Releasable Single-Crystal Silicon—Metal Oxide Field-Effect Devices and Their Deterministic Assembly on Foreign Substrates," *Adv. Func. Mater.* 21:3029.

Chung et al. (Jul. 1, 2003) "A Study on Formation of Al and $Al_2O_3$ on the Porous Paper by DC Magnetron Sputtering," *Surf. Coat. Technol.* 171(1-3):65-70.

Clarys et al. (1999) "Non-Invasive Electrical Measurements for the Evaluation of the Hydration State of the Skin: Comparison Between Three Conventional Instruments—the Comeometer®, the Skicon® and the Nova DPM®," *Skin Research and Technology.* 5:14-20.

Clerc, L. (1976) "Directional Differences of Impulse Spread in Trabecular Muscle from Mammalian Heart," *J. Physiol.* 255:335-346.

Cohen-Karni et al. (2009) "Flexible Electrical Recording from Cells Using Nanowire Transistor Arrays," *Proc. Natl. Acad. Sci. USA* 106:7309-7313.

Cole et al. (2008) "Patterned Growth and Transfer of ZnO Micro- and Nanocrystals with Size and Location Control," *Adv. Mater.* 20:1474-1478.

Collins et al. (Apr. 27, 2001) "Engineering Carbon Nanotubes and Nanotube Circuits Using Electrical Breakdown," *Science* 292:706-709.

Corazza et al. (2007) "Photobiomodulation on the Angiogenesis of Skin Wounds in Rats Using Different Light Sources," *Photomedicine Laser Surg.* 25:102-106.

Cox, H. L. (1952) "The Elasticity and Strength of Paper and Other Fibrous Materials," *Br. J. Appl. Phys.* 3:72-79.

Creagh et al. (2003) "Design and Performance of Inkjet Print Heads for Non-Graphic-Arts Applications," *MRS Bull.* 28:807-811.

Crone et al. (Feb. 3, 2000) "Large-Scale Complementary Integrated Circuits Based on Organic Transistors," *Nature* 403:521-523.

Crowder et al. (1998) "Low-Temperature Single-Crystal Si TFTs Fabricated on Si Films Processed via Sequential Lateral Solidification," *IEEE Electron. Dev. Lett.* 19:306-308.

Csutak et al. (2002) "CMOS-Compatible High-Speed Planar Silicon Photodiodes Fabricated on SOI Substrates," *IEEE Journal of Quantum Electronics.* 38:193-196.

Cui et al. (2001) "Nanowire Nanosensors for Highly Sensitive and Selective Detection of Biological and Chemical Species," *Science* 293:1289-1292.

Czekalla et al. (2008) "Spatial Fluctuations of Optical Emission from Single ZnO/MgZnO Nanowire Quantum Wells," *International Journal of Nanotechnology.* 19:115202.

Dagdeviren et al. (published online Apr. 19, 2013) "Transient, Biocompatible Electronics and Energy Harvesters Based on ZnO," *Small.* e-publication.

Dai et al. (2002) "Gallium Oxide Nanoribbons and Nanosheets," *J. Phys. Chem. B* 106(5):902-904.

Dai et al. (2003) "Novel Nanostructures of Functional Oxides Synthesized by Thermal Evaporation," *Adv. Funct. Mater.* 13:9-24.

Danckwerts (1950) "Absorption by Simultaneous Diffusion and Chemical Reaction," *Transactions of the Faraday Society.* 46:300.

Danilova et al. (2008) "Dipole Analysis of Event-Related Oscillations in Anticipation Processes," *International Journal of Psychophysiology.* 69:161-162.

David et al. (2012) "Dissolution Kinetics and Solubility of ZnO Nanoparticles Followed by AGNES," *J. Phys. Chem.* 116:11758.

Davidson et al. (2004) "Supercritical Fluid-Liquid-Solid Synthesis of Gallium Arsenide Nanowires Seeded by Alkanethiol-Stabilized Gold Nanocrystals," *Adv. Mater.* 16:646-649.

de Gans (2004) "Inkjet Printing of Polymers: State of the Art and Future Developments," *Adv. Mater.* 16(3):203-213.

De Sio et al. (Web Release May 18, 2005) "Electro-Optical Response of a Single-Crystal Diamond Ultraviolet Photoconductor in Transverse Configuration," *Appl. Phys. Lett.* 86:213504.

DeBoer et al. (2004) "Organic Single-Crystal Field-Effect Transistors," *Phys. Stat. Sol.* 201:1302-1331.

Dean et al. (2004) "Electrical Characterization of Polymer-Based FETs Fabricated by Spin-Coating Poly(3-alkylthiophene)s," *IEEE Trans. Electron Devices* 51:1892-1901.

Delmerche et al. (1997) "Stability of Molded Polydimethylsiloxane Microstructures," *Adv. Mat.* 9:741-746.

Deruelle et al. (1995) "Adhesion at the Solid-Elastomer Interface: Influence of Interfacial Chains," *Macromol.* 28:7419-7428.

Derycke et al. (Sep. 2001) "Carbon Nanotube Inter- and Intramolecular Logic Gates," *Nano Lett.* 1(9):453-456.

Desai et al. (Feb. 1999) "Nanopore Technology for Biomedical Applications," *Biomed. Microdevices* 2(1):11-40.

Dick et al. (Jun. 2004) "Synthesis of Branched 'Nanotrees' by Controlled Seeding of Multiples Branching Events," *Nat. Mater.* 3:380-384.

Dimroth et al. (Mar. 2007) "High Efficiency Multijunction Solar Cells," *MRS Bull.* 32:230-235.

Ding et al. (Oct. 4, 2004) "Self Catalysis and Phase Transformation in the Formation of CdSe Nanosaws," *Adv. Mater.* 16(19):1740-1743.

Dinsmore et al. (2002) "Colloidosomes: Selectively Permeable Capsules Composed of Colloidal Particles," *Science* 298:1006-1009.

Divliansky et al. (2003) "Fabrication of Three-Dimensional Polymer Photonic Crystal Structures Using Single Diffraction Element Interference Lithography," *Appl. Phys. Lett.* 82(11):1667-1669.

Dobrev (2000) "Use of Cutometer to Assess Epidermal Hydration," *Skin Research and Technology.* 6:239-244.

Dodabalapur A. (Apr. 2006) "Organic and Polymer Transistors for Electronics," *Mater Today* 9(4):24-30.

Dodabalapur et al. (1995) "Organic Transistors: Two-Dimensional Transport and Improved Electrical Characteristics," *Science* 268:270-271.

Duan et al. (2000) "General Synthesis of Compound Semiconductor Nanowires," *Adv. Mater.* 12(4):298-302.

Duan et al. (2003) "High-performance Thin-Film Transistors Using Semiconductor Nanowires and Nanoribbons," *Nature* 425:274-278.

Duan X, (2003) "Semiconductor Nanowires: From Nanoelectronics to Macroelectronics," Abstract from a presentation given at the 11th Foresight Conference on Molecular Nanotechnology, Oct. 10-20, Burlingame, CA.

Duboz et al. (1998) "Transistors and Detectors Based on GaN-Related Materials," In; *Group III Nitride Semiconductor Compounds*, Gill, B. ed., Clarendon, Oxford, pp. 343-387.

(56) References Cited

OTHER PUBLICATIONS

Ducéré et al. (2005) "A Capacitive Humidity Sensor Using Cross-Linked Cellulose Acetate Butyrate," *Sensors and Actuators B: Chemical.* 106:331-334.
Duesberg et al. (2000) "Polarized Raman Spectroscopy on Isolated Single-Wall Carbon Nanotubes," *Phys. Rev. Lett.*, vol. 85, No. 25, pp. 5436-5439.
Duffy et al. (1998) "Rapid Prototyping of Microfluidic Systems in Poly(dimethylsiloxane)," *Anal. Chem.* 70:4974-4984.
Dupuis et al. (2008) "History, Development, and Applications of High-Brightness Visible Light-Emitting Diodes," *IEEE J. Lightwave Tech.* 26:1154-1171.
Durkop et al. (2004) "Extraordinary Mobility in Semiconducting Carbon Nanotube," *Nano Lett.* 4(1):35-39.
Eder et al. (Apr. 5, 2004) "Organic Electronics on Paper," *Appl. Phys. Lett.* 84(14)2673-2675.
Edrington et al. (2001) "Polymer-Based Photonic Crystals," *Adv. Mater.* 13:421-425.
Efimenko et al. (Oct. 15, 2002) "Surface Modification of Sylgard-184 Poly(dimethyl Siloxane) Networks by Ultraviolet and Ultraviolet/Ozone Treatment," *J. Colloid Interface Sci.* 254(2):306-315.
Eftekhari, G. (1993) "Variation in the Effective Richardson Constant of Metal—GaAs and Metal—InP Contacta Due to the Effect of Processing Parameters," *Phys. Status Solid A—Appl. Res.* 140:189-194.
Ensell, G. (1995) "Free Standing Single-Crystal Silicon Microstructures," *J. Micromech. Microeng.* 5:1-4.
Exam Report, Written Opinion and Response to Written Opinion, Corresponding to Singapore Patent Application No. 2007/18082-1, Mailed Beginning Jan. 15, 2009.
Examination Report and Response, Corresponding to Malaysian Patent Application No. PI 20062672, Mailed Aug. 28, 2009.
Examination Report, Corresponding to European Application No. EP 05 756 327.2, Dated Jan. 20, 2010.
Examination Report, Corresponding to Malaysian Patent Application No. PI 20092343, Mailed Jun. 15, 2010.
Examination Report, Corresponding to Malaysian Patent Publication No. PI 20052553, Mailed Mar. 13, 2009.
Examination Report, Corresponding to Singapore Patent Application No. 200608359-6, Completed on Aug. 27, 2008.
Examination Report, Response and Search Report, Corresponding to Malaysian Patent Application No. PI 20062537, Nov. 20, 2009.
Faez et al. (1999) "An Elastomeric Conductor Based on Poluaniline Prepared by Mechanical Mixing," *Polymer* 40:5497-5503.
Fan et al. (2009) "Three Dimensional Nanopillar Array Photovoltaics on Low Cost and Flexible Substrates," *Nature Materials.* 8:648-653.
Felgner et al. (1996) "Flexural Rigidity of Microtubules Measured with the Use of Optical Tweezers," *J. Cell Sci.* 109:509-516.
Fink et al. (1999) "Block Copolymers as Photonic Bandgap Materials," *J. Lightwave. Tech.* 17:1963-1969.
Fink et al. (2001) "Enhancement of device performance in vertical sub-100 nm MOS devices due to local channel doping," *Solid State Electron.* 46:387.
Flewitt et al. (2005) "Low-Temperature Deposition of Hydrogenated Amorphous Silicon in an Electron Cyclotron Resonance Reactor for Flexible Displays," *Proc. IEEE* 93:1364-1373.
Fluhr et al. (1999) "Comparative Study of Five Instruments Measuring Stratum Corneum Hydration (Corneometer CM 820 and CM 825, Skicon 200, Nova DPM 9003, DermaLab). Part I. In vitro," *Skin Research and Technology.* 5:161-170.
Fluhr et al. (1999) "Comparative study of five instruments measuring stratum corneum hydration," *Skin Res. Technol.* 5:171-178.
Folch et al. (1999) "Wafer-Level In-Registry Microstamping," *J. Microelectromech. Syst.* 8:85-89.
Forment et al. (2004) "Influence of Hydrogen Treatment and Annealing Processes Upon the Schottky Barrier Height of Au/n-GaAs and Ti/n-GaAs Diodes," *Semicond. Sci. Technol.* 19:1391-1396.

Forrest et al. (2004) "The Path to Ubiquitous and Low-Cost Organic Electronic Appliances on Plastic," *Nature* 428:911-918.
Fortunato et al. (2005) "Flexible a-Si: H Position-Sensitive Detectors," *Proc. IEEE* 93:1281-1286.
Fortunato et al. (Sep. 2008) "High-Performance Flexible Hybrid Field-Effect Transistors Based on Cellulose Fiber Paper," *IEEE Electron. Dev. Lett.* 29(9):988-990.
Fox et al. (1976) "Transcutaneous Electrical Stimulation and Acupuncture: Comparison of Treatment for Low-Back Pain," *Pain.* 2:141-148.
Freeman et al. (2000) "Spatial Spectral Analysis of Human Electrocardiograms Including the Alpha and Gamma Bands," *J. Neurosci. Methods* 95:111-121.
Freire et al. (1999) "Thermal Stability of Polyethylene Terephthalate (PET): Oligomer Distribution and Formation of Volatiles," *Packag. Technol. Sci.* 12:29-36.
Freund, L.B. (2000) "The Mechanics of Electronic Materials," *Int. J. Solids Struct.* 37:185-196.
Friedman et al. (2005) "High-Speed Integrated Nanowire Circuits," *Nature* 434:1085.
Frodin et al. (1988) "Hydration of Human Stratum Corneum Studied In Vivo by Optothermal Infrared Spectrometry, Electrical Capacitance Measurement, and Evaporimetry," *Acta Derm Venereol.* 68:461-7.
Fu et al. (Jan. 10, 2003) "Patterning of Diamond Microstructures on Si Substrate by Bulk and Surface Micromachining," *J. Mater. Process. Technol.* 132(1-3):73-81.
Fulati et al. (2009) "Miniaturized pH Sensors Based on Zinc Oxide Nanotubes/Nanorods," *Sensors.* 9:8911-8923.
Furneaux et al. (1989) "The Formation of Controlled-Porosity Membranes from Anodically Oxidized Aluminum," *Nature* 337:147-149.
Gabriel et al. (1996) "The dielectric properties of biological tissues: I. Literature survey," *Phys. Med. Biol.* 41:2231-2249.
Gabriel et al. (2009) "Electrical conductivity of tissue at frequencies below 1 MHz," *Phys. Med. Biol.* 54:4863-4878.
Gan et al. (2002) "Preparation of Thin-Film Transostros With Chemical Bath Deposited CdSe and CdS Thin Films," *IEEE Trans. Electron. Dev.* 49:15-18.
Gao et al. (Sep. 9, 2005) "Conversion of Zinc Oxide Nanobelts into Superlattice-Structures Nanohelices," *Science* 309:1700-1704.
Garcia et al. (2004) "Etchant Anisotropy Controls the Step Bunching Instability in KOH Etching of Silicon," *Phys. Rev. Lett.* 93(16):166102.
Gardner et al. (1965) "Physical Aspects of the Internal Water Relations of Plant Leaves," *Plant Physiol.* 40:705-710.
Garnier et al. (1994) "All-Polymer Field-Effect Transistor Realized by Printing Techniques," *Science* 265:1684-1686.
Geerligs et al. (2011) "In Vivo Indentation to Determine the Mechanical Properties of Epidermis," *J. Biomech.* 44:1176-1181.
Geim et al. (Mar. 2007) "The Rise of Graphene," *Nature Mater.* 6:183-191.
Geissler et al. (2003) "Fabrication of Metal Nanowires Using Microcontact Printing," *Langmuir* 19(15):6301-6311.
Geissler et al. (Jun. 2003) "Selective Wet-Etching of Microcontact-Printed Cu Substrates with Control Over the Etch Profile," *Microelec. Eng.* 67-68:326-332.
Gelinck et al. (2000) "High-Performance All-Polymer Integrated Circuits," *Appl. Phys. Lett.* 77:1487-1489.
Gelinck et al. (2004) "Fleible Active-Matrix Displays and Shift Registers Based on Solution-Processed Organic Transistors," *Nat. Mater.* 3:106-110.
Georgakilas et al. (2002) "Wafer-Scale Integration of GaAs Optoelectronic Devices with Standard Si Integrated Circuits Using a Low-Temperature Bonding Procedure," *Appl. Phys. Lett.* 81:5099-5101.
Gerhardt et al. (2008) "Influence of epidermal hydration on the friction of human skin against textiles," *J. R. Soc. Interface* 5:1317-1328.
Gerischer et al. (1992) "Chemical dissolution of zinc oxide crystals in aqueous electrolytes—An analysis of the kinetics," *Electrochimica Acta.* 37:827.

(56) References Cited

OTHER PUBLICATIONS

Givargizov, E.I. (1991) "Applications" In; *Oriented Crystallization on Amorphous Substrates*, Plenum Press, New York, pp. 341-363.
Goetting et al. (1999) "Microcontact Printing of Alkanephosphonic Acids on Aluminum: Pattern Transfer by Wet Chemical Etching," *Langmuir* 15:1182-1191.
Goldman et al. (1996) "Correlation of Buffer Strain Relaxation Modes with Transport Properties of Two-Dimensional Electron Gases," *J. Apple. Phys.* 80:6849-6854.
Goldmann et al. (2004) "Hole Mobility in Organic Single Crystals Measured by a "Flip-Crystal" Field-Effect Technique," *J. Appl. Phys.* 96:2080-2086.
Goldsmith, T.H. (Sep. 1990) "Optimization, Constraint, and History in the Evolution of Eyes," *Quart. Rev. Biol.* 65(3):281-322.
Gonzalez et al. (2008) "Design of Metal Interconnects for Stretchable Electronic Circuits," *Microelectronics Reliability.* 48:825-832.
Gratz et al. (1991) "Atomic Force Microscopy of Atomic-Scale Ledges and Etch Pits Formed During Dissolution of Quartz," *Science*, 251:1343-1346.
Gray et al. (Dec. 2001) "Screen Printed Organic Thin Film Transistors (OTFTs) on a Flexible Substrate," *Proc. SPIE* 4466:89-94.
Gray et al. (Mar. 5, 2004) "High-Conductivity Elastomeric Electronics," *Adv. Mater.* 16(5):393-397.
Grayson, T. (2002) "Curved Focal Plane Wide Field of View Telescope Design," *Proc. SPIE* 4849:269-274.
Griss et al. (2002) "Characterization of Micromachined Spiked Biopotential Electrodes," *IEEE Trans. Biomed. Eng.* 49:597-604.
Grosjean et al. (2006) "Hydrolysis of Mg-salt and MgH2-Salt Mixtures Prepared by Ball Milling for Hydrogen Production," *Journal of Alloys and Compounds.* 416:296.
Gruen et al. (Mar. 21, 1994) "Fullerenes as Precursors for Diamond Film Growth Without Hydrogen or Oxygen Additions," *Appl. Phys. Lett.* 65(12):1502-1504.
Gudiksen et al. (Web Release Apr. 18, 2001) "Synthetic Control of the Diameter and Length of Single Crystal Semiconductor Nanowires," *J. Phys. Chem. B* 105:4062-4064.
Guimerà et al. (2008) "Method and Device for Bio-Impedance Measurement with Hard-Tissue Applications," *Physiological Measurement.* 29:S279.
Gullapalli et al. (2010) "Flexible Piezoelectric ZnO-Paper Nanocomposite Strain Sensor," *Small.* 6:1641.
Guo et al. (Aug. 19, 2002) "Metal-Insulator-Semiconductor Electrostatics of Carbon Nanotubes," *Appl. Phys. Lett.* 81(8):1486-1488.
Gupta et al. (2010) "Development of Gas Sensors Using ZnO Nanostructures," *J. Chem. Sci.* 122:57.
Gur et al. (2005) "Air-Stable All-Inorganic Nanocrystal Solar Cells Processed from Solution," *Science* 310:462-465.
Gurbuz et al. (Jul. 2005) "Diamond Semiconductor Technology for RF Device Applications." *Solid State Electron.* 49(7):1055-1070.
Haisma et al. (2002) "Contact Bonding, Including Direct-Bonding in a Historical and Recent Context of Materials Science and Technology, Physics and Chemistry," *Mater. Sci Eng.* 37:1-60.
Halik et al. (2004) "Low-Voltage Organic Transistors with an Amorphous Molecular Gate Dielectric," *Nature* 431:963-966.
Hamed et al. (Dec. 2012) "Construction, In Vitro and In Vivo Evaluation of an In-House Conductance Meter for Measurement of Skin Hydration," *Medical Engineering & Physics.* 34:1471-1476.
Hamedi et al. (May 2007) "Towards Woven Logic from Organic Electronic Fibres," *Nat. Mater.* 6:357-362.
Hamilton et al. (2004) "Field-Effect Mobility of Organic Polymer Thin-Film Transistors," *Chem. Mater.* 16:4699-4704.
Han et al. (2005) "Template-Free Directional Growth of Single-Walled Carbon Nanotues on a- and r-Plane Sapphire," *J. Am. Chem. Soc.* 127:5294-5295.
Harada et al. (2001) "Catalytic Amplification of the Soft Lithographic Patterning of Si. Nonelectrochemical Orthogonal Fabrication of Photoluminescent Porous Si Pixel Arrays," *J. Am. Chem. Soc.* 123:8709-8717.
Hardyck et al. (1966) "Feedback of Speech Muscle Activity During Silent Reading: Rapid Extinction," *Science.* 154:1467-1468.

Harkonen et al. (Jun. 8, 2006) "4 W Single-Transverse Mode VECSEL Utilizing Intra-Cavity Cavity Diamond Heat Spreader," *Electron Lett.* 42(12):693-694.
Hayase et al. (2001) "Photoangioplasty with Local Motexafin Lutetium Delivery Reduces Macrophages in a Rabbit Post-Balloon Injury Model," *Cardiovascular Res.* 49:449-455.
He et al. (2005) "Si Nanowire Bridges in Microtrenches: Integration of Growth into Device Fabrication," *Adv. Mater.* 17:2098-2102.
Heffelfinger et al. (1997) "Steps and the structure of the (0001) α-alumina surface," *Surf. Sci.*, 370:L168-L172.
Hejjel (2004) "Suppression of power-line interference by analog notch filtering in the ECG signal for heart rate variability analysis: to do or not to do?" *Med. Sci. Monit.* 10:MT6-MT13.
Hendriks, et al. (2004) "Influence of Hydration and Experimental Length Scale on the Mechanical Response of Human Skin In Vivo, Using Optical Coherence Tomography," *Skin Research and Technology.* 10: 231-241.
Hillbrog et al. (Web Release Dec. 30, 2003) "Nanoscale Hydrophobic Recovery: A Chemical Force Microscopy Study of UV/Ozone-Treated Cross-Linker Poly(dimethylsiloxane)," *Langmuir* 20(3):785-794.
Hines et al. (2005) "Nanotransfer Printing of Organic and Carbon Nanotube Thin-Film Transistors on Plastic Substrates," *Appl. Phys. Lett.* 86:163101.
Hoffman et al. (2003) "ZnO-Based Transparent Thin-Film Transistors," *Appl. Phys. Lett.* 82:733.
Hoffmann et al. (2007) "Flexible dry surface-electrodes for ECG long-term monitoring," *IEEE EMBS.* pp. 5739-5742.
Hollenberg et al. (2006) "A MEMS Fabricated Flexible Electrode Array for Recording Surface Field Potentials," *J. Neurosci. Methods* 153:147-153.
Holmes et al. (Feb. 25, 2000) "Control of Thickness and Orientation of Solution-Grown Silicon Nanowires," *Science* 287:1471-1473.
Horan et al. (Jun. 2005) "In Vitro Degradation of Silk Fibroin," *Biomaterials* 26(17):3385-3393.
Horn et al. (1992) "Contact Electrification and Adhesion Between Dissimilar Materials," *Science* 256:362-364.
Hoyer, P. (1996) "Semiconductor Nanotube Formation by a Two-Step Template Process," *Adv. Mater.* 8:857-859.
Hsia et al. (2005) "Collapse of Stamps for Soft Lithography Due to Interfacial Adhesion," *Appl. Phys. Lett.* 86:154106.
Hsu et al. (2002) "Amorphous Si TFTs on Plastically Deformed Spherical Domes," *J. Non-Crystalline Solids* 299-302:1355-1359.
Hsu et al. (2003) "Nature of Electrical Contacts in a Metal-Molecule-Semiconductor System," *J. Vac. Sci. Technol. B* 21(4):1928-1935.
Hsu et al. (Jan. 15, 2004) "Spherical Deformation of Compliant Substrates with Semiconductor Device Islands," *J. Appl. Phys.* 95(2):705-712.
Hsu et al. (Mar. 2004) "Effects of Mechanical Strain on TFT's on Spherical Domes," *IEEE Trans. Electron Dev.* 51(3):371-377.
Hu et al. (1997) "Using Soft Lithography to Fabricate GaAs/AlGaAs Heterostructure Field Effect Transistors," *Appl. Phys. Lett.* 71:2020-2022.
Hu et al. (1999) Chemistry and Physics in One Dimension: Synthesis and Properties of Nanowires and Nanotubes, *Acc. Chem. Res.* 32:435-445.
Hu et al. (2004) "Percolation in Transparent and Conducting Carbon Nanotube Networks," *Nano Lett.*, vol. 4, No. 12, pp. 2513-2517.
Hu et al. (2009) "Highly Conductive Paper for Energy-Storage Devices," *Proc. Natl. Acad. Sci. USA* 106:21490-21494.
Hu et al. (2010) "Stretchable, Porous, and Conductive Energy Textiles," *Nano Lett.* 10:708-714.
Hua et al. (1993) "Finite Element Modeling of Electrode-Skin Contact Impedance in Electrical Impedance Tomography," *IEEE Transactions on Biomedical Engineering.* 40:335-343.
Huang et al. (2001) "Directed Assembly of One-Dimensional Nanostructures into Functional Networks," *Science* 291:630-633.
Huang et al. (2001) "Room-Temperature Ultraviolet Nanowire Nanolasers," *Science* 292:1897-1899.
Huang et al. (2003) "Growth of Millimeter-Long and Horizontally Aligned Single-Walled Carbon Nanotubes on Flat Substrates," *J. Am. Chem. Soc.*, 125:5636-5637.

(56) References Cited

OTHER PUBLICATIONS

Huang et al. (2004) "Long and Oriented Single-Walled Carbon Nanotubes Grown by Ethanol Chemical Vapor Deposition," *J. Phys. Chem. B.* 108:16451-16456.
Huang et al. (2004) "Self-Organizing High-Density Single-Walled Carbon Nanotube Arrays from Surfactant Suspensions," *Nanotechnol.* 15:1450-1454.
Huang et al. (2005) "Nanomechanical Architecture of Strained Bilayer Thin Films: From Design Principles to Experimental Fabrication," *Adv. Mater.* 17(23):2860-2864.
Huang et al. (2005) "Nanowires for Integrated Multicolor Nanophotonics," *Small* 1(1):142-147.
Huang et al. (2005) "Nonlinear Analyses of Wrinkles in a Film Bonded to a Compliant Substrate," *J. Mech. Phys. Solids* 53:2101-2118.
Huang et al. (2005) "Stamp Collapse in Soft Lithography," *Langmuir* 21:8058-8068.
Huang et al. (2011) "A Flexible pH Sensor Based on the Iridium Oxide Sensing Film," *Sensors and Actuators A: Physical.* 169:1-11.
Huang et al. (Dec. 2012) "Epidermal Differential Impedance Sensor for Conformal Skin Hydration Monitoring," *Biointerphases.* 7:52.
Huang et al. (Jan. 16, 2001) "Catalytic Growth of Zinc Oxide Nanowires by Vapor Transport," *Adv. Mater.* 13(2):113-116.
Huck et al. (2000) "Ordering of Spontaneously Formed Buckles on Planar Surfaces," *Langmuir* 16:3497-3501.
Hudson et al. (2008) "The Biocompatibility of Mesoporous Silicates," *Biomaterials.* 29:4045.
Huie, J.C. (2003) "Guided Molecular Self Assembly: A review of Recent Efforts," *Smart Mater. Struct.* 12:264-271.
Huitema et al. (2001) "Plastic Transistors in Active-Matrix Displays," *Nature* 414:599.
Hur et al. (2005) "Printed thin-film transistors and complementary logic gates that use polymer-coated single-walled carbon nanotube networks," *J. Appl. Phys.*, 98, 114302.
Hur et al. (205) "Organic Nanodelectrics for Low Voltage Carbon Nanotube Thin Film Transistors and Complementary Logc Gates," *J. Am. Chem. Soc.* 127:13808-13809.
Hur et al. (Dec. 2004) "Nanotransfer Printing by Use of Noncovalent Surface Forces: Applications to Thin-Film Transistors that Use Single-Walled Carbon Nanotube Networks and Semiconducting Polymers," *Appl. Phys. Lett.* 85(23):5730-5732.
Hur etal. (Jun. 13, 2005) "Extreme Bendability of Single Walled Carbon Nanotube Networks Transferred From High-Temperature Growth Substrates to Plastic and Their Use in Thin-Film Transistors," *Appl. Phys. Lett.* 243502.
Hutchinson et al. (1992) "Mixed Mode Cracking in Layered Materials," *Adv. Appl. Mech.* 29:63-191.
Hwang et al. (2012) "A Physically Transient Form of Silicon Electronics," *Science.* 337:1640.
Ilican et al. (2008) "Preparation and Characterization of ZnO Thin Films Deposited by Sol-Gel Coating Method," *Journal of Optoelectronics and Advanced Materials.* 10:2578.
Imparato et al. (2005) "Excimer Laser Induced Crystallization of Amorphous Silicon on Flexible Polymer Substrates," *Thin Solid Films* 487:58-62.
International Search Report and Written Opinion corresponding to International Patent Application No. PCT/US2013/034667, mailed Aug. 19, 2013.
International Search Report and Written Opinion, Corresponding to International Application No. PCT/US10/50468, Mailed Jan. 6, 2011.
International Search Report and Written Opinion, Corresponding to International Application No. PCT/US10/60425, Mailed May 25, 2011.
International Search Report and Written Opinion, Corresponding to International Application No. PCT/2005/014449, Mailed Jul. 3, 2008.
International Search Report and Written Opinion, Corresponding to International Application No. PCT/US04/40192, Mailed Jul. 6, 2005.
International Search Report and Written Opinion, Corresponding to International Application No. PCT/US07/74293, Mailed Jul. 24, 2008.
International Search Report and Written Opinion, Corresponding to International Application No. PCT/US07/77217, Mailed Jun. 3, 2008.
International Search Report and Written Opinion, Corresponding to International Application No. PCT/US07/82633, Mailed May 16, 2008.
International Search Report and Written Opinion, Corresponding to International Application No. PCT/US09/47442, Mailed Sep. 21, 2009.
International Search Report and Written Opinion, Corresponding to International Application No. PCT/US2006/032125, Mailed Mar. 21, 2008.
International Search Report and Written Opinion, Corresponding to International Application No. PCT/US2009/036192, Mailed Jul. 6, 2009.
International Search Report and Written Opinion, Corresponding to International Application No. PCT/US2009/058231, Mailed Nov. 17, 2009.
International Search Report and Written Opinion, Corresponding to International Application No. PCT/US2010/034520, Mailed Sep. 24, 2010.
International Search Report and Written Opinion, Corresponding to International Application No. PCT/US2010/042585, Mailed May 25, 2011.
International Search Report and Written Opinion, Corresponding to International Application No. PCT/US2011/028094, Mailed Jul. 14, 2011.
International Search Report and Written Opinion, Corresponding to International PCT Application No. PCT/US05/19354, Dated Apr. 18, 2007.
International Search Report and Written Opinion, Corresponding to International PCT Application No. PCT/US2006/021161, Mailed Feb. 28, 2008.
International Search Report and Written Opinion, Corresponding to International PCT Application No. PCT/US2007/022959, Mailed Oct. 14, 2008.
International Search Report and Written Opinion, Corresponding to International PCT Application No. PCT/US2007/077759, Mailed Apr. 11, 2008.
International Search Report and Written Opinion, Corresponding to International PCT Application No. PCT/US2007/079070, Mailed Apr. 23, 2008.
Irimia-Vladu (2010) "Biocompatible and Biodegradable Materials for Organic Field-Effect Effect Transistors," *Adv. Funct. Mater.* 20:4069.
Isberg et al. (Sep. 6, 2002) "High Carrier Mobility in Single-Crystal Plasma-Deposited Diamond," *Science* 297:1670-1672.
Islam et al. (Jan. 16, 2003) "High Weight Fraction Surfactant Solubilization of Single-Wall Wall Carbon Nanotubes in Water," *Nano Lett.* 3(2):269-273.
Ismach et al. (2004) "Atomic-Step-Templated Formation of Single Wall Carbon Nanotube Patters," *Angew. Chem. Int. Ed.* 43:6140-6143.
Itoh et al. (1991) "Cathodoluminescence Properties of Undoped and Zn-Doped $Al_xGa_{1-x}N$ Grown by Metaloganic Vapor Phase Epitaxy," *Jap. J. Appl. Phys.* 30:1604-1608.
Ives et al. (2007) "Miniaturized, On-Head, Invasive Electrode Connector Integrated EEG Data Acquisition System," *Clinical Neurophysiol.* 118:1633-1638.
J. Vanfleteren. SWEET: Stretchable and Washable Electronics for Embedding Textiles. Available at ftp://ftp.cordis.europa.eu/pub/ist/docs/mnd/ws-sfit_en.pdf.Accessed Feb. 8, 2012.
Jabbour et al. (2001) "Screen Printing for the Fabrication of Organic Light-Emitting Devices," *IEEE J. Select. Top. Quantum. Electron.* 7:769-773.
Jackman et al. (Aug. 4, 1995) "Fabrication of Submicrometer Features on Curved Substrates by Microcontact Printing," *Science* 269:664-666.
Jacobs et al. (2001) "Submicrometer Patterning of Charge in Thin-Film Electrets," *Science* 291:1763-1766.

(56) References Cited

OTHER PUBLICATIONS

Jacobs et al. (2002) "Fabrication of a Cylindrical Display by Patterned Assembly," *Science* 296:323-325.
Jain et al. (2000) "III-Nitrides: Growth, Characterization, and Properties," *J. Appl. Phys.* 87:965-1006.
Jain et al. (2005) "Flexible Electronics and Displays: High-Resolution, Roll-to-Roll, Projection Lithography and Photoblation processing Technologies for Hiogh-Throughput Production," *Proc. IEEE* 93:1500-1510.
James et al. (1998) "Patterned Protein Layers on Solid Substrates by This Stamp Microcontact Printing," *Langmuir* 14:742-744.
Jang et al. (2003) "Lateral Growth of Aligned Multiwalled Carbon Nanotubes Under Electric Fiels," *Solid State Commun.* 126:305-308.
Jang et al. (2006) "Low-Voltage and High-Field-Effect Mobility Organic Transistors with a Polymer Insulator," *Appl. Phys. Lett.* 88:072101.
Javey et al. (2002) "High-κ Dielectrics for Advanced Carbon-Nanotube Transistors and Logic Gates," *Nature Mater.* 1:241-246.
Javey et al. (2005) "High Performance n-Type Carbon Nanotube Field-Effect Transistors with Chemically Doped Contacts," *Nano Lett.*, vol. 5, No. 2, pp. 345-348.
Javey et al. (Aug. 7, 2003) "Ballistic Carbon Nanotube Field-Effect Transistors," *Nature* 424:654-657.
Jenkins et al. (1994) "Gallium Arsenide Transistors: Realization Through a Molecularly Designs Insulator," *Science* 263:1751-1753.
Jeon et al. (1995) "Patterning of Dielectric Oxide Thin Layers by Microcontact Printing of Self-Assembled Monolayers," *J. Mater. Res.* 10:2996-2999.
Jeon et al. (2003) "Structural and Mechanical Properties of Woven Fabrics Employing Peirce's Model," *Textile Res. J.* 73:929-933.
Jeon et al. (2004) "Fabricating Complex Three-Dimensional Nanostructures with High Resolution Conformable Phase Masks," *Proc. Natl. Acad. Sci. USA* 101:12428-12433.
Jeon et al. (2007) "Low-Voltage Zinc-Oxide Thin-Film Transistors on a Conventional $SiO_2$ Gate Insulator Grown by Radio-Frequency Magnetron Sputtering at Room Temperature," *J. of the Korean Physical Society* 51:1999.
Jeon et al. (Aug. 4, 2004) "Three Dimensional Nanofabrication with Rubber Stamps and Conformable Photomasks," *Adv. Mater.* 16(15):1369-1375.
Jiang et a. (Oct. 2, 2007) "Finite Deformation Mechanics in Buckled Thin Films on Compliant Supports," *Proc. Natl. Acad. Sci. USA* 104(40):15607-15612.
Jiang et al. (1999) "Preparation of Macroporous Metal Films from Colloidal Crystals," *J. Am. Chem. Soc.* 121:7957-7958.
Jiang et al. (2002) "Polymer-on-Polymer Stamping: Universal Approaches to Chemically Patterned Surfaces," *Langmuir* 18:2607-2615.
Jiang et al. (2007) "Mechanical Properties of Robust Ultrathin Silk Fibroin Films," *Adv. Funct. Mater.* 17:2229-2237.
Jiang et al. (2008) "Post-Buckling Analysis for the Precisely Controlled Buckling of Thin Film Encapsulated by Elastomeric Substrates," *Int. J. Solids Struct.* 45, 2014-2023.
Jin et al. (2004) "Scalable Interconnection and Integration of Nanowire Devices Without Registration," *Nano Lett.* 4:915-919.
Jin et al. (2004) "Soft Lithographic Fabrication of an Image Sensor Array on a Curved Substrate," *J. Vac. Sci. Technol. B* 22(5):2548-2551.
Jin et al. (Aug. 2005) "Water-Stable Silk Films with Reduced β-Sheet Content," *Adv. Funct. Mater.* 15(8):1241-1247.
Jin et al. (Web Release Jan. 23, 2004) "Biomaterial Films of *Bombyx mori* Silk Fibroin with Poly(ethylene oxide)," *Biomacromolecules* 5(3):711-717.
Jiyun, C.H. (2003) "Guided Molecular Self-Assembly: A Review of Recent Efforts," *Smart Mater. Struct.* 12:264-271.
Joachim et al. (Nov. 30, 2000) "Electronics Using Hybrid-Molecular and Mono-Molecular Molecular Devices," *Nature* 408:541-548.
Johnson et al. (1999) "Ordered Mesoporous Polymers of Tunable Pore Size from Colloidal Silica Templates," *Science* 283:963-965.
Jones (2008) Tactile Displays: Guidance for Their Design and Application,: *Human Factors.* 50:90-111.
Jones et al. (Jul./Aug. 2004) "Stretchable Wavy Metal Interconnects," *J. Vac. Sci. Technol. A* 22(4):1723-1725.
Joo et al. (2006) "Low-Temperature Solution-Phase Synthesis of Quantum Well Structures CdSe Nanoribbons," *J. Am. Chem. Soc.* 128(17):5632-5633.
Jortner et al. (2002) "Nanostructured Advanced Materials Perspectives and Directions," *Pure Appl. Chem.* 74(9):1491-1506.
Joselevich (2002) "Vectorial Growth of Metallic and Semiconducting Single-Wall Carbon Nanotubes," *Nano Lett.*, vol. 2, No. 10, pp. 1137-1141.
Jung et al. (2012) "CNT/PDMS composite flexible dry electrodes for long-term ECG monitoring," *IEEE T. Bio-Med. Eng.* 59:1472.
Kaczmarek et al. (1991) "Electrotactile and Vibrotactile Displays for Sensory Substitution Systems," *IEEE Transactions on Biomedical Engineering.* 38:1-16.
Kaczmarek et al. (2003) "Pattern Identification and Perceived Stimulus Quality as a Function of Stimulation Waveform on a Fingertip-Scanned Electrotactile Display," *IEEE Transactions on Neural Systems and Rehabilitation Engineering.* 11:9-16.
Kadish et al. (1988) "Interaction of Fiber Orientation and Direction of Impulse Propagation with Anatomic Barriers in Anisotropic Canine Myocardium," *Circulation.* 78:1478-1494.
Kadlec et al. (2008) "Assessing Skin Hydration Status in Haemodialysis Patients Using Terahertz Spectroscopy: A Pilot/Feasibility Study," *Physics in Medicine and Biology.* 53:7063.
Kagan (1999) "Organic-Inorganic Hybrid Materials as Semiconducting Channels in Thin-Film Field-Effect Transistors," *Science* 286:945-947.
Kagan et al. (2001) "Patterning Organic—Inorganic Thin-Film Transistors Using Microcontact Printed Templates," *Appl. Phys Lett.* 79(21):3536-3538.
Kagan et al. (2003) *Thin Film Transistors*, Dekker, New York, pp. 1-34.
Kane et al. (2000) "Analog and Digital Circuits Using Organic Thin-Film Transistors on Polyester Substrates," *IEEE Electron. Dev. Lett.* 21:534-536.
Kaneko et al. (2005) "The Influence of Age on Pressure Perception of Static and Moving Two-Point Discrimination in Normal Subjects," *J. Hand Ther.* 18:421-424.
Kang et al. (2007) "Printed Multilayer Superstructures of Aligned Single-Walled Carbon Nanotubes for Electronic Applications," *Nano Lett.* 7(11):3343-3348.
Kang et al. (Apr. 2007) "High-Performance Electronics Using Dnese, Perfectly aligned Arrays of Single-Walled Carbon Nanotubes," *Nat. Nanotechnol.* 2(4):230-236.
Kar et al. (2005) "Controlled Synthesis and Photoluminescence Properties of ZnS Nanowires and Nanoribbons," *J. Phys. Chem. B* 109(8):3298-3302.
Kar et al. (2005) "Synthesis and Optical Properties of CdS Nanoribbons," *J. Phys. Chem B.* 109(41):19134-19138.
Kar et al. (2006) "Shape Selective Growth of CdS One-Dimensional Nanostructures by a Thermal Evaporation Process," *J. Phys. Chem. B.* 110(10):4542-4547.
Karnik et al. (2003) "Lateral Polysilicon $p^+$-$p$-$n^+$ and $p^+$-$n$-$n^+$ Diodes," *Solid-State Electronics* 47:653-659.
Karnik et al. (2003) "Multiple Lateral Polysilicon Diodes as Temperature Sensors for Chemical Microreaction Systems," *Jpn. J. Appl. Phys.* 42:1200-1205.
Kato et al. (2004) "The Characteristic Improvement of Si(111) Metal-Oxide-Semiconductor Field-Effect Transistor by Long-Time Hydrogen Annealing," *Jpn. J. Appl. Phys.* 43(10):6848-6853.
Katz et al. (2001) "Synthetic Chemistry for Ultrapure, Processable, and High-Mobility Organic Transistor Semiconductors," *Acc. Chem. Res.* 34:359-369.
Katz, H.E. (2004) "Recent Advances in Semiconductor Performance and Printing Processes for Organic Transistor-Based Electronics," *Chem. Mater.* 16:4748-4756.
Kawata et al. (2001) "Finer Features for Functional Microdevices," *Nature* 412:697-698.

(56) References Cited

OTHER PUBLICATIONS

Kellis et al. (2009) "Human Neocortical Electrical Activity Recorded on Nonpenetrating Microwire Arrays: Applicability for Neuroprostheses," *Neurosurg. Focus* 27(1):E9.
Kendall, D.L. (1979) "Vertical Etching of Silicon at Very High Apect Ratios," *Ann. Rev. Mater. Sci.* 9:373-403.
Keplinger et al. (2010) "Röntgen's Electrode-Free Elastomer Actuators without Electromechanical Pull-In Instability," *Proc. Natl. Acad. Sci. USA.* 107:4505-4510.
Khakani et al. (2006) "Lateral Growth of Single Wall Carbon Nanotubes on Various Substrates by Means of an 'All-Laser' Synthesis Approach," *Diamond Relat. Mater.* 15:1064-1069.
Khan et al. (1993) "High Electron Mobility Transistor Based on a GaN—Al$_x$Ga$_{1-x}$N Heterojunction," *Appl. Phys. Lett.* 63:1214-1215.
Khang et al. (2006) "A Stretchable Form of Single-Crystal Silicon for High-Performance Electronics on Rubber Substraights," *Science* 311:208-212.
Kilby, J.S. (1976) "Invention of the Integrated Circuit," *IEEE Trans. Electron. Dev.* 23:648-654.
Kim et al. (2000) "Field Emission from Carbon Nanotubes for Displays," *Diamond and Related Mater.* 9(3-6):1184-1189.
Kim et al. (2002) "Nanolithography Based on Patterned Metal Transfer and Its Application to Organic Electronic Devices," *Appl. Phys. Lett.* 80:4051-4053.
Kim et al. (2003) "Epitaxial Self-Assembly of Block Copolymers on Lithographically Defined Nanopatterned Substrates," *Nature* 424:411-414.
Kim et al. (2008) "Stretchable and foldable silicon integrated circuits," *Science.* 320(5875):507.
Kim et al. (2008) "Stretchable Electronics: Materials Strategies and Devices," *Adv. Mater.* 20:4887-4892.
Kim et al. (2009) "Integrated Wireless Neural Interface Based on the Utah Electrode array," *Biomed. Microdevices* 11:453-466.
Kim et al. (2009) "Optimized Structural Designs for Stretchable Silicon Integrated Circuits," *Small* 5(24):2841-2847.
Kim et al. (2010) "Stretchable, Curvilinear Electronics Based on Inorganic Materials," *Advanced Materials.* 22:2108-2124.
Kim et al. (2011) "Epidermal Electronics," *Science.* 333(6044):838-843.
Kim et al. (2011) "Materials for Multifunctional Balloon Catheters With Capabilities in Cardiac Electrophysiological Mapping and Ablation Therapy," *Nat. Mater.* 10:316.
Kim et al. (Dec. 2, 2008) "Materials and Noncoplanar Mesh Designs for Integrated Circuits with Linear Elastic Responses to Extreme Mechanical Deformations," *Proc. Natl. Acad. Sci. USA* 105(48):18675-18680.
Kim et al. (Jan. 2008) "Complementary Logic Gates and Ring Oscillators Plastic Substrates by Use of Printed Ribbons Single-Crystalline Silicon," *IEEE Electron. Dev. Lett.* 29(1):73-76.
Kim et al. (May 2013) "Deterministic Assembly of Releasable Single Crystal Silicon-Metal Oxide Field-Effect Devices Formed From Bulk Wafers," *Applied Physics Letters.* 102:182104.
Kim et al. (Nov. 15, 1999) "Direct Observation of Electron Emission Site on Boron-Doped Polycrystalline Diamond Thin Films Using an Ultra-High-Vacuum Scanning Tunneling Microscope," *Appl. Phys. Lett.* 75(20):3219-3221.
Kim et al. (Oct. 17, 2010) "Waterproof AllnGaP optoelectronics on stretchable substrates with applications in biomedicine and robotics," *Nature Materials* 9:929-937.
Kim et al. (Oct. 2004) "Organic TFT Array on a Paper Substrate," *IEEE Electron. Dev. Lett.* 25(10):702-704.
Kim et al. (Web Release Apr. 18, 2010) "Dissolvable Films of Silk Fibroin for Ultrathin Conformal Bio-Integrated Electronics," *Nature Materials* 9:511-517.
Kim et al. (Web Release Feb. 29, 2008) "Highly Emissive Self-Assembled Organic Nanoparticles Having Dual Color Capacity for Targeted Immunofluorescence Labeling," *Adv. Mater.* 20(6):1117-1121.
Kim et al. (Web Release Jul. 31, 2008) "Complementary Metal Oxide Silicon Integrated Circuits Incorporating Monolithically Integrated Stretchable Wavy Interconnects," *Appl. Phys. Lett.* 93(4):044102.
Kim et al. (Web Release Jul. 6, 2009) "Ultrathin Silicon Circuits with Strain-Isolation Layers and Mesh Layouts for High-Performance Electronics on Fabric, Vinyl, Leather and Paper," *Adv. Mater.* 21(36):3703-3707.
Kim et al. (Web Release Sep. 29, 2009) "Silicon Electronics on Silk as a Path to Bioresorbable, Implantable Devices," *Appl. Phys. Lett.* 95:133701-133703.
Kim, Y.S. (Web Release Aug. 9, 2005) "Microheater—Integrated Single Gas Sensor Array Chip Fabricated on Flexible Polyimide Substrate," *Sens. Actuators B* 114(1):410-417.
Klauk et al. (2002) "High-Mobility Polymer Gate Dielectric Pentacene Thin Film Transistors," *J. Appl. Phys.* 92:5259-5263.
Kleiner (1999) "Water: An Essential But Overlooked Nutrient," *Journal of the American Dietetic Association.* 99:200-206.
Klein-Wiele et al. (2003) "Fabrication of Periodic Nanostructures by Phase-Controlled Controlled Multiple-Beam Interference," *Appl. Phys. Lett.* 83(23):4707-4709.
Klode et al. (2011) "Investigation of Adhesion of Modern Wound Dressings: A Comparative Analysis of 56 Different Wound Dressings," *J. Eur. Acad. Dermatol.* 25(8):933-939.
Knipp et al. (2003) "Pentacine Thin Film Transistors on Inorganic Dielectrics: Morphology, Structural Properties, and Electronic Transport," *Appl. Phys. Lett.* 93:347-355.
Knuesel et al. (2010) "Self-assembly of microscopic chiplets at a liquid-liquid-solid interface forming a flexible segmented monocrystalline solar cell," *Proc. Natl. Acad. Sci. USA* 107:993-998.
Ko et al. (2006) "Bulk Quantities of Single-Crystal Silicon Micro-/Nanoribbons Generated from Bulk Wafers," *Nano Lett.* 6(10):2318-2324.
Ko et al. (2010) "Flexible Carbon Nanofiber Connectors with Anisotropic Adhesion Properties," *Small* 6:22-26.
Ko et al. (Aug. 7, 2008) "A Hemispherical Electronic Eye Camera Based on Compressible Silicon Optoelectronics," *Nature* 454:748-753.
Ko et al. (Web Release Oct. 28, 2009) "Curvilinear Electronics Formed Using Silicon Membrane Circuits and Elastomeric Transfer Elements," *Small* 5(23):2703-2709.
Kocabas et al. (2004) "Aligned Arrays of Single-Walled Carbon Nanotubes Generated from Random Networks by Orientationally Selective Laser Ablation," *Nano Lett.*, vol. 4, No. 12, pp. 2421-2426.
Kocabas et al. (2005) "Guided Growth of Large-Scale, Horizontally Aligned Arrays of Single-Walled Carbon Nanotubes and Their Use in Thin-Film Transstors," *Small* 1(11):1110-1116.
Kocabas et al. (2006) "Large Area Aligned Arrays of SWNTs for High Performance Thin Film Transistors," American Physical Society, APS March Meeting, Mar. 13-17, Abstract # W31.004.
Kocabas et al. (2006) "Spatially Selective Guided Growth of High-Coverage Arrays and Random Networks of Single-Walled Carbon Nanotbes and Thir Integration into Electronic Devices," *J. Am. Chem. Soc.* 128:4540-4541.
Kocabas et al. (2007) "Experimental and Theoretical Studies of Transport Through Large Scale, Partially Aligned Arrays of Single-Walled Carbon Nanotubes ni Thin Film Type Transistors," *Nano Lett.* 7(5):1195-1202.
Kocabas et al. (Feb. 5, 2008) "Radio Frequency Analog Electronics Based on Carbon Nanotube Transistors," *Proc. Natl. Acad. Sci. USA* 105(5):1405-1409.
Kodambaka et al. (2006) "Control of Si Nanowire Growth by Oxygen," *Nano Lett.* 6(6):1292-1296.
Koide et al. (2000) "Patterned Luminescence of Organic Light-Emitting Diodes by Hot Microcontact Printing (HCP) of Self-Assembled Monolayers," *J. Am. Chem. Soc.* 122:11266-11267.
Konagai et al. (1978) "High Efficiency GaAs Thin Film Solar Cells by Peeled Film Technology," *J. Cryst. Growth* 45:277-280.
Kong et al. (2004) "Single-Crystal Nanorings Formed by Epitaxial Self0Coating of Polar Nanobelts," *Science* 303:1348-1351.

(56) References Cited

OTHER PUBLICATIONS

Kong et al. (Jan. 28, 2000) "Nanotube Molecular Wires as Chemical Sensors," *Science* 287:622-625.
Kong et al. (Oct. 2003) "Structure of Indium Oxide Nanobelts," *Solid State Commun.* 128(1):1-4.
Kong et al. (Oct. 29, 1998) "Synthesis of Individual Single-Walled Carbon Nonotubes on Patterned Silicon Wafers," *Nature* 395:878-881.
Kubo et al. (2010) "Stretchable Microfluidic Radiofrequency Antennas," *Adv. Mater.* 22:2749-2752.
Kudo et al. (Web Release Jun. 13, 2006) "A Flexible and Wearable Glucose Sensor Kudo Based on Functional Polymers with Soft-MEMS Techniques," *Biosens. Bioelectron.* 22:558-562.
Kulkarni et al. (2002) "Mesoscale Organization of Metal Nanocrystals," *Pure Appl. Chem* 74(9):1581-1591.
Kumar et al. (1993) "Features of Gold Having Micrometer to Centimeter Dimensions can be Formed Through a Combination of Stamping with an Elastomeric Stamp and an Alkanethiol "Ink" Followed by Chemical Etching," *Appl. Phys. Lett.* 63(4):2002-2004.
Kumar et al. (1994) "Patterning Self-Assembled Monolayers: Applications in Materials Science," *Langmuir* 10:1498-1511.
Kumar et al. (2002) "Thermally-Stable Low-Resistance Ti/Al/Mo/Au Multilayer Ohmic Contacts on n-GaN," *J. Appl. Phys.* 92:1712-1714.
Kumar et al. (2005) "Percolating in Finite Nanotube Networks," *Phys. Rev. Lett.*, 95, 066802.
Kumar et al. (2006) "Ultrasensitive DNA Sequence Detection Using Nanoscale ZnO Sensor Arrays," *Nanotechnology.* 17:2875.
Kumar et al. (2011) "ZnO Nanoparticle as Catalyst for Efficient Green One-Pot Synthesis of Coumarins through Knoevenagel Condensation," *J. Chem. Sci.* 123:615.
Kuo (2004) Ch.6 In; Thin Film Transistors Materials and Processes. vol. 1. *Klewer Academic.* Norwell, MA.
Kuo et al. (1985) "Effect of Mismatch Strain on Band Gap in III-V Semiconductors," *J. Appl. Phys.* 57:5428-5432.
Kurzweil (2009) "Metal Oxides and Ion-Exchanging Surfaces as pH Sensors in Liquids: State-of-the-Art and Outlook," *Sensors* (Basel). 9:4955-85.
Kuwazuru et al. (2008) "Mechanical Approach to Aging and Wrinkling of Human Facial Skin Based on the Multistage Buckling Theory," *Med. Eng. Physics.* 30:516-522.
Kuykendall et al. (Aug. 2004) "Crystallographic Alignment of High Density Gallium Nitride Nanowire Arrays," *Nat. Mater.* 3:524-528.
Kwak et al. (2011) "Rational Design and Enhanced Biocompatibility of a Dry Adhesive Medical Skin Patch," *Adv. Mater.* 23:3949-3953.
Lacour et al. (2005) "Stretchable Interconnects for Elastic Electronic Surfaces," *Proc. IEEE* 93:1459-1467.
Lacour et al. (2010) "Flexible and Stretchable Micro-Electrodes for in Vitro and n Vivo Neural Interfaces," *Med. Biol. Eng. Comput.* 48:945-954.
Lacour et al. (Apr. 14, 2003) "Stretchable Gold Conductors on Elastomeric Substrates," *Appl. Phys. Lett.* 82(15):2404.
Lacour et al. (Apr. 2004) "Design and Performance of Thin Metal Film Interconnects for Skin-Like Electronic Circuits," *IEEE Electron. Dev. Lett.* 25(4):179-181.
Lacour et al. (Dec. 2004) "An Elastically Stretchable TFT Circuit," *IEEE Electron Dev. Lett.* 25(12):792-794.
Lacour et al. (Web Release Jul. 14, 2006) "Stiff Subcircuit Islands of Diamondlike Carbon for Stretchable Electronics," *J. Appl. Phys.* 100:014913.
Lacour et al. (Web Release May 16, 2006) "Mechanisms of Reversible Stretchability of Thin Metal Films on Elastomeric Substrates," *Appl. Phys. Lett.* 88:204103.
Laimer et al. (Mar. 1997) "Diamond Growth in a Direct-Current Low-Pressure Supersonic Plasmajet," *Diamond Relat. Mater.* 6:406-410.
Lambacher et al. (2004) "Electrical Imaging of Neuronal Activity by Multi-Transistor-Array (MTA) Recording at 7.8 μm Resolution," *Appl. Phys. A* 79:1607-1611.
Landes et al. (2002) "Some Properties of Spherical and Rod-Shaped Semiconductor and Metal Nanocrystals," *Pure Appl. Chem.* 74(9):1675-1692.
Law et al. (2004) "Semiconductor Nanowires and Nanotubes," *Ann. Rev. Mater. Res.* 34:83-122.
Law et al. (Aug. 27, 2004) "Nanoribbon Waveguides for Subwavelength Photonics Integration," *Science* 305:1269-1273.
Lawrence et al. (2008) "Bioactive Silk Protein Biomaterial Systems for Optical Devices," *Biomacromolecules* 9:1214-1220.
Lay et al. (2004) "Simple Route to Large-Scale Ordered Arrays of Liquid-Deposited Carbon Nanotubes," *Nano Lett.*, vol. 4, No. 4, pp. 603-606.
Leclercq et al. (1998) "III-V Micromachined Devices for Microsystems," *Microelectronics J.* 29:613-619.
Lecomte et al. (Apr. 2006) "Degradation Mechanism of Diethylene Glycol Units in a Terephthalate Polymer," *Polym. Degrade. Stab.* 91(4):681-689.
Lee et al. (2000) "Thin Film Transistors for Displays on Plastic Substrates," *Solid State Electron.* 44:1431-1434.
Lee et al. (2003) "High-Performance Poly-Si TFTs on Plastic Substrates Using a Nano-Structured Separation Layer Approach," *IEEE Elec. Dev. Lett.* 24:19-21.
Lee et al. (2004)"Organic Light-Emitting Diodes Formed by Soft Contact Lamination," *Proc. Natl. Acad. Sci. USA* 101(2):429-433.
Lee et al. (2005) "A Printable Form of Single-Crystalline Gallium Nitride for Flexable Optoelectronic Systems," *Small* 1:1164-1168.
Lee et al. (2005) "Dielectrophoresis and Chemically Mediated Directed Self-Assembly of Micrometer-Scale Three-Terminal Metal Oxide Semiconductor Field-Effect Transistors," *Adv. Mater.* 17:2671-2677.
Lee et al. (2005) "Large-Area, Selective Transfer of Microstructured Silicon (μs-Si): A Printing-Based Approach to High-Performance Thin0Film Transistors Supported on Flexible Substraights," *Adv. Mater.* 17:2332-2336.
Lee et al. (2006) "Micron and Submicron Patterning of Polydimethylsiloxane Resists on Electronic Materials by Decal Transfer Lithography and Reactive Ion-Beam Etching: Application to the Fabrication of High-Mobility, Thin-Film Transistors," *Appl. Phys. Lett.* 100:084907/1-7.
Lee et al. (Apr. 2005) "Fabrication of Stable Metallic Patterns Embedded in Poly(dimethylsiloxane) and Model Applications in Non-Planar Electronic and Lab-on-a-Chip Device Patterning," *Adv. Funct. Mater.* 15(4):557-566.
Lee et al. (Dec. 1999) "The Surface/Bulk Micromachining (SBM) Process: A New Method for Fabricating Released MEMS in Single Crystal Silicon," *J. Microelectromech. Syst.* 8(4):409-416.
Lee et al. (Feb. 2001) "Application of Carbon Nanotubes to Field Emission Displays," *Diamond and Related Mater.* 10(2):265-270.
Lee et al. (Feb. 2005) "Weave Patterned Organic Transistors on Fiber for E-Textiles," *IEEE Trans. Electron. Dev.* 52(2):269-275.
Legnani et al. (2008) "Bacterial Cellulose Membrane as Flexible Substrate for Organic Light Emitting Devices," *Thin Film Solids.* 517:1016.
Leong et al. (2009) "Tetherless Thermobiochemicall Actuated Microgrippers," *Proc. Natl. Acad. Sci. USA* 106:703-709.
Létant et al. (Jun. 2003) "Functionalized Silicon Membranes for Selective Bio-Organisms Capture," *Nat. Mater.* 2:391-395.
Leveque et al. (1983) "Impedance methods for studying skin moisturization," *J. Cosmet. Sci.* 34:419-428.
Li et al. (2002) "High-Resolution Contact Printing with Dendrimers," *Nano Lett.* 2(4):347-349.
Li et al. (2003) "Ultrathin Single-Crystalline-Silicon Cantilever Resonators: Fabrication Technology and Significant Specimen Size effect on Young's Modulus," *Appl. Phys. Lett.* 83:3081-3083.
Li et al. (2004) "Electrospinning of Nanofibers: Reinventing the Wheel," *Adv. Mater.* 16(14):1151-1170.
Li et al. (2006) "Catalyst-Assisted Formation of Nanocantilever Arrays on ZnS Nanoribbons by Post-Annealing Treatment," *J. Phys. Chem. B* 110(13):6759-6762.
Li et al. (2008) "Cellular Level Biocompatibility and Biosafety of ZnO Nanowires," *J. Phys. Chem. C.* 112:20114.

(56) References Cited

OTHER PUBLICATIONS

Li et al. (Dec. 2005) "Compliant Thin Film Patterns of Stiff Materials as Platforms for Stretchable Electronics," *J. Mater. Res.* 20(12):3274-3277.
Li et al. (Jul. 1, 2002) "ZnO Nanobelts Grown on Si Substrate," *Appl. Phys. Lett.* 81:144-146.
Li et al. (Jan. 21, 2013) "An Analytical Model of Reactive Diffusion for Transient Electronics," *Adv. Funct. Mater.* 23:3106-3114.
Liang et al. (2010) "Biomechanical properties of in vivo human skin from dynamic optical coherence elastography," *IEEE Trans. Biomed. Eng.* 57:953-959.
Lieber, C. (2001) "The Incredible Shrinking Circuit," *Sci. Am.* 285(3):58-64.
Lieber, C.M. (2003) "Nanoscale Science and Technology: Building a Bog Future from Small Things," *MRS. Bull.* 28:486-491.
Lim et al. (2005) "Flexible Membrane Pressure Sensor," *Sens. Act. A* 119:332-335.
Lima et al. (2007) "Creating Micro- and Nanostructures on Tubular and Spherical Surfaces," *J. Vac. Sci. Technol. B* 25(6):2412-2418.
Lin et al. (2011) "Novel dry polymer foam electrodes for long-term EEG measurement," *IEEE T. Bio-Med. Eng.* 58:1200-1207.
Lin et al. (Sep. 2005) "High-Performance Carbon Nanotube Field-Effect Transistor With Tunable Polarities," *IEEE Trans. Nano* 4(5):481-489.
Linder et al. (1994) "Fabrication Technology for Wafer Through-Hole Interconnections and Three-Dimensional Stacks of Chips and Wafers," *Proc. IEEE Micro. Electro Mech. Syst.* 349-354.
Ling et al. (2004) "Thin Film Deposition, Patterning, and Printing in Organic Thin Film Transistors," *Chem. Mater.* 16:4824-4840.
Lipomi et al. (2011) "Skin-Like Sensors of Pressure and Strain Enabled by Transparent, Elastic Films of Carbon Nanotubes," *Nature Nanotech.* 6:788-792.
Liu et al. (1999) "Controlled deposition of individual single-walled carbon nanotubes on chemically functionalized templates," *Chem. Phys. Lett.*, 303:125-129.
Long et al. (1990) "Heterostructure FETs and Bipolar Transistors," In; *Gallium Arsenide Digital Integrated Circuit Design*, McGraw-Hill, New York, pp. 58-69.
Loo et al. (2002) "Additive, Nanoscale Patterning of Metal Films with a Stamp and a Surface Chemistry Mediated Transfer Process: Applications in Plastic Electronics," *Appl. Phys. Lett.* 81:562-564.
Loo et al. (2002) "High-Resolution Transfer Printing on GaAs Surfaces Using Alkane Dithiol Monolayers," *J. Vac. Sci. Technol. B* 20(6):2853-2856.
Loo et al. (2002) "Interfacial Chemistries for Nanoscale Transfer Printing," *J. Am. Chem. Soc.* 124:7654-7655.
Loo et al. (2002) "Soft, Conformable Electrical Contacts for Organic Semiconductors: High-Resolution Plastic Circuits by Lamination," *Proc. Natl. Acad. Sci. USA* 99(16):10252-10256.
Loo et al. (2003) "Electrical Contacts to Molecular Layers by Nanotransfer Printing," *Nano Lett.* 3(7):913-917.
Loo et al. (2008) "Progress and Challenges in Commercialization of Organic Electronics," *MRS Bull.* 33:653-662.
Lopes et al. (Sep. 2004) "Thermal Conductivity of PET/(LDPE/Al) Composites Determined by MDSC," *Polym. Test.*23(6):637-643.
Lozano (2009) "Electrotactile Stimulation on the Tongue: Intensity Perception, Discrimination, and Cross-Modality Estimation," *Somatosens. Mot. Res.* 26:50-63.
Lu et al. (Apr. 2010) "Water-Insoluble Silk Films with Silk I Structure," *Acta Biomater.* 6(4):1380-1387.
Lu et al. (Dec. 2006) "Electronic Materials-Buckling Down for Flexible Electronics," *Nat. Nanotechnol.* 1:163-164.
Lu et al. (Jul. 19, 2005) "One Dimensional Hole Gas in Germanium/Silicon Nanowire Heterostructures," *Proc. Nat. Acad. Sci. USA* 102(29):10046-10051.
Lu et al. (Nov. 2008) "Nanowire Transistor Performance Limits and Applications," *IEEE Trans Electron Dev.* 55(11):2859-2876.
Luan et al. (1992) "An Experimental Study of the Source/Drain Parasitic Resistance Effects in Amorphous Silicon Thin Film Transistors," *J. Appl. Phys.* 72:766-772.
Ma et al. (2004) "Single-Crystal CdSe Nanosaws," *J. Am. Chem. Soc.* 126(3):708-709.
Ma et al. (2010) "A Stretchable Electrode Array for Non-Invasive, Skin-Mounted Measurement of Electrocardiography (ECG), Electromyography (EMG) and Electroencephalography (EEG)," In; Engineering in Medicine and Biology Society (EMBC), 2010 Annual International Conference of the IEEE. Buenos Aires, Arentina. pp. 6405-6408.
Mack et al. (2006) "Mechanically Flexible Thin-Film Transistors that Use Ultrathin Ribbons of Silicon Derived from Bulk Wafers," *Appl. Phys. Lett.* 88:213101.
Madou, M. (1997) "Etch-Stop Techniques," In; *Fundamentals of Microfabrication*, CRC Press, New York, pp. 193-199.
Maikap et al. (2004) "Mechanically Strained-Si NMOSFETs," *IEEE Electron. Dev. Lett.* 25:40-42.
Maldovan et al. (2004) "Diamond-Structured Photonic Crystals," *Nature Materials* 3:593-600.
Mamishev et al. (2004) "Interdigital sensors and transducers," *Proc. IEEE.* 92:808-845.
Mandlik et al. (Aug. 2006) "Fully Elastic Interconnects on Nanopatterned Elastomeric Substrates," *IEEE Electron Dev. Lett.* 27(8):650-652.
Manna et al. (Web Release May 25, 2003) "Controlled Growth of Tetrapod-Branched Inorganic Nanocrystals," *Nat. Mater.* 2:382-385.
Mannsfeld et al. (2010) "Highly Sensitive Flexible Pressure Sensors with Microstructured Rubber Dielectric Layers," *Nat. Mater.* 9:859-864.
Markovich et al. (1999) "Architectonic Quantum Dot Solids," *Acc. Chem. Res.* 32:415-423.
Marquette et al. (2004) "Conducting Elastomer Surface Texturing: A Path to Electrode Spotting Application to the Biochip Production," *Biosens. Bioelectron.* 20:197-203.
Martensson et al. (2004) "Nanowire Arrays Defined by Nanoimprint Lithography," *Nano Lett.* 4:699-702.
Martin, C.R. (1995) "Template Synthesis of Electronically Conductive Polymer Nanostructures," *Acc. Chem. Res.* 28:61-68.
Martinez-Boubeta et al. (2010) "Self-Assembled Multifunctional Fe/MgO Nanospheres for Magnetic Resonance Imaging and Hyperthermia," *Nanomedicine: Nanotechnology, Biology, and Medicine.* 6:362.
Martinsen, et al. (1999) "Measuring depth depends on frequency in electrical skin impedance measurements," *Skin Research and Technology.* 5:179-181.
Mas-Torrent et al. (2006) "Large Photoresponsivity in High-Mobility Single-Crystal Organic Field-Effect Phototransistors," *ChemPhysChem* 7:86-88.
Masuda et al. (2000) "Fabrication of Ordered Diamonds/Metal Nanocomposite Structures," *Chem. Lett.* 10:1112-1113.
Masuda et al. (2003) "Transparent Thin Film Transistors Using Zno as an Active Channel Layer and Their Electrical Properties," *J. Appl. Phys.* 93:1624.
Matsunaga et al. (2003) "An Improved GaAs Device Model for the Simulation of Analog Integrated Circuit," *IEEE Trans. Elect. Dev.* 50:1194-1199.
Matteau et al. (2010) "Beyond Visual, Aural and Haptic Movement Perception: hMT+ is Activated by Electrotactile Motion Stimulation of the Tongue in Sighted and in Congenitally Blind Individuals," *Brain Research Bulletin.* 82:264-270.
Matthie (2008) "Bioimpedance Measurements of Human Body Composition: Critical Analysis and Outlook," *Expert Rev. Med. Devices.* 5:239-261.
McAlpine et al. (2003) "High-Performance Nanowire Electronics and Photonics on Glass and Plastic Substrates," *Nano Lett.* 3:1531-1535.
McAlpine et al. (2005) "High-Performance Nanowire Electronics and Photonics and Nanoscale Patterning on Flexible Plastic Substrates," *Proc. IEEE* 93:1357-1363.
McCaldin et al. (1971) "Diffusivity and Solubility of Si in the Al Metallization of Integrated Circuits," *Appl. Phys. Lett.* 19:524-517.
Mehring C. et al. (2003) Inference of hand movements from local field potentials in monkey motor cortex. *Nature Neurosci.* 6, 1253-1254.

(56) References Cited

OTHER PUBLICATIONS

Meisel et al. (2004) "Three-Dimensional Photonic Crystals by Holographic Lithography Using the Umbrella Configuration: Symmetries and Complete Photonic Band Gaps," *Phys. Rev. B.* 70:165101:1-10.

Meitl et al. (2004) "Solution Casting and Transfer Printing Single-Walled Carbon Nanotube Films," *Nano Lett.* 4:1643-1947.

Meitl et al. (2006) "Transfer Printing by Kinetic Control of Adhesion to an Elastomeric Stamp," *Nat. Mater.* 5:33-38.

Meitl et al. (Web Release Feb. 22, 2007) "Stress Focusing for Controlled Fracture in Microelectromechanical Systems," *Appl. Phys. Lett.* 90:083110.

Melosh et al. (2003) "Ultrahigh-Density Nanowire Lattices and Circuits," *Science* 300:112-115.

Menard et al. (2004) "A Printable Form of Silicon for High Performance Thin Film Transistors on Plastic Substrates," *Appl. Phys. Lett.* 84:5398-5400.

Menard et al. (2004) "Improved Surface Chemistries, Thin Film Deposition Techniques, and Stamp Designs for Nanotransfer Printing," *Langmuir* 20:6871-6878.

Menard et al. (2004) "High-Performance n- and p-Type Single-Crystal Organic Transistors with Free-Space Gate Dielectrics," *Adv. Mat.* 16:2097-2101.

Menard et al. (2005) "Bendable Single Crystal Silicon Thin Film Transistors Formed by Printing on Plastic Substrates," *Appl. Phys. Lett.* 86(093507):1-3.

Menard et al. (2007) "Micro- and Nanopatterning Techniques for Organic Electronic and Optoelectronic Systems," *Chem. Rev.* 107:1117-1160.

Miao et al. (2003) "Micromachining of Three-Dimensional GaAs Membrane Structures Using High-Energy Nitrogen Implantation," *J. Micromech. Microeng.* 13:35-39.

Michalske et al. (1985) "Closure and Repropagation of Healed Cracks in Silicate Glass," *J. Am. Ceram. Soc.* 68:586-590.

Michel et al. (2001) Printing Meets Lithography: Soft Approaches to High-Resolution Printing, *IBM J. Res. Dev.* 45:697-719.

Miller et al. (2002) "Direct Printing of Polymer Microstructures on Flat and Spherical Surfaces Using a Letterpress Technique," *J. Vac. Sci. Technol. B* 20(6):2320-2327.

Milliron et al. (2004) "Colloidal Nanocrystal Heterostructures with Linear and Branched Topology," *Nature* 430:190-195.

Min, G. (Apr. 4, 2003) "Plastic Electronics and Their Packaging Technologies," *Syn. Metals.* 135:141-143.

Minev et al. (2010) "Impedance Spectroscopy on Stretchable Microelectrode Arrays," *Appl. Phys. Lett.* 97:043707.

Mirkin et al. (2001) "Emerging Methods for Micro- and Nanofabrication," *MRS Bulletin* 26(7):506-507.

Misewich et al. (May 2, 2003) "Electronically Induced Optical Emission from a Carbon Nanotube FET," *Science* 300:783-786.

Mishra et al. (2002) "AlGaN/GaN HEMTs—an Overview of Device Operation and Applications," *Proc. IEEE* 90:1022-1031.

Mitzi et al. (2004) "High-Mobility Ulltrathin Semiconducting Films Prepared by Spin Coating," *Nature* 428:299-303.

Miyamoto et al. (2004) "High-Electron-Mobility ZnO epilayers Grown by Plasma-Assisted Molecular Beam Epitaxy," *Journal of Crystal Growth.* 265:34.

Momose et al. (2002) "Ultrathin gate oxide CMOS on (111) surface-oriented Si substrate," *IEEE Trans. Electron. Dev.* 49:1597-1605.

Mondal et al. (2008) "Preparation of Al-doped ZnO (AZO) Thin Film by SILAR," *Journal of Physical Sciences.* 12:221.

Moon et al. (2002) "Ink-Jet Printing of Binders for Ceramic Components," *J. Am. Ceram. Soc.* 85:755-762.

Moore et al. (1959) "II. Diffusion of Zinc and Oxygen in Zinc Oxide," *Discussions of the Faraday Society.* 28:86.

Moore et al. (Sep. 9, 2003) "Individually Suspended Single-Walled Carbon Nanotubes in Various Surfactants," *Nano Lett.* 3(10):1379-1382.

Morales et al. (Jan. 9, 1998) "A Laser Ablation Method for the Synthesis of Crystalline Semiconductor Nanowires," *Science* 279:208-211.

Moravej et al. (2011) "Biodegradable Metals for Cardiovascular Stent Application: Interests and New Opportunities," *Int. J. Mol. Sci.* 12:4250.

Morent et al. (2007) "Adhesion Enhancement by a Dielectric Barrier Discharge of PDMS used for Flexible and Stretchable Electronics," *J. Phys. D. Appl. Phys.* 40:7392-7401.

Mori et al. (1978) "A New Etching Solution System, $H_3PO_4$-$H_2O_2$-$H_2O$, for GaAs and Its Kinetics," *J. Electrochem. Soc.* 125:1510-1514.

Morkoc et al. (1995) "High-Luminosity Blue and Blue-Green Gallium Nitride Light-Emitting Emitting Diodes," *Science* 267:51-55.

Morkved et al. (1994) "Mesoscopic Self-Assembly of Gold Islands on Diblock-Copolymer Films," *Appl. Phys. Lett.* 64:422-424.

Morra et al. (1990) "On the Aging of Oxygen Plasma-Treated Polydimthylsiloxane Surfaces," *J. Colloid Interface Sci.* 137:11-24.

Mudunkotuwa et al. (2012) "Dissolution of ZnO Nanoparticles at Circumeutral pH: A Study of Size Effects in the Prescencse and Asbsence of Citric Acid," *Langmuir.* 28:396.

Murakami et al. (2005) "Polarization Dependence of the Optical Absorption of Single-Walled Carbon Nanotubes," *Phys. Rev. Lett.*, 94, 087402.

Murphy et al. (2008) "Modification of Silk Fibroin Using Diazonium Coupling Chemistry and the Effects on hMSC Proliferation and Differentiation," *Biomaterials* 29:2829-2838.

Namazu et al. (2000) "Evaluation of Size Effect on Mechanical Properties of Single Crystal Silicon by Nanoscale Bending Test Using AFM," *J. MEMS* 9:450-459.

Nath et al. (2002) "Nanotubes of the Disulfides of Groups 4 and 5 Metals," *Pure Appl. Chem.* 74(9):1545-1552.

Nathan et al. (2000) "Amorphous Silicon Detector and Thin Film Transistor Technology for Large-Area Imaging of X-Rays,." *Microelectron J.* 31:883-891.

Nathan et al. (2002) "Amorphous Silicon Technology for Large Area Digital X-Ray and Optical Imaging," *Microelectronics Reliability* 42:735-746.

Newman et al. (2004) "Introduction to Organic Thin Film Transistors and Design of n-Channel Channel Organic Semiconductors," *Chem. Mater.* 16:4436-4451.

Nirmal et al. (1999) "Luminescence Photophysics in Semiconductor Nanocrystals," *Acc. Chem. Res.* 32:407-414.

Noda et al. (1996) "New Realization Method for Three-Dimensional Photonic Crystal in Optical Wavelength Region," *Jpn. J. Appl. Phys.* 35:L909-L912.

Nomura et al. (2004) "Room-Temperature Fabrication of Transparent Flexible Thin-Film Transistors Using Oxide Semiconductors," *Nature* 432:488-492.

Novoselov et al. (Oct. 22, 2004) "Electric Field Effect in Atomically Thin Carbon Films," *Science* 306:666-669.

O'Connell et al. (Jul. 26, 2002) "Bang Gap Fluorescence from Individual Single-Walled Walled Caarbon Nanotubes," *Science* 297:593-596.

O'Riordan et al. (2004) "Field Configured Assembly: Programmed Manipulation and Self-Assembly at the Mesoscale," *Nano Lett.* 4:761-765.

Odom et al. (2002) "Improved Pattern Transfer in Soft Lithography Using Composite Stamps," *Langmuir* 18(13):5314-5320.

Oehler et al. (2008) "Extraction of SSVEP signals of a capacitive EEG helmet for human machine interface," *IEEE EMBS.* pp. 4495-4498.

Office Action and Response, Corresponding to Malaysian Patent Publication No. PI 20052553, Mailed Mar. 13, 2009 and Dec. 8, 2009.

Office Action, Corresponding to U.S. Appl. No. 11/423,287, Mailed Feb. 13, 2008.

Office Action and Response, Corresponding to U.S. Appl. No. 11/421,654, Mailed Sep. 29, 2009.

Office Action and Response, Corresponding to U.S. Appl. No. 11/858,788, Mailed Beginning Jan. 28, 2011.

(56) References Cited

OTHER PUBLICATIONS

Office Action Corresponding to Chinese Patent Application No. 200780041127.6, Issued Apr. 8, 2011.
Office Action Corresponding to Chinese Patent Application No. 200780049982.1, Issued May 12, 2010.
Office Action Corresponding to Chinese Patent Application No. 201010519400.5, issued Nov. 3, 2011.
Office action Corresponding to Korean Patent Application No. 10-2006-7010632, Completed Nov. 22, 2007.
Office Action Corresponding to U.S. Appl. No. 11/851,182, Mailed Apr. 1, 2010.
Office Action, Corresponding to Chinese Patent Application No. 200780048002.6, Issued Apr. 13, 2010.
Office Action, Corresponding to Chinese Patent Application No. 200580013574.1, Issued May 11, 2010.
Office Action, Corresponding to Taiwan Patent Application No. 095121212, Issued May 7, 2010.
Office Action, Corresponding to U.S. Appl. No. 11/981,380, Mailed Sep. 23, 2010.
Office Actions and Responses, Corresponding to U.S. Appl. No. 11/145,542, Mailed between Apr. 5, 2007 and Dec. 23, 2008.
Office Actions and Responses, Corresponding to U.S. Appl. No. 11/981,380, Mailed Beginning Sep. 23, 2010.
Office Actions Corresponding to Chinese Patent Application No. 200480035731.4, Issued Mar. 27, 2009 and Dec. 3, 2010.
Office Actions, Corresponding to Chinese Patent Application No. 200580018159.5, Issued Jan. 23, 2009 and Feb. 12, 2010.
Ohzono et al. (2004) "Ordering of Microwrinkle Patterns by Compressive Strain," *Phys. Rev. B* 69(13):132202.
Ohzono et al. (Web Release Jul. 7, 2005) "Geometry-Dependent Stripe Rearrangement Processes Induced by Strain on Preordered Microwrinkle Patterns," *Langmuir* 21(16):7230-7237.
Omenetto et al. (2008) "A New Route for Silk," *Nature Photon.* 2:641-643.
Ondo-Ndong et al. (2003) "Electrical Properties of Zinc Oxide Sputtered Thin Films," *Microelectronics Journal.* 34:1087.
Ong et al. (2004) "High-Performance Semiconducting Poolythiophenes for Organic Thin-Film Transistors," *J. Am. Chem. Soc.* 126:3378-3379.
Ong et al. (2005) "Design of High-Performance Regioreular Polythiophenes for Organic Thin-Film Transistors," *Proc. IEEE* 93:1412-1419.
Origin Energy (May 2004) "Fact Sheet—Sliver Cells," www.orginenergy.com.au/sliver.
Ouyang et al. (2002) "High-Performance, Flexible Polymer Light-Emitting Diodes Fabricated by a Continuous Polymer Coating Process," *Adv. Mat.* 14:915-918.
Ouyang et al. (2008) "High Frequency Properties of Electro-Textiles for Wearable Antenna Applications," *IEEE Trans. Antennas Propag.* 56(2):381-389.
Ouyang et al. (Web Release Mar. 20, 2000) "Conversion of Some Siloxane Polymers to Silicon Oxide by UV/Ozone Photochemical Processes," *Chem. Mater.* 12(6)1 591-1596.
Overholt et al. (2005) "Photodynamic Therapy for Esophageal Cancer using a 180° Windowed Esophageal Balloon," *Lasers in Surg. Med.* 14:27-33.
Pailler-Mattei et al. (2008) "In Vivo Measurements of the Elastic Mechanical Properties of Human Skin by Indentation Tests," *Med. Eng. Phys.* 30:599-606.
Pan et al. (2001) "Nanobelts of Semiconducting Oxides," *Science* 291:1947-1949.
Panev et al. (2003) "Sharp Excitation from Single InAs Quantum Dots in GaAs Nanowires," *Appl. Phys. Lett.* 83:2238-2240.
Pang et al. (2012) "A flexible and highly sensitive strain-gauge sensor using reversible interlocking of nanofibres," *Nat. Mater.* 11:795-801.
Panilaitis et al. (2003) "Macrophage Activation in Response to Silk," *Biomaterials.* 24:3079.

Pardo et al. (2000) "Application of Screen Printing in the Fabrication of Organic Ligh-Emitting Devices," *Adv. Mater.* 12(17):1249-1252.
Park et al. (1997) "Block Copolymer Lithography: Periodic Arrays of ~$10^{11}$ Holes in 1 Square Centimeter," *Science* 276:1401-1404.
Park et al. (1998) "Fabrication of Three-Dimensional Macroporous Membranes with Assemblies of Microspheres as templates," *Chem. Mater.* 10:1745-1747.
Park et al. (2008) "Theoretical and Experimental Studies in Bending of Inorganic Electronic Materials on Plastic Substrates," *Adv. Funct. Mater.* 18:2673.
Park et al. (2009) "The Effects of Rapid Thermal Annealing on the Performance of ZnO Thin-Film Transistors," *Journal of the Korean Physical Society.* 55:1925.
Park et al. (Aug. 2009) "Printed Assemblies of Inorganic Light-Emitting Diodes for Deformable and Semitransparent Displays," *Science* 325:977-981.
Park et al. (Web Release Feb. 22, 2009) "Biodegradable Luminescent Porous Silicon Nanoparticles for in Vivo Applications," *Nature Mater.* 8:331-336.
Parker et al. (2009) "Biocompatible Silk Printed Optical Waveguides," *Adv. Mater.* 21:2411-2415.
Patolsky et al. (2006) "Detection, Stimulation, and Inhibition of Neuronal Signals with High-Density Nanowire Transistor Arrays," *Science.* 313:1100-1104.
Patton et al. (Mar. 1998) "Effect of Diamond like Carbon Coating and Surface Topography on the Performance of Metal Evaporated Magnetic Tapes," *IEEE Trans Magn.* 34(2):575-587.
Paul et al. (Apr. 2003) "Patterning Spherical Surfaces at the Two Hundred Nanometer Scale Using Soft Lithography," *Adv. Func. Mater.* 13(4):259-263.
Paye et al. (1995) "Corneometiy Measurements to Evaluate Skin Dryness in the Modified Soap Chamber Test," *Skin Research and Technology.* 1:123-127.
Pearton et al. (1999) "GaN: Processing, Defects, and Devices," *J. Appl. Phys.* 86:1-78.
Peng et al. (Mar. 2, 2000) "Shape Control of CdSe Nanocrystals," *Nature* 404:59-61.
Perry et al. (2008) "Nano- and Micropatterning of Optically Transparent, Mechanically Robust, Biocompatible Silk Fibroin Films," *Adv. Mater.* 20:3070-3072.
Piazza et al. (2005) "Protective Diamond-Like Carbon Coatings for Future Optical Storage Disks," *Diamond Relat. Mater.* 14:994-999.
Pierret (1996) Ch. 18 In; Semiconductor Device Fundamentals. *Addison-Wesley.* Natick, MA.
Pimparkar et al. (Feb. 2007) "Current-Voltage Characteristics of Long-Channel Nanobundle Thin-Film Transistors: A 'Bottom-Up' Perspective," *IEEE Electron Dev. Lett.* 28(2):157-160.
Piskorowski (2012) "Suppressing harmonic powerline interference using multiple-notch filtering methods with improved transient behavior," *Measurement.* 45:1350-1361.
Podzorov et al. (2005) "Hall Effect in the Accumulation Layers on the Surface of Orgaic Semiconductors," *Phys. Rev. lett.* 95:226601.
Popescu et al. (2007) "Single trial classification of motor imagination using 6 dry EEG electrodes," *PloS One.* 2(7):e637.
Pushpa et al. (2002) "Stars and Stripes. Nanoscale Misfit Dislocation Patterns on Surfaces," *Pure Appl. Chem.* 74(9):1663-1671.
Qian et al. (2006) "Scaling Effects of Wet Adhesion in Biological Attachment Systems," *Acta Biomaterialia* 2:51-58.
Quake et al (2000) "From Micro- to Nanofabrication with Soft Materials," *Science* 290:1536-1540.
Radtke et al. (Feb. 5, 2007) "Laser-Lithography on Non-Planar Surfaces," *Opt. Exp.* 15(3):1167-1174.
Raicu et al. (2000) "A quantitative approach to the dielectric properties of the skin," *Phys. Med. Biol.* 45:L1-L4.
Raman et al. (1989) "Study of Mesa Undercuts Produced in GaAs with $H_3PO_4$-Based Etchants," *J. Electrochem. Soc.* 136:2405-2410.
Randall et al. (2005) "Permeation-driven flow in poly(dimethylsiloxane) microfluidic devices," *Proc. Nat. Acad. Sci. USA* 102(31):10813-10818.
Rao et al. (2003) "Large-scale assembly of carbon nanotubes," *Nature,* 425:36-37.

(56) References Cited

OTHER PUBLICATIONS

Razavi et al. (2009) "Three Dimensional Nanopillar Array Photovoltaics on Low Cost and Flexible Substrates," *Nature Materials* 8:648-653.
Razeghi et al. (1994) "High-Power Laser Diode Based on In GaAsP Alloys," *Nature* 369:631-633.
Razouk et al. (Sep. 1979) "Dependence of Interface State Density on Silicon Thermal Oxidation Process Variables," *J. Electrochem. Soc.* 126(9):1573-1581.
Reed et al. (2012) "Solubility of Nano-Zinc Oxide in Environmentally and Biologically Important Matrices," *Environ. Toxicol. Chem.* 31:93.
Reuss et al. (Jul. 2005) "Macroelectronics: Perspectives on Technology and Applications," *Proc. IEEE* 93(7):1239-1256.
Reuss et al. (Jun. 2006) "Macroelectronics," *MRS Bull.* 31:447-454.
Ribas et al. (1998) "Bulk Micromachining Characterization of 1.2 μm HEMT MMIC Technology for GaAs MEMS Design," *Mater. Sci. Eng. B* 51:267-273.
Richter et al. (2008) "Review on Hydrogel-based pH Sensors and Microsensors," *Sensors.* 8:561-581.
Ridley et al. (1999) "All-Inorganic Field Effect Transistors Fabricated by Printing," *Science* 286:746-749.
Roberts et al. (1979) "Looking at Rubber Adhesion," *Rubber Chem. Technol.* 52:23-42.
Roberts et al. (Mar. 2006) "Elastically Relaxed Free-Standing Strained-Silicon Nanomembranes," *Nat. Mater.* 5:388-393.
Robinson et al. (1983) "GaAs Readied for High-Speed Microcircuits," *Science* 219:275-277.
Rodriguez et al. (2007) "Dual-Frequency Resonance-Tracking Atomic Force Microscopy," *Nanotechnology.* 18:475504.
Roelkens et al. (Dec. 2005) "Integration of InP/InGaAsP Photodetectors onto Silicon-on-Insulator Waveguide Circuits," *Optics Express* 13(25):10102-10108.
Rogers et al. (1997) "Using an Elastomeric Phase Mask for Sub-100 nm Photolithography in the Optical Near Field," *Appl. Phys. Lett.* 70:2658-2660.
Rogers et al. (1998) "Generating ~90 Nanometer Features Using Near Field Contact Mode Photolithography with an Elastomeric Phase Mask," *J. Vac. Sci. Technol.* 16(1):59-68.
Rogers et al. (1998) "Quantifying Distortions in Soft Lithography," *J. Vac. Sci. Technol.* 16:88-97.
Rogers et al. (1998) "Using Printing and Molding Techniques to Produce Distributed Feedback and Bragg Reflector Resonators for Plastic Lasers," *Appl. Phys. Lett.* 73:1766-1768.
Rogers et al. (1999) "Printing Process Suitable for Reel-to-Reel Production of High-Performance Organic Transistors and Circuits," *Adv. Mater.* 11(9):741-745.
Rogers et al. (2002) "Paper-Like Electronic Displays: Large-Area Rubber-Stamped Plastic Sheets of Electronics and Microencazpsulated Electrophoretic Inks," *Proc. Nat. Acad. Sci. USA* 98:4835-4840.
Rogers et al. (2002) "Printed Plastic Electronics and Paperlike Displays," *J. Polym. Sci. Part A. Polym. Chem.* 40:3327-3334.
Rogers et al. (2009) "A Curvy, Stretchy Future for Electronics," *Proc. Natl. Acad. Sci. U. S. A.* 106:16889.
Rogers et al. (2010) "Materials and Mechanics for Stretchable Electronics," *Science.* 327:1603-1607.
Rogers et al. (Mar. 2000) "Organic Smart Pixels and Complementary Inverter Circuits Formed on Plastic Substrates by Casting and Rubber Stamping," *IEEE Electron Dev. Lett.* 21(3):100-103.
Rogers et al. (Sep. 1, 2011) "Synthesis, Assembly and Applications of Semiconductor Nanomembranes," *Nature.* 477:45-53.
Rogers, J.A. (2001) "Rubber Stamping for Plastic Electronics and Fiber Optics," *MRS Bulletin* 26(7):530-534.
Rogers, J.A. (2001) "Toward Paperlike Displays," *Science* 291:1502-1503.
Rogers, J. (Jul. 9, 2010) "Farewell to Flatland," *Science* 329:139-139.
Rosenblatt et al. (2002) "High Performance Electrolyte Gated Carbon Nanotube Transistors," *Nano Lett.* 2(8):869-872.

Rotkin et al. (2003) "Universal Description of Channel Conductivity for Nanotube and Nanowire Transistors," *Appl. Phys. Lett.* 83:1623-1625.
Roundy et al. (2003) "Photonic Crystal Structure with Square Symetry within Each Layer and a Three-Dimensional Band Gap," *Appl. Phys Lett.* 82:3835-3837.
Rubehn et al. (2009) "A MEMS based Flexible Multichannel ECoG-Electrode Array," *J. Neural Eng.* 6:036003.
Ruchehoeft et al. (2000) "Optimal Strategy for Controlling Linewidth on Spherical Focal Surface Arrays," *J. Vac. Sci. Technol. B* 18(6):3185-3189.
Ruffini et al. (2007) "ENOBIO dry electrophysiology electrode; first human trial plus wireless electrode system," *IEEE EMBS.* pp. 6689-6693.
Ruffini et al. (2008) "First Human Trials of a Dry Electrophisiology Sensor Using a Carbon Nanotube Array Interface," *Sensor Actuat. A: Phys.* 144:275-279.
Ryu et al. (2009) "Human Cortical Prostheses: Lost in Translation?" *Neurosurg Focus* 27(1):E5.
Saad et al. (2010) "Characterization of Various Zinc Oxide Catalysts and Their Activity in the Dehydration-Dehydrogenation of Isobutanol" *J. Serb. Chem. Soc.* 73:997.
Samuelson et al. (2004) "Semiconductor Nanowires for Novel One-Dimensional Devices," *Physica E* 21:560-567.
Sangwal et al. (1997) "Nature of multilayer steps on the {100} cleavage planes of MgO single crystals," *Surf. Sci.*, 383:78-87.
Santin et al. (1999) "In vitro Evaluation of the Inflammatory Potential of the Silk Fibroin," *J. Biomed. Mater. Res.* 46:382-389.
Sanyal et al. (2002) "Morphology of Nanostructures Materials," *Pure Appl. Chem.* 74(9):1553-1570.
Sasai et al. (1996) "High-frequency conductance measurement of the skin surface hydration state of dry skin using a new probe studded with needle-form electrodes (MT-8C)," Skin Res. Technol. 2:173-176.
Sato et al. (1999) "Anisotropic etching rates of single-crystal silicon for TMAH water solution as a function of crystallographic orientation," *Sens. Actuators A.* 73:131-137.
Sazonov et al. (2005) "Low-Temperature Materials and Thin-Film Transistors for Flexible Electronics," *Proc. IEEE* 93:1420-1428.
Scherlag et al. (1969) "Catheter Technique for Recording His Bundle Activity in Man," *Circulation* 39:13-18.
Schermer et al. (Web Release Apr. 28, 2005) "Thin-Film GaAs Epitaxial Lift-Off Solar Cells for Space Applications," *Prog. Photovoltaics: Res. Applic.* 13:587-596.
Schermer et al. (Web Release Jan. 19, 2006) "Photon Confinement in High-Efficiency, Thin-Film III-V Solar Cells Obtained by Epitaxial Lift-Off," *Thin Solid Films* 511-512:645-653.
Schindl et al. (2003) "Direct Stimulatory Effect of Low-Intensity 670-nm Laser Irradiation on Human Endothelial Cell Proliferation," *Br. J. Dermatol.* 148:334-336.
Schlegel et al. (2002) "Structures of quartz (1010)- and (1011)-water interfaces determined by X-ray reflectivity and atomic force microscopy of natural growth surfaces," *Geochim. Cosmochim. Acta*, vol. 66, No. 17, pp. 3037-3054.
Schmid et al. (2003) "Preparation of metallic Films on Elastomeric Stamps and Their Application on Contact Processing and Contact Printing," *Adv. Funct. Mater.* 13:145-153.
Schmid et al. (Mar. 25, 2000) "Siloxane Polymers for High-Resolution, High-Accuracy Accuracy Soft Lithography," *Macromolecules* 33(8):3042-3049.
Schmid et al. (May 11, 1998) "Light0 Coupling Masks for Lensless, Sub-wavelength Optical Lithography," *Appl. Phys. Lett.* 72(19):2379-2381.
Schmidt et al. (Mar. 8, 2001) "Thin Solid Films Roll up into Nanotubes," *Nature* 410:168.
Schneider et al. (2008) "Mechanical Properties of Silicones for MEMS," *J. Micromech. Microeng.* 18:065008.
Schon et al. (1995) "Ambipolar Pentacene Field-Effect Transistors and Inverters," *Science* 287:1022-1023.
Schrieber et al. (1998) "The Effectiveness of Silane Adhesion Promotors in the Performance of Polyurethane Adhesives," *J. Adhesion* 68:31-44.

(56) References Cited

OTHER PUBLICATIONS

Schnable et al. (1969) "Aluminum Metallization; Advantages and Limitations for Integrated Circuit Applications," *IEEE* 57:1570-1580.
Scorzoni et al. (Oct. 4, 2004) "On the Relationship Between the Temperature coefficient of Resistance and the Thermal Conductance of Integrated Metal Resistors," *Sens Actuators A* 116(1):137-144.
Search and Examination Report, Corresponding to Singapore Application No. 200904208-6, Mailed Nov. 8, 2010.
Search Report and Examination Report Corresponding to Singapore Patent Application No. 200901178-4, Completed Mar. 13, 2010.
Search Report and First Written Opinion, Corresponding to Singapore Patent Application No. 200902530-5, Mailed Oct. 5, 2010.
Search Report and Written Opinion, Corresponding to Singapore Application No. 200901451-5, Mailed Dec. 22, 2010.
Search Report Corresponding to Singapore Patent Application No. SG 200607372-0, Mailer Oct. 17, 2007.
Search Report Corresponding to Taiwanese Patent Application No. 095121212, Completed Oct. 8, 2010.
Search Report, Corresponding to Republic of China (Taiwan) Patent Application No. 094118507, Dated Feb. 24, 2007.
Searle et al. (2000) "A Direct Comparison of Wet, Dry and Insulating Bioelectric Recording Electrodes," *Physiol. Meas.* 21:271.
Seidel et al. (2004) "High-Current Nanotube Transistors," *Nano Lett.*, vol. 4, No. 5, pp. 831-834.
Sekitani et al. (2005) "Bending Experiment on Pentacene Fiield-Effect Transistors on Plastic Films," *Appl. Phys. Lett.* 86:073511.
Sekitani et al. (2009) "Stretchable Active-Matrix Organic Light-Emitting Diode Display Using Printable Elastic Conductors," *Nature Mater.* 8:494-499.
Sekitani et al. (2012) "Stretchable Organic Integrated Circuits for Large-Area Electronic Skin Surfaces," *MRS Bull.* 37:236.
Sekitani et al. (Sep. 12, 2008) "A Rubberlike Stretchable Active Matrix Using Elastic Conductors," *Science* 321:1468-1472.
Sen et al. (2002) "Nonequilibrium Processes for Generating Silicon Nanostructures in Single-Crystalline Silicon," *Pure Appl. Chem.* 74(9):1631-1641.
Serikawa et al. (May 1, 2000) "High-Mobility Poly-Si Thin Film Transistors Fabricated on Stainless-Steel Foils by Low-Temperature Processes Using Sputter-Depositions," *Jpn. J. Appl. Phys.* 39:L393-L395.
Servanti et al. (2005) "Functional Pixel Circuits for Elastic AMOLED displays," *Proc. IEEE* 93:1257-1264.
Service, R.F. (Aug. 15, 2003) "Electronic Textiles Charge Ahead," *Science* 301:909-911.
Shahrjerdi et al. (Oct. 23, 2013) "Extremely Flexible Nanoscale Ultrathin Body Silicon Integrated Circuits on Plastic," *Nano Lett.* 13:315-320.
Shan et al. (2004) "From Si Source Gas Directly to Positioned, Electrically Contained Si Nanowires: The Self-Assembling 'Grow-in-Place' Approach," *Nano Lett.* 4(11):2085-2089.
Sharma et al. (1986) "Influence of Heat-Stress Induced Dehydration on Mental Functions," *Ergonomics.* 29:791-799.
Sharp et al. (2003) "Holographic Photonic Crystals with Diamond Symmetry," *Phys. Rev. B* 68:205102/1-205102/6.
Shen et al. (2007) "Submicron Particles of SBA-15 Modified with MgO as Carriers for Controlled Drug Delivery," *Chem. Pharm. Bull.* 55:985.
Sheraw et al. (2002) "Organic Thin-Film Transistor-Driven Polymer-Dispersed Liquid Crystal Displays on Flexible Polymeric Substrates," *Appl. Phys. Lett.* 80:1088-1090.
Shetty et al. (2005) "Formation and Characterization of Silicon Films on Flexible Polymer Substrates," *Mater. Lett.* 59:872-875.
Shi et al. (2001) "Free-Standing Single Crystal Silicon Nanoribbons," *J. Am. Chem. Soc.* 123(44):11095-11096.
Shi et al. (Sep. 2000) "Synthesis of Large Areas of Highly Oriented, Very Long Silicon Nanowires," *Adv. Mater.* 12(18):1343-1345.
Shimizu et al. (2012) "Letter: Zinc Oxide Paste as Sunscreen in the Postoperative Period," *Dermatologic Surgery* 38:965.

Shin et al. (2003) "PDMS-Based Micro PCR Chip with Parylene Coating," *J. Micromech. Microeng.* 13:768-774.
Shtein et al. (Oct. 15, 2004) "Direct Mask-Free Patterning of Molecular Organic Semiconductors Using Organic Vapor Jet Printing," *J. Appl. Phys.* 96(8):4500-4507.
Shull et al. (1998) "Axisymmetric Adhesion Tests of Soft Materials," *Macromol. Chem. Phys.* 199:489-511.
Siegel et al. (2009) "Lightweight, Foldable Thermochromic Displays on Paper," *Lab Chip* 9:2775-2781.
Siegel et al. (2010) "Foldable Printed Circuit Boards on Paper Substrates," *Adv. Funct. Mater.* 20:28-35.
Siegel et al. (Web Release Feb. 7, 2007) "Microsolidics: Fabrication of Three-Dimensional Metallic Microstructures in Poly(dimethylsiloxane)," *Adv. Mater.* 19(5):727-733.
Silvers et al. (2011) "Comparison and reproducibility of sEMG during manual muscle testing on land and in water," *Electromyogr. Kinesiol.* 21:95.
Sim et al. (1993) "An Analytical Back-Gate Bias Effect Model for Ultrathin SOI CMOS Devices," *IEEE Trans. Elec. Dev.* 40:755-765.
Sirringhaus et al. (2003) "Inkjet Printing of Functional Materials," *MRS Bull.* 28:802-806.
Sirringhaus et al. (Dec. 15, 2000) "High-Resolution Inkjet Printing of All-Polymer Transistor Circuits," *Science* 290:2123-2126.
Sirringhaus, H. (2005) "Device Physics of Solution-Processed Organic Field-Effect Transistors," *Adv. Mater.* 17:2411-2425.
Smay et al. (2002) "Colloidal Inks for Directed Assembly of 3-D Periodic Structures," *Langmuir* 18:5429-5437.
Smith et al. (2000) "Electric-Field Assisted Assembly and Alignment of Metallic Nanowires," *Appl. Phys. Lett.* 77(9):1399-1401.
Snow et al. (2003) "Random networks of carbon nanotubes as an electronic material," *Appl. Phys. Lett.*, vol. 82, No. 13, pp. 2145-2147.
Snow et al. (2005) "High-mobility carbon-nanotube transistors on a polymeric substrate," *Appl. Phys. Lett.*, 86, 033105.
So et al. (2008) Organic Light-Emitting Devices for Solid-State Lighting, *MRS Bull.* 33:663-669.
Sofia et al. (2001) "Functionalized Silk-Based Biomaterials for Bone Formation," *J. Biomed. Mater. Res.* 54:139-148.
Someya et al. (2005) "Conformable, Flexible, Large-Area Networks of Pressure and Thermal Sensors with Organic Transistor Active Matrixes," *Proc. Nat. Acad. Sci. USA* 102:12321-12325.
Someya et al. (2005) "Integration of Organic FETs with Organic Photodiodes for a Large Area, Flexible, and Lightweight Sheet Image Scanners," *IEEE Trans. Electron Devices* 52:2502-2511.
Someya et al. (Jul. 6, 2004) "A Large-Area, Flexible, Pressure Sensor Matric with Organic Field-Effect Transistors for Artificial Skin Applications," *Proc. Nat. Acad. Sci. USA* 101(27):9966-9970.
Someya, T. (Aug. 7, 2008) "Electronic Eyeballs," *Nature* 454:703-704.
Song et al. (2003) "Understanding Magnesium Corrosion—A Framework for Improved Alloy Performance," *Advanced Engineering Materials.* 5:837.
Song et al. (2009) "Mechanics of noncoplanar mesh design for stretchable electronic circuits," *Journal of Applied Physics.* 105:123516.
Soole et al. (Mar. 1991) "InGaAs Metal-Semiconductor-Metal Photodetectors for Long Wavelength Optical Communications," *IEEE J. Quantum Electron.* 27(3):737-752.
Soong et al. (1984) "Adverse Reactions to Virgin Silk Sutures in Cataract Surgery," *Ophthalmology* 91:479-483.
Sparks et al. (1978) "Investigating the MESA (multipoint electrotactile speech aid): the transmission of segmental features of speech," *Journal of the Acoustical Society of America.* 63:246-257.
Srinivasan et al. (Web Release Mar. 26, 2007) "Piezoelectric/Ultrananocrystalline Diamond Heterostructures for High-Performance Multifunctional Micro/Nanoelectromechanical Systems," *Appl. Phys. Lett.* 90:134101.
Stafford et al. (Aug. 2004) "A Buckling-Based Metrology for Measureing the Elastic Moduli of Polymeric Thin Films," *Nature Mater.* 3:545-550.
Staiger et al. (2006) "Magnesium and its Alloys as Orthopedic Biomaterials: A Review," *Biomaterials.* 27:1728.

(56) References Cited

OTHER PUBLICATIONS

Star et al. (2004) "Nanotube Optoelectric Memory Devices," *Nano Lett.*, vol. 4, No. 9, pp. 1587-1591.
Stathis et al. (2006) "The negative bias temperature instability in MOS devices: A review," *Microelec. Rel.* 46:270-286.
Stauth et al. (2006) "Self-assembled single-crystal silicon circuits on plastic," *Proc. Natl. Acad. Sci. USA* 19:13922-13927.
STELLA Project—Stretchable Electronics for Large-Area Applications. Available at www.stella-project.de. Accessed Feb. 8, 2012.
Storm et al. (Aug. 2003) "Fabrication of Solid-State Nanopores with Single-Nanometre Precision," *Nat. Mater.* 2:537-540.
Streetman et al. (2000) "Intrinsic Material," In; *Solid State Electronic Devices*, $5^{th}$ Ed., Prentice Hall; Upper Saddle River, NJ; pp. 74-75.
Stroop (1935) "Studies of Interference in Serial Verbal Reactions," *Journal of Experimental Psychology.* 18:643-662.
Strukov et al. (2005) "CMOL FPGA: A Reconfigurable Architecture for Hybrid Digital Circuits with Two-Terminal Nanodevices," *Nanotechnology* 16:888-900.
Su et al. (2000) "Lattice-Oriented Growth of Single-Walled Carbon Nanotubes," *J. Phys. Chem. B* 104(28):6505-6508.
Su et al. (2012) "Postbuckling Analysis and its Application to Stretchable Electronics," *Journal of the Mechanics and Physics of Solids.* 60:487.
Sum et al. (2009) "Near-Infrared Spectroscopy for the Detection of Lipid Core Coronary Plaques," *Curr. Cardiovasc. Imag. Rep.* 2:307-315.
Sumant et al. (Apr. 2005) "Toward the Ultimate Tribological Interface: Surface Chemistry and Nanotribology of Ultrananocrystalline Diamond," *Adv. Mater.* 17(8):1039-1045.
Sun et al. (2004) "Fabricating Semiconductor Nano/Microwires and Transfer Printing Ordered Arrays of Them onto Plastic Substrates," *Nano Lett.* 4:1953-1959.
Sun et al. (2005) "Advances in Organic Field-Effect Transistors," *J. Mater. Chem.* 15:53-65.
Sun et al. (2005) "Bendable GaAs Metal-Semiconductor Field-Effect Transistors Formed with a Printed GaAs Wire Arrays on Plastic Substrates," *Appl. Phys. Lett.* 87:083501.
Sun et al. (2005) "Photolithographic Route to the Fabrication of Micro/Nanowires of III-V Semiconductors," *Adv. Fuct. Mater.* 15:30-40.
Sun et al. (2007) "Controlled Buckling of Semiconductor Nanoribbons for Stretchable Electronics," *Nat. Nanotechnol.* 1:201-207.
Sun et al. (2007) "Structural Forms of Single Crystal Semiconductor Nanoribbons for High-Performance Stretchable Electronics," *J. Mater Chem.* 17:832-840.
Sun et al. (Aug. 2007) "Inorganic Semiconductors for Flexible Electronics," *Adv. Mater.* 19(15):1897-1916.
Sun et al. (Nov. 2006) "Buckled and Wavy Ribbons of GaAs for High-Performance Electronics on Elastomeric Substrates," *Adv. Mater.* 18(21):2857-2862.
Sunaga et al. (2002) "Measurement of the electrical properties of human skin and the variation among subjects with certain skin conditions," *Phys. Med. Biol.* 47:N11-N15.
Sundar et al. (2004) "Elastomeric Transistor Stamps: Reversible Probing of CHaarge Transport in Organic Crystals," *Science* 303:1644-1646.
Suo et al. (Feb. 22, 1999) "Mechnics of Rollable and Foldable Film-on-Foil Electronics," *Appl. Phys. Lett.* 74(8):1177-1179.
Supplementary European Search Report Corresponding to European Patent Application No. 07 84 1968, Completed Mar. 31, 2011.
Supplementary European Search Report Corresponding to European Patent Application No. 10 842 518, Completed Aug. 9, 2013.
Supplementary European Search Report, Corresponding to European Application No. 04 81 2651, Completed Oct. 19, 2010.
Supplementary European Search Report, Corresponding to European Application No. 05 75 6327, Completed Sep. 25, 2009.
Swain et al. (2004) "Curved CCD Detector Devices and Arrays for Multi-Spectral Astrophysical Application and Terrestrial Stereo Panoramic Cameras," *Proc. SPIE* 5499:281-301.
Sze et al. (1985) *Semiconductor Devices, Physics and Technology*, $2^{nd}$ ed., Wiley, New York, pp. 190-192.
Sze, S. (1985) *Semiconductor Devices: Physics and Technology*, New York: Wiley, pp. 428-467.
Sze, S. (1988) *VLSI Technology*, Mcgraw-Hill, 327-374, 566-611.
Sze, S. (1994) *Semiconductor Sensors*, John Wiley and Sons: New York, pp. 17-95.
Tagami et al. (1980) "Evaluation of the Skin Surface Hydration In Vivo by Electrical Measurement," *J. Investig. Dermatol.* 75:500-507.
Taheri et al. (1994) "A dry electrode for EEG recording, Electro-encephalography and clinical neurophysiology," 90(5):376-383.
Takagi et al. (1994) "On the Universality of Inversion Layer Mobility in Si MOSFET's: Part II—Effects on Surface Orientation," *IEEE Trans. Electron Dev.* 41:2363-2368.
Takamoto et al. (Jan. 20, 1997) "Over 30% Efficient InGaP/GaAs Tandem Solar Cells," *Appl. Phys. Lett.* 70(3):381-383.
Takei et al. (2010) "Nanowire Active-Matrix Circuitry for Low-Voltage Macroscale Artificial Skin," *Nat. Mater.* 9:821.
Takema et al. (1994) "Age-related changes in the elastic properties and thickness of human facial skin," *Brit. J. Dermatol.* 131:641-648.
Talapin et al. (Oct. 7, 2005) "PbSe Nanocrystal Solids for n- and p-Channel Thin Film Field-Effect Transistors," *Science* 310:86-89.
Tan et al. (1999) "Information Transmission with a Multifinger Tactual Display," *Perception & Psychophysics.* 61:993-1008.
Tan et al. (2010) "Hydration effects on skin microstructure as probed by high-resolution cryo-scanning electron microscopy and mechanistic implications to enhanced transcutaneous delivery of biomacromolecules," *J. Pharm. Sci.* 99:730-740.
Tan et al. (Apr. 12, 2004) "Performance Enhancement of InGaN Light Emitting Diodes by Laser-Lift-off and Transfer from Sapphire to Copper Substrate," *Appl. Phys. Lett.* 84(15):2757-2759.
Tanase et al. (2002) "Magnetic Trapping and Self-Assembly of Multicomponent Nanowires," *J. Appl. Phys.* 91:8549-8551.
Tang et al. (2005) "One-Dimensional Assemblies of Nanoparticles: Preparation, Properties, and Promise," *Adv. Mater.* 17:951-962.
Tao et al. (2003) "Langmuir-Blodgett Silver Nanowire Monolayers for Molecular Sensing Using Surface-Enhanced Raman Spectroscopy," *Nano Lett.* 3:1229-1233.
Tate et al. (2000) "Anodization and Microcontact Printing on Electroless Silver: Solution-Based Fabrication Procedures for Low-Voltage Electronic Systems with Organic Active Components," *Langmuir* 16:6054-6060.
Tchvialeva et al. (2010) "Skin Roughness Assessment," In; New Developments in Biomedical Engineering. D. Campolo: Eds. InTech. p. 341-358.
Teshima et al. (2001) "Room-Temperature Deposition of High-Purity Silicon Oxide Films by RF Plasma-Enhanced CVD," *Surf. Coat. Technol.* 146-147:451-456.
Theiss et al. (1998) "PolySilicon Thin Film Transistors Fabricated at 100° C. on a Flexible Plastic Substrate," *IEDM* 98:257-260.
Thornwood et al. (Oct. 1, 1990) "Utilizing Olptical Lithography in the Sub-Micron Dimensional Regime," *IBM Tech. Disc. Bull.* 33(5):187-188.
Timko et al. (2009) "Electrical Recording from Hearts with Flexible Nanowire Device Arrays," *Nano Lett.* 9:914-918.
Toader et al. (2004) "Photonic Band Gap Architectures for Holographic Lithography," *Phy. Rev. Lett.* 043905/1-043905/4.
Toader et al. (2004) "Photonic Band Gaps Based on Tetragonal Lattices of Slanted Pores," *Phys. Rev. Lett.* 90:233901/1-233901/4.
Tong (1999) *Semiconductor Wafer Bonding: Science and Technology*, John Wiley; New York, pp. 187-221.
Trau et al. (1997) "Microscopic Patterning of Orientated Mesoscopic Silica Through Guided Growth," *Nature* 390:674-676.
Trentler et al. (1995) "Solution-Liquid-Solid Growth of Crytalline III-V Semiconductors: An Analogy to Vapor-Liquid-Solid Growth," *Science* 270:1791-1794.
Trewyn et al. (2008) "Biocompatible Mesoporous Silica Nanoparticles with Different Morphologies for Animal Cell Membrane Penetration," *Chemical Engineering Journal.* 137:23.

(56) References Cited

OTHER PUBLICATIONS

Tseng et al. (Web Release Dec. 19, 2003) "Monolithic Integration of Carbon Nanotube Devices with Silicon MOS Technology" *Nano Lett.* 4(1):123-127.
Ucjikoga, S. (2002) "Low-Temperature Polycrystalline Silicon Thin-Film Transistor Technologies ofr System-on-Glass Displays," *MRS Bull.* 27:881.
Urruchi et al. (2000) "Etching of DLC Films Using a Low Intensity Oxygen Plasma Jet," *Diamond Relat. Mater.* 9:685-688.
Valtiner et al. (2008) "Stabilization and acidic dissolution mechanism of single crystalline ZnO(0001) surfaces in electrolytes studied by in-situ AFM imaging and ex-situ LEED," *Langmuir.* 24:5350.
Vanhollenbeke et al. (2000) "Compliant Substrate Technology: Integration of Mismatched Materials for Opto-Electronic Applications," *Prog. Cryst Growth Charact. Mater.* 41(1-4):1-55.
Velev et al. (1997) "Porous silica via colloidal crystallization," *Nature* 389:447-448.
Vepari et al. (Aug. Sep. 2007) "Silk as a Biomaterial," *Prog. Polym. Sci.* 32(8-9):991-1007.
Verdier-Sévrain et al. (2007) "Skin hydration: a review on its molecular mechanisms," *J. Cosmet. Dermatol.*6:75-82.
Vidal-Verdu et al. (2007) "Graphical Tactile Displays for Visually-Impaired People," *IEEE Transactions on Neural Systems and Rehabilitation Engineering.* 15:119-130.
Vilan et al. (2000) "Molecular Control Over Au/GaAs Diodes," *Nature* 404:166-168.
Vinck et al. (2003) "Increased Fibroblast Proliferation Induced by Light Emitting Diode and Low Power Laser Irradiation," *Lasers Med. Sci.* 18:95-99.
Viventi et al. (2011) "Flexible, Foldable, Actively Multiplexing, High Density Electrode Array for Mapping Brain Activity In Vivo," *Nature Neuroscience.* 14:1599-1605.
Viventi et al. (Mar. 2010) "A Conformal, Bio-Interfaced Class of Silicon Electronics for Mapping Cardiac Electrophysiology," *Sci. Trans. Med.* 2(24):24ra22.
Vlasov et al. (2001) "On-Chip Natural Assembly of Silicon Photonic Bandgap Crystals," *Nature* 414:289-293.
Voss, D. (2000) "Cheap and Cheerful Circuits," *Nature* 407:442-444.
Vuillerme et al. (2008) "Sensory Supplementation System Based on Electrotactile Tongue Biofeedback of Head Position for Balance Control," *Neurosci. Lett.* 431:206-210.
Wagner et al. (2003) "Silicon for Thin-Film Transistors," *Thin Solid Films* 430:15-19.
Wagner et al. (2005) "Electronic Skin: Architecture and Components," *Physica E* 25:326-334.
Wagner et al. (Mar. 1, 1964) "Vapor-Liquid-Solid Mechanism of Single Crystal Growth," *Appl. Phys. Lett.* 4(5):89-90.
Waksman et al.(2008) "Photopoint Photodynamic Therapy Promotes Stabilization of Atherosclerotic Plaques and Inhibits Plaque Progression," *J. Am. Coll. Cardiol.* 52:1024-1032.
Wales et al. (2003) "Stationary Points and Dynamics in High-Dimensional Systems," *J. Chem. Phys.* 119:12409.
Wang (May 2012) "Mechanics of Epidermal Electronics," *Journal of Applied Mechanics.* 79:031022.
Wang et al. (1999) "Electromechanical Coupling and Output Efficiency of Piezoelectric Bending Actuators," *IEEE transactions on Ultrasonics, Ferroelectrics and Frequency Control.* 46:638.
Wang et al. (2003) "A Solution-Phase, Precursor Route to Polycrystalline $SnO_2$ Nanowores that can be Used for Gas Sensing under Ambient Conditions," *J. Am. Chem. Soc.* 125:16176-16177.
Wang et al. (2005) "Electronically Selective Chemical Functionalization of Carbon Nanotubes: Correlation between Raman Spectral and Electrical Responses," *J. Am. Chem. Soc.*, 127:11460-11468.
Wang et al. (2005) "Oxidation Resistant Germanium Nanowires: Bulk Synthesis, Long Chain Alkanethiol Functionalization, and Langmuir-Blodgett Assembly," *J. Am. Chem. Soc.* 127(33):11871-11875.
Wang et al. (2006) "Direct Synthesis and Characterization of CdS Nanobelts," *Appl. Phys. Lett.* 89:033102.
Wang et al. (Aug.-Sep. 2008) "In Vivo Degradation of Three-Dimensional Silk Fibroin Scaffolds," *Biomaterials* 29(24-25):3415-3428.
Warren et al. (2008) "Receptive Field Characteristics Under Electrotactile Stimulation of the Fingertip," *IEEE Transactions on Neural Systems and Rehabilitation Engineering.* 16:410-415.
Waxman et al. (2009) "In vivo Validation of a Catheter-Based Near-Infrared Spectroscopy System for Detection of Lipid Core Coronary Plaques: Initial Results of the Spectacl Study," *J. Am. Coll. Cardiol. Img.* 2:858-868.
Waxman, S. (2008) "Near-Infrared Spectroscopy for Plaque Characterization," *J. Interv. Cardiol.* 21:452-458.
Weber et al. (Jan. 2004) "A Novel Low-Cost, High Efficiency Micromachined Silicon Solar Cell," *IEEE Electron Device Lett.* 25(1):37-39.
Wegnera et al. (2006) "In situ formation and hydrolysis of Zn nanoparticles for $H_2$ Production by the 2-Step ZnO/Zn Water-Splitting Thermochemical Cycle," *International Journal of Hydrogen Energy.* 31:55.
Wen et al. (Web Release Dec. 4, 2004) "Controlled Growth of Large-Area, Uniform, Vertically Aligned Arrays of $\alpha$-$Fe_2O_2$ Nanobelts and Nanowires," *J. Phys. Chem. B* 109(1):215-220.
Whang et al. (2003) "Large-Scale Hierarchical Organization of Nanowire Arrays for Integrated Nanosystems," *Nano Lett.* 3(9):1255-1259.
Williams et al. (Oct. 2006) "Growth and Properties of Nanocrystalline Diamond Films," *Phys. Stat. Sol. A* 203(13):3375-3386.
Williams et al. (Web Release Jan. 23, 2006) "Comparison of the Growth and Properties of Ultranocrystalline Diamond and Nanocrystalline Diamond," *Diamond Relat. Mater.* 15:654-658.
Willner et al. (2002) "Functional Nanoparticle Architectures for Senoric, Optoelectronic, and Bioelectronic Applications," *Pure Appl. Chem.* 74(9):1773-1783.
Wilson et al. (2006) "ECoG Factors Underlying Multimodal Control of a Brain-Computer Interface," *IEEE Trans. Neural Syst. Rehabil. Eng.* 14:246-250.
Wind et al. (May 20, 2002) "Vertical Scaling of Carbon Nanotube-Field-Effect Transitors Using Top Gate Electrodes," *Appl. Phys. Lett.* 80(20):3871-3819.
Wise et al. (Jul. 2008) "Microelectrodes, Microelectronics, and Implantable Neural Microsystems," *Proc. IEEE* 96(7):1184-1202.
Won et al. (2004) "Effect of Mechanical and Electrical Stresses on the Performance of an a-Si:H TFT on Plastic Substrate," *J. Electrochem. Soc.* 151:G167-G170.
Won et al. (2011) "Piezoresitive Strain Sensors and Multiplexed Arrays Using Assemblies of Single-Crystalline Silicon Nanoribbons on Plastic Substrates," *IEEE Transactions on Electron Devices.* 58:4074-4078.
Wong-Riley et al. (2005) "Photobiomodulation Directly Benefits Primary Neurons Functionally Inactivated by Toxins," *J. Biol. Chem.* 280:4761-4771.
Woo et al. (1992) "Skin Impedance Measurements Using Simple and Compound Electrodes," *Medical & Biological Engineering & Computing.* 30:97-102.
Woodburn et al. (1996) "Phototherapy of Cancer and Atheromatous Plaque with Texaphyrins," *J. Clin. Laser Med. Surg.* 14:343-348.
Wu et al. (2001) "Amorphous Silicon Crystallization and Polysilicon Thin Film Transistors on $SiO2$ Passivated Steel Foil Substrates," *Apple. Surf. Sci* 175-176:753-758.
Wu et al. (2001) "Direct Observation of Vapor-Liquid-Solid Nanowire Growth," *J. Am. Chem. Soc.* 123(13):3165-3166.
Wu et al. (2001) "Thermal Oxide of Polycrystalline Silicon on Steel Foil as a Thin-Film Transistor Gate Dielectric," *Appl. Phys. Lett.* 78:3729-2731.
Wu et al. (2002) "Block-by-Block Growth of Single-Crystalline Si/SiGe Superlattice Nanowires," *Nano Lett.* 2(2):83-86.
Wu et al. (2002) "Growth of Au-Catalyzed Ordered GaAs Nanowire Arrays by Molecular-Beam Epitaxy," *Appl. Phys. Lett.* 81:5177-5179.

(56) References Cited

OTHER PUBLICATIONS

Wu et al. (2002) "Inorganic Semiconductor Nanowires: Rational Growth, Assembly, and Novel Properties," *Chem. Eur. J.* 8(6):1261-1268.
Wu et al. (2003) "Growth, Branching, and Kinking of Molecular-Beam Epitaxial (110) GaAs Nanowires," *Appl. Phys. Lett.* 83:3368-3370.
Wu et al. (Jul. 1, 2004) "Single-Crystal Metallic Nanowires and Metal/Semiconductor Nanowire Heterostructures," *Nature* 430:61-65.
Wu et al. (Nov. 2002) "Complementary Metal-Oxide-Semiconductor Thin-Film Transistor Circuits from a High-Temperature Polycrystalline Silicon Process on Steel Foil Substrates," *IEEE Trans. Electr. Dev.* 49(11):1993-2000.
Xia (1998) "Soft Lithography" *Angew. Chem. Int. Ed.* 37:551-575.
Xia et al. (1996) "Shadowed Sputtering of Gold on V-Shaped Microtrenches Etched in Silicon and Applications in Microfabrication," *Adv. Mater.* 8(9):765-768.
Xia et al. (1998) "Soft Lithography," *Annu. Rev. Mater. Sci.* 28:153-184.
Xia et al. (1999) "Unconventional Methods for Fabricating and Patterning Nanostructures," *Chem. Rev.* 99:1823-1848.
Xia et al. (2003) "One-Dimensional Nanostructures: Synthesis, Characterization and Applications," *Adv. Mater.* 15:353-389.
Xia et al. (Jul. 19, 1996) "Complex Optical Surfaces Formed by Replica Molding Against Elastomeric Masters," *Science* 273:347-349.
Xiang et al. (Mar. 25, 2006) "Ge/Si Nanowire Heterostructures as High-Performance Field-Effect Transistors," *Nature* 441:489-493.
Xiao et al. (2003) "High-mobility thin-film transistors based on aligned carbon nanotubes," *Appl. Phys. Lett.*, vol. 83, No. 1, pp. 150-152.
Xiao et al. (2010) "Opto-thermal in-vivo skin hydration measurements? A comparison study of different measurement techniques," *J. Phys: Conf. Ser.* 214:012026.
Xie et al. (May 2003) "Polymer-Controlled Growth of $Sb_2Se_3$ Nanoribbons Via a Hydrothermal Process," *J. Cryst. Growth* 252(4):570-574.
Xin et al. (Jun. 2005) "Evaluation of Polydimethylsiloxane Scaffolds with Physiologically-Relevant Elastic Moduli: Interplay of Substrate Mechanics and Surface Chemistry Effects on Vascular Smooth Muscle Cell Response," *Biomaterials* 26(16):3123-3129.
Yamamoto et al. (1976) "Electrical properties of the epidermal stratum corneum," *Med. Biol. Eng.* 14:151-158.
Yang et al. (1997) "Mesoporous Silica with Micrometer-Scale Desgns," *Adv. Mater.* 9:811-814.
Yang et al. (2000) "Stability of Low-Temperature Amorphous Silicon Thin Film Transistors Formed on Glass and Transparent Plastic Substrates," *J. Vac. Sci. Technol. B* 18:683-689.
Yang et al. (2002) "Creating Periodic Three-Dimensional Structures by Multibeam Interface of Visible Laser," *Chem. Mater.* 14:2831-2833.
Yang et al. (Dec. 2007) "RFID Tag and RF Structures on a Paper Substrate Using Inkjet-Printing Technology," *IEEE Trans. Microw. Theory Tech.* 55(12):2894-2901.
Yang, P. (2005) "The Chemistry and Physics of Semiconductor Nanowires," *MRS Bull.* 30:85.
Yanina et al. (2002) "Terraces and ledges on (001) spinel surfaces," *Surf. Sci.*, 513:L402-L412.
Yao et al. (2008) "Seeing Molecules by Eye: Surface Plasmon Resonance Imaging at Visible Wavelengths with High Spatial Resolution and Submonolayer Sensitivity," *Angew. Chem.* 47:5013-5017.
Yao et al. (2010) "Functional Nanostructured Plasmonic Materials," *Adv. Mater.* 22:1102-1110.
Yao et al. (Mar. 2000) "High-Field Effect Electrical Transport in Single-Walled Carbon Nanotubes," *Phys. Rev. Lett.* 84(13):2941-2944.

Yeager et al. (Aug. 30, 2008) "Characterization of Flexible ECoG Electrode Arrays for Chronic Recording in Awake Rats," *J. Neurosci. Methods* 173(2):279-285.
Yeh et al. (1994) "Fluidic Self-Assembly for the Integration of GaAs Light Emitting Diodes on Si Substrates," *IEEE Photon. Techn. Lett.* 6:706-708.
Yeo et al. (Feb. 26, 2013) "Multifunctional Epidermal Electronics Printed Directly Onto the Skin," *Advanced Materials.* 25:2773-2778.
Yin et al. (2000) "A Soft Lithography Approach to the Fabrication of Nanostructures of Single Crystalline Silicon with Well-Defined Dimensions and Shapes," *Adv. Mater.* 12:1426-1430.
Yin et al. (2005) "Colloidal Nanocrystal Synthesis and the Organic-Inorganic Interface," *Nature* 437:664-670.
Ying et al. (Mar. 27, 2012) "Silicon Nanomembranes for Fingertip Electronics," *Nanotechnology.* 23: 344004.
Yoon et al. (2005) "Low-Voltage Organic Field-Effect Transistors and Inverters Enabled by Ultrathin Cross-Linked Polymers as Gate Dielectrics," *J. Am. Chem. Soc.* 127:10388-10395.
Yu et al. (2000) "Silicon Nanowires: Preparation, Device Fabrication, and Transport Properties," *J. Phys. Chem. B* 104(50):11864-11870.
Yu et al. (2003) "Solution-Liquid-Solid Growth of Soluble GaAs Nanowires," *Adv. Mater.* 15:416-419.
Yu et al. (2003) „ Two-Versus Three-Dimensional Quantum Confinement in Indium Phosphide Wires and Dots, *Nat. Mater.* 2:517-520.
Yu et al. (2004) "The Yield Strength of Thin Copper Films on Kapton," *J. Appl. Phys.* 95:2991-2997.
Yu et al. (2007) "Micropatterning Metal Electrode of Organic Light Emitting Devices Using Rapid Polydimethylsiloxane Lift-Off," *Appl. Phys. Lett.* 91:043102.
Yu et al. (2009) "A Microfabricated Electrode with Hollow Microneedles for ECG Measurement," *Sens. Actuators A.* 151:17-22.
Yuan et al. (2006) "High-Speed Strained-Single-Crystal-Silicon Thin-Film Transistors on Flexible Polymers," *J. Appl. Phys.* 100:013708.
Yurelki et al. (Jul. 24, 2004) "Small-Angle Neutron Scattering from Surfactant-Assisted Aqueous Dispersions of Carbon Nanotubes," *J. Am. Chem. Soc.* 126(32):9902-9903.
Zakhidov et al. (1998) "Carbon Structure with Three-Dimensional Periodicity at Optical Wavelengths," *Science* 282:897-901.
Zaumseil et al. (2003) "Nanoscale Organic Transistors that use Source/Drain Electrodes Supported by High Resolution Rubber Stamps," *Appl. Phys. Lett.* 82(5):793-795.
Zaumseil et al. (2003) "Three-Dimensional and Multilayer Nanostructures Formed by Nanotransfer Printing," *Nano Lett.* 3(9):1223-1227.
Zhai et al. (2012) "High-Performance Flexible Thin-Film Transistors Exfoliated from Bulk Wafer," *Nano Lett.* 12:5609-5615.
Zhang et al. (1999) "In vivo friction properties of human skin," *Prosthet. Orthot. Int.* 23:135-141.
Zhang et al. (2001) "Electric-field-directed growth of aligned single-walled carbon nanotubes," *Appl. Phys. Lett.*, vol. 79, No. 19. pp. 3155-3157.
Zhang et al. (2005) "Low-Temperature Growth and Photoluminescence Property of ZnS Nanoribbons," *J. Phys. Chem. B* 109(39):18352-18355.
Zhang et al. (2006) "Anomalous Coiling of SiGe/Si and SiGe/Si/Cr Helical Nanobelts," *Nano Lett.* 6(7):1311-1317.
Zhang et al. (2010) "Amphiphilic copolymers for liquid bandage application studies," *Front. Biosci.* 2:1123-1133.
Zhang et al. (2010) "Fabrication and Comparative Study of Top-Gate and Bottom-Gate ZnO-TFTs with Various Insulator Layers," *J. Mater. Sci: Mater. Electron.* 21:671.
Zhang et al. (Apr. 2003) "Oxide-Assisted Growth of Semiconducting Nanowires," *Adv. Mater.* 15(7-8):635-640.
Zhang et al. (Apr. 5, 2004) "Structure and Photoluminescence of ZnSe Nanoribbons Grown by Metal Organic Chemical Vapor Deposition," *Appl. Phys. Lett.* 84(14):2641-2643.

(56) References Cited

OTHER PUBLICATIONS

Zhang et al. (Feb. 9, 2006) "Electronic Transport in Nanometre-Scale Silicon-on-Insulator Insulator Membranes," *Nature* 439:703-706.
Zhao et al. (2004) "Piezoelectric Characterization of Individual Zinc Oxide Nanobelt Probed by Piezoresponse Force Microscopy," *Nano Lett.* 4:587.
Zhao et al. (Mar. 2007) "Improved Field Emission Properties from Metal-Coated Diamond Films," *Diamond Relat Mater.* 16(3):650-653.
Zheng et al. (1998) "Sudden Cardiac Death in the United States, 1989 to 1998," *Circulation* 104, 2158-2163 (1998.
Zheng et al. (2004) "Shape-and Solder-Directed Self-Assembly to Package Semiconductor Device Segments," *Appl. Phys. Lett.* 85:3635-3637.
Zheng et al. (2009) "In Vitro and In Vivo Biocompatibility Studies of ZnO Nanoparticles," *International Journal of Modern Physics B.* 23:1566.
Zheng et al. (Aug. 31, 2004) "Sequential Shape-and-Solder-Directed Self Assembly of Functional Microsystems," *Proc. Natl. Acad. Sci. USA* 101(35):12814-12817.
Zhou et al. (2002) "An Efficient Two-Photon-Generated Photoacid Applied to Positive-Tone 3D Microfabrication," *Science* 296:1106-1109.
Zhou et al. (2004) "p-Channel, n-Channel Thin Film Transistors and p-n Diodes Based on Single Wall Carbon Nanotube Networks," *Nano Lett.* 4:2031-2035.
Zhou et al. (2005) "Band Structure, Phonon Scattering, and the Performance Limit of Single-Walled Carbon Nanotube Transistors," *Phys. Rev. Lett.* 95:146805.
Zhou et al. (2005) "Mechanism for Stamp Collapse in Soft Lithography," *Appl. Phys. Lett.* 87:251925.
Zhou et al. (2006) "Dissolving Behavior and Stability of ZnO Wires in Biofluids: A Study on Biodegradability and Biocompatibility of ZnO Nanostructures," *Adv. Mater.* 18:2432.
Zhou et al. (2013) "Fast Flexible Electronics with Strained Silicon Nanomembranes," *Scientific Reports.* 3:1291.
Zhu et al. (2005) "Spin on Dopants for High-Performance Single Crystal Silicon Transistors on Flexible Plastic Substrates," *Appl. Phys. Lett.* 86(133507)1-3.
Zhu et al. (2010) "Flexible High-Output Nanogenerator Based on Lateral ZnO Nanowire Array," *Nano Lett.* 10:3151.
Zipes et al. (2006) "ACC/AHA/ESC 2006 Guidelines for Management of Patients With Ventricular Arrhythmias and the Prevention of Sudden Cardiac Death: A Report of the American College of Cardiology/American Heart Association Task Force and the European Society of Cardiology Committee for Practice Guidelines (Writing Committee to Develop Guidelines for Management of Patients With Ventricular Arrhythmias and the Prevention of Sudden Cardiac Death," *Circulation* 114:385-484.

\* cited by examiner

APPENDAGE MOUNTABLE ELECTRONIC DEVICES CONFORMABLE TO SURFACES

CROSS-REFERENCE TO RELATED APPLICATIONS

This application claims benefit to U.S. Provisional Patent Application Nos. 61/794,004 filed Mar. 15, 2013, 61/636,527 filed Apr. 20, 2012 and 61/618,371 filed Mar. 30, 2012, each of which are incorporated by reference to the extent not inconsistent herewith.

STATEMENT REGARDING FEDERALLY SPONSORED RESEARCH OR DEVELOPMENT

This invention was made with government support under CMMI-0328162 and awarded by the National Science Foundation, and DE-FG02-07ER46471 and DE-FG02-07ER46453 awarded by the Department of Energy. The government has certain rights in the invention.

BACKGROUND OF INVENTION

Physiological measurement and stimulation techniques that exploit interfaces to the skin have been of interest for many years. Despite much progress over this time, nearly all associated device technologies continue to rely on conceptually old designs. Typically, small numbers of bulk electrodes are mounted on the skin via adhesive tapes, mechanical clamps/straps and/or penetrating needles, often mediated by conductive gels, with terminal connections to separate boxes that house collections of rigid circuit boards, power supplies and communication components. These systems have many important capabilities, but they are poorly suited for practical application outside of research labs or clinical settings, due to difficulties in establishing long-lived, robust electrical contacts that do not irritate the skin, and in achieving integrated systems with overall sizes, weights and shapes that do not cause discomfort during prolonged use.

Recently, a number of patents and publications have disclosed flexible, resilient and implantable electrode arrays. For example, U.S. Patent Application Publication US 2007/0043416 discloses an implantable flexible elastic support with a plurality of electrodes held in contact with a target tissue. Similarly, International Patent Application Publication WO 98/49936 discloses a resilient electrode array for sensing signals associated (mapping) and ablating heart tissue. U.S. Pat. No. 5,678,737 discloses an electrophysiology mapping system for displaying a 3D model of epicardial and endocardial surfaces with dynamic display of potential distribution data.

U.S. Patent Application Publication US 2003/0149456 discloses a multi-electrode cardiac lead adapter which incorporates a multiplexing circuit allowing for control by a conventional single lead cardiac pacing pulse generator. Similarly, U.S. Patent Application Publication US 2006/0173364 discloses a multichannel electrophysiology acquisition system which utilizes a digital multiplexing circuit build on a conventional integrated circuit. U.S. Pat. No. 6,666,821 discloses an implantable sensor array system with an associated protective member which prevents the sensors from interacting with the surrounding environment until it is disabled.

International Application Publication WO 2009/114689 and U.S. Patent Publication No. 2013/0041235, each of which are individually hereby incorporated by reference in its entirety, discloses flexible and scalable sensor arrays for recording and modulating physiologic activity. US Patent Application Publication Nos. US 2008/0157235, US 2008/0108171, US 2010/0002402 and U.S. Pat. No. 7,557,367 issued Jul. 7, 2009, all of which are hereby incorporated by reference in their entireties, disclose multilayer stretchable, foldable and printable semiconductor devices.

There is a need in the art for high-fidelity, robust and reliable electronics on surfaces that are capable of accommodating any type of curved surface, including highly complex shapes such as those associated with moving fingers. One difficulty with providing electronics to interact with such complex surface shapes is that it can be difficulty to reliably provide electronics in a correspondingly complex surface shape so as to achieve good interaction between the electronics and the complex surface shape over a large contact area. Provided herein are various devices and methods that address this aspect.

SUMMARY OF THE INVENTION

Provided herein are devices and methods related to ultra-thin flexible and stretchable electronics that may be incorporated with flexible surfaces to permit electrical interfacing with a range of surfaces and surface shapes, including highly irregular shaped surfaces that may change shape over time. In an embodiment, the invention is an electronic device having an enclosure that is shaped to cover and conform to a curved surface, including a fully three-dimensionally varying surface having complex shapes with at least one surface that faces another surface, such as an appendage of a person that moves and changes shape with movement. Alternatively, the appendage may be part of a non-living instrument or inanimate object, such as a remote sensing device or robotic instrument.

In an aspect, the invention provides an appendage mountable electronic system, the system comprising: (i) a flexible or stretchable substrate having an inner surface and an outer surface, wherein the inner surface defines an enclosure capable of receiving an appendage having a curved surface; and (ii) a flexible or stretchable electronic device comprising one or more sensors, actuators or both supported by the inner surface or the outer surface of the flexible or stretchable substrate; the sensors, actuators or both comprising one or more inorganic semiconductor components, one or more metallic components, or one or more inorganic semiconductor components and one or more metallic components; wherein at least a portion of the inorganic semiconductor components, metallic components or both has a thickness less than or equal to 500 microns; wherein the flexible or stretchable substrate and the electronic device provide a net bending stiffness of the system low enough such that the inner surface of the substrate is capable of establishing conformal contact with a surface of the appendage provided within the enclosure. In an embodiment, for example, the appendage is a hand, a finger, a finger-tip, a skull, a foot, a toe, a leg, a torso, or any portion thereof. In an embodiment, for example, the system of the invention comprises an instrumented glove for covering a hand or an instrumented finger-tube for covering a finger or finger-tip, such as a medical glove for surgery. In an embodiment, for example, the system of the invention comprises a human-machine interface system. In an embodiment, for example, the system of the invention comprises a device for robotic manipulation.

In an embodiment, for example, the flexible or stretchable substrate and the electronic device provide the net bending stiffness of the system less than or equal to $1 \times 10^8$ GPa $\mu m^4$.

In an embodiment, for example, the net bending stiffness of the device is low enough such that the one or more sensors, actuators or both supported by the inner surface of the substrate are capable of establishing conformal contact with the surface of the appendage provided within the enclosure. In an embodiment, for example, the flexible or stretchable substrate and the electronic device provide a net flexural rigidity of the system less than or equal to $1 \times 10^{-4}$ Nm. In an embodiment, for example, the substrate is a flexible substrate and the electronic device is a flexible electronic device. In an embodiment, for example, the substrate is a stretchable substrate and device is a stretchable electronic device. In an embodiment, for example, the system is characterized by a neutral mechanical plane and wherein at least a portion of the one or more inorganic semiconductor components, or the one or more metallic components or both are positioned proximate to the neutral mechanical plane. In an embodiment, a strain-sensitive material, including the material having a mechanical property that is most sensitive to an applied strain, is positioned coincident or, alternatively, proximate to, the neutral mechanical plane.

Any of the systems provided herein may have from between about 2 to about 1000 of sensors, actuators or both. In an embodiment, the electronic device comprises at least 3 different types of sensors, actuators or both. In an aspect, the one or more sensors, actuators or both are provided in an open mesh geometry.

Any of the systems are optionally described in terms of a footprint surface area of the one or more sensors, actuators or both. In an embodiment, the footprint surface area is selected from the range of 0.5 cm$^2$ to 100 cm$^2$. In an aspect, the footprint surface area corresponds to an array of sensors, actuators or both, wherein individual sensors or actuators have relatively small individual footprints, but the members of the array are spread to provide a desired footprint, including larger area footprints. Accordingly, depending on the application of interest, such as the surface area of the appendage being interfaced with, the footprint area is correspondingly selected. In this manner, a finger-tip appendage system may have a footprint surface area in the 0.5 cm$^2$ to about 2 cm$^2$, whereas for an arm, leg, or head, the footprint surface area may be desirably larger such as 10 cm$^2$ to 100 cm$^2$.

The systems provided herein are compatible with a large range of sensors, depending on the application of interest. Examples include one or more sensors selected from the group consisting of an electrode, a tactile sensor, a strain gauge, a capacitance sensor, a temperature sensor, a pressure sensor, a motion sensor, a position sensor, a displacement sensor, an acceleration sensor, a force sensor, a chemical sensor, a pH sensor, a capacitive sensor, an optical sensor, a photodetector, a hydration sensor, an imaging system and any arrays and combinations thereof.

The systems provided herein are compatible with a large range of actuators, depending on the application of interest. Examples include one or more actuators selected from the group consisting of an electrotactile stimulator, an electrode, a heat source (thermal actuator), a piezoelectric element, an acoustic element, a source of RF energy, a magnetic actuator, a source of electromagnetic radiation, a laser, a light source, a light emitting diode and arrays, and any arrays and combinations thereof.

In an embodiment, at least a portion of the sensors, actuators or both are supported by the inner surface of said flexible or stretchable substrate and at least a portion of the sensors, actuators or both are supported by the outer surface of the flexible or stretchable substrate. In an embodiment, an electronic device may be supported by both surfaces, such as a pressure sensor having aligned and paired electronic devices on both the internal and external surface that communicate with each other to provide an output that varies with separation distance between the electronic surfaces, such as by an applied pressure that changes thickness of a substrate that is elastomeric. In this manner, the devices may be electrodes that provide a measure of capacitance, a heat source and sensor that provide a measure of temperature, an optical source and optical detector that provides a measure of a light property, such as optical intensity. The common aspect of these systems is that the output of the device depends on substrate thickness between the devices, which in turns depends on the applied pressure or force. In this manner, the system provides a unique platform for pressure or force measurement with an external surface.

In an embodiment, the electronic device comprises a plurality of electro-tactile stimulators provided in an array and supported by said the surface of the substrate for electrically stimulating an appendage in the enclosure. In an aspect, the functional electronic device comprises a multiplexed array of said electrotactile stimulators. In an aspect, the electro-tactile stimulators of the array are electrically interconnected via a network of serpentine electrical interconnects.

In an aspect, any of the electro-tactile stimulators provided herein comprise a thin film metal structure having an inner region surrounded by an outer region, wherein a gap is provided between the inner region and the outer region. Such regions are optionally described in term of their dimensions. Examples include an inner region having lateral dimensions selected from the range of 10 µm to 1000 µm, an outer ring having lateral dimensions selected from the range of 10 µm to 5000 µm and a gap having lateral dimensions selected from the range of 10 µm to 1000 µm.

In an embodiment, the inner region is a conductive disk-shaped electrode and the outer region is a conductive ring-shaped electrode positioned concentric with said disk-shaped electrode.

In an embodiment, the electronic device comprises a plurality of tactile sensors provided in an array and supported by the outer surface, inner surface, or both the outer and inner surface of the substrate. In an aspect, the electronic device comprises a multiplexed array of tactile sensors. Paired electronic devices aligned but on opposite elastomeric substrate surfaces provide one means for measuring a pressure or force exerted by or against any of the systems provided herein.

In an embodiment, the tactile sensors of the array are electrically interconnected in independently connected via a network of serpentine electrical interconnects.

In an aspect each of the tactile sensors comprises a thin film metal structure having lateral dimensions selected from the range of 100 µm to 5000 µm. In one example, the thin film metal structure of the tactile sensors is a conductive disk-shaped electrode.

In another embodiment the electronic device comprises one or more tactile sensors supported by the outer surface and one or more electro-tactile stimulators supported by the inner surface, wherein one or more tactile sensors are in electrical communication with one or more electrotactile stimulators such that an output from the one or more tactile sensors is provided to the one or more electrotactile stimulators to electrically stimulate the appendage in proportion to the tactile sensor output. In one aspect, the inner surface and outer surface arrays are spatially aligned. "Spatially aligned" refers to an output from the sensor array that spatially varies, with the magnitude of sensor output that varies with position of the sensor, and the corresponding stimulation to the appendage that correspondingly spatially varies in accordance with the spatially varying output from the sensors.

In an aspect, electronic device comprises a plurality of electrodes, each electrode comprising an inner disk having a diameter that is less than 1 mm; and an outer ring that surround the inner disk, wherein the inner disk and outer ring are concentrically positioned relative to each other, with a separation distance between the inner disk and outer ring selected from a range that is greater than or equal to 100 μm and less than or equal to 500 μm.

As desired, any of the systems optionally further comprise one or more additional electronic components supported by the inner surface, the outer surface or both; the additional electronic components selected from the group consisting of a sensor, an actuator, a power source, a wireless power source, a photovoltaic device, a wireless transmitter, an antenna, a nanoelectromechanical system, a microelectromechanical system and arrays and any combinations thereof. In an aspect, the one or more additional electronic components comprise a strain gauge, such as a strain gauge comprising one or more semiconductor nanomembranes.

In an embodiment, each semiconductor nanomembrane independently has lateral dimensions selected from the range of 1 μm to 10 mm and a thickness selected from the range of 100 nm to 100 μm.

In an aspect, the strain gauge comprises a plurality of at least three electrically connected semiconductor nanomembranes.

In an aspect, the semiconductor nanomembranes are electrically interconnected via a network of serpentine electrical interconnects.

In an embodiment, any of the systems provided herein comprise one or more inorganic semiconductor components, such as each of the one or more inorganic semiconductor components independently comprising a polycrystalline semiconductor material, single crystalline semiconductor material or a doped polycrystalline or single crystalline semiconductor material.

In an aspect, each of the one or more inorganic semiconductor components independently comprises a single crystalline semiconductor material. In an aspect, each of the one or more inorganic semiconductor components independently has a thickness that is less than or equal to 100 μm. In an aspect, each of the inorganic semiconductor components of the electronic device have a thickness selected from the range of 50 nanometers to 100 μm. In an aspect, each of the inorganic semiconductor components of the electronic device has a net flexural rigidity less than or equal to $1\times10^{-4}$ Nm, a Young's modulus selected from the range of 0.5 MPa to 10 GPa, a net bending stiffness less than or equal to $1\times10^8$ GPa μm$^4$.

In an embodiment, each of the one or more inorganic semiconductor components independently comprises a semiconductor nanomembrane structure, such as a nanomembrane structure that is a diode electronic component.

In another aspect, any of the systems provided herein comprise one or more metallic components. In an aspect, the one or more metallic conductor components comprise a plurality of electrodes provided in an array.

In an embodiment, any of the metal electrodes provided herein, such as within an array, are described in terms of a thickness. In an aspect, the electrodes in an array independently have a thickness less than or equal to 100 μm, or selected from the range of 50 nanometers to 100 μm. In an embodiment, the number of electrodes in an electrode array is selected from a number that is between 10 to 10,000 electrodes.

In an aspect, the electrodes of the array are electrically interconnected via a network of serpentine electrical interconnects.

In an embodiment, any of the systems provided herein have the one or more sensors, actuators or both of the electronic device comprises a stretchable or flexible electrode array comprising a plurality of electrodes, multiplex circuitry and amplification circuitry. In an aspect, the stretchable or flexible electrode array comprises a plurality of electrode unit cells, such as 50 or more electrode unit cells. Optionally, adjacent electrode unit cells of the electrode array are further described in terms of a separation distance, such as adjacent unit cells separated from each other by a distance less than or equal to 50 μm, or a range between 500 nm and 50 μm. In an embodiment, the electrode unit cells of the electrode array are supported by an area of the flexible or stretchable substrate ranging from 10 mm$^2$ to 10,000 mm$^2$.

In an aspect, each electrode unit cell of the electrode array comprises a contact pad, amplifier and multiplexer, wherein the contact pad provides an electrical interface to the tissue and is in electrical communication with the amplifier and multiplexer. In an embodiment, the amplifier and multiplexer of the unit cell comprises a plurality of transistors.

Any of the one or more metallic conductor components herein comprise a plurality of stretchable electrical interconnects. Optionally, the stretchable electrical interconnects are at least partially free-standing or provided in a tethered geometry. Optionally, the stretchable electrical interconnects have a curved geometry. Optionally, the electrical interconnects have a serpentine configuration. Optionally, the stretchable electrical interconnects electrically connect rigid device islands comprising at least a portion of the one or more one or more inorganic semiconductor components, one or more metallic components, or one or more inorganic semiconductor components and one or more metallic components.

In an aspect, at least a portion of the rigid device islands each independently comprise a single crystalline inorganic semiconductor structure, or a single crystalline semiconductor nanomembrane.

In an aspect, the rigid device islands comprise the one or more sensors, actuators or both, such as sensors or actuators selected from the group consisting of: an electrode, a tactile sensor, a strain gauge, a capacitance sensor, a temperature sensor, a pressure sensor, a motion sensor, a position sensor, a displacement sensor, an acceleration sensor, a force sensor, a chemical sensor, a pH sensor, a capacitive sensor, an optical sensor, a photodetector, an imaging system, an electrotactile stimulator, an electrode, a heat source, a piezoelectric element, an acoustic element, a source of RF energy, a magnetic actuator, a source of electromagnetic radiation, a laser, a light emitting diode and arrays and any arrays and combinations thereof.

Any of the systems provided herein may have at least a portion of the flexible or stretchable electronic device supported by either the outer surface, by the inner surface of the flexible or stretchable substrate, or by both surfaces. In an aspect, the inner surface and outer surface are interchangeably flippable without substantial degradation of a functionality parameter of the one or more sensors, actuators or both supported by the inner surface or the outer surface of the flexible or stretchable substrate.

For example, a system comprising an array of actuators, sensors, or actuators and sensors, is interchangeably flippable between inner and outer and outer and inner configurations without substantial degradation of a functionality parameter of the array of actuators, sensors, or actuators and sensors. In an aspect, the flipping facilitates placement of electronic devices on an inner surface that is otherwise not accessible or amenable to conventional printing techniques. In an embodiment, the outer surface that supports the electronic device is flipped, so that after flipping the functional electronic device supported by the outer surface is the functional electronic device supported by the inner surface. In an embodiment, the functional electronic device is an array of electrotactile stimulators, and at least 90% of the electrotactile stimulators remain functional after flipping from an outer facing surface to an inner facing surface geometry.

In an aspect, the flexible or stretchable substrate has a closed tube geometry. In an embodiment, the closed tube geometry has one access opening or two access openings.

In an aspect, the enclosure has cross sectional dimensions selected from the range of 5 mm to 1000 cm. Depending on the application of interest, the cross sectional dimensions are appropriately selected. For example, finger-tip electronics may have a smaller cross sectional dimension than a torso or a head electronics system, which may be smaller than a remote sensing vehicle or instrument surface connected thereto.

In an embodiment, any of the flexible or stretchable substrates provided herein is an elastomeric substrate.

In an aspect, the flexible or stretchable substrate is a polymer, an inorganic polymer, an organic polymer, a plastic, an elastomer, a biopolymer, a thermoset, rubber, or any combination of these. In an aspect, the flexible or stretchable substrate is PDMS, parylene, polyimide, or silicone such as Ecoflex® (Smooth-On, Inc.) silicone. In an aspect, the flexible or stretchable substrate is a biocompatible material or a bioinert material.

In an embodiment, the flexible or stretchable substrate has an average thickness selected over the range of 0.25 µm to 10,000 µm, including any sub-combination thereof, such as between about 1 µm and 5 mm, or about 1 mm.

In an aspect, the flexible or stretchable substrate has a substantially uniform thickness supporting the electronic device or has a thickness supporting the electronic device that varies selectively along one or more lateral dimensions. In this context, "substantially uniform" refers to a substrate at rest having a thickness that varies less than about 10%, less than about 5% or less than about 1%. Alternatively, substantially uniform may refer to a substrate that has received an appendage in the enclosure, having a thickness that that varies less than about 10%, less than about 5% or less than about 1%. Optionally, substantially uniform refers to a statistical parameter, such as a standard deviation or standard error of the mean of an average thickness that is within about 10%, 5% or 1% of the average thickness over a selected portion of the substrate, or over the entire substrate surface area.

In an embodiment, the flexible or stretchable substrate is a flexible or stretchable mesh structure. In an embodiment, at least a portion of the electronic device has a mesh structure. Examples of mesh structures include open mesh geometries where a substantial portion of the relevant is open space or void, such as for longitudinally aligned interconnects which may be curvy but have a general alignment direction. Similarly, longitudinally arranged strips of substrate may be provided such as to provide additional breathability to an appendage to which the system is mounted. Alternatively, the substrate may have perforations or passages. This mesh aspect may be defined in terms of relative amount of open space compared to the perimeter-defined substrate footprint, such as between about 10% to 90%, and any subranges thereof, such as between 20% to 80%, 30% to 70%, depending on the application of interest.

In an aspect, the flexible or stretchable substrate has an average Young's modulus selected over the range of 0.5 KPa to 10 GPa and/or a fracture strain greater than or equal to 500%, such as between about 500% and 900%.

Any of the systems provided herein may further comprise a barrier layer at least partially encapsulating at least a portion of the functional device. For example, the barrier layer may limit a net leakage current from the electronic device to an amount which does not adversely affect a material in contact with the system or limits a heat transfer from the electronic device to an amount which does not adversely affect a material in contact with the system. This can be particularly beneficial in the context of biological systems that may be adversely affected by electrical or thermal leakage, such as an biological tissue covering an appendage within the enclosure.

The barrier layer may also substantially prevent passage of an external fluid to at least a portion of the electronic device. This may be beneficial to maintain electronic device functionality, robustness, and long-term wear characteristics.

In an embodiment, the barrier layer is a polymer, an inorganic polymer, an organic polymer, a plastic, an elastomer, a biopolymer, a thermoset, rubber or any combination of these. In an embodiment, the barrier layer is PDMS, parylene, polyimide, or Ecoflex®. In an embodiment, the barrier layer comprises a composition that corresponds to the flexible or stretchable substrate.

In an aspect, the barrier layer has an average thickness selected from the range of 1 µm to 100 µm, an average modulus selected over the range of 0.5 KPa to 10 GPa. Optionally, the barrier layer is described by a ratio of the average thickness of the barrier layer to the average thickness of the flexible or stretchable substrate, such as a ratio that is selected over the range of 0.01 to 1. Depending on the specific application, the barrier layer is positioned as desired. Examples of positions include between otherwise adjacent device layers and/or between a device layer and the surrounding environment such as the appendage, air, or an external surface. In an aspect, the barrier layer has a mesh structure.

In an embodiment, the system further comprises one or more stretchable interconnects that electrically connect at least a portion of said one or more sensors, actuators or both. Such stretchable interconnects may be configured to impart stretchability and/or flexibility to the system. Any of the one or more stretchable interconnects comprises an electrically conductive metal provided in a bent configuration.

Bent configuration is used broadly and may include a nanowire in a serpentine configuration. The nanowire may have a rectangular cross-section, with a thickness selected from the range of 50 nm to 1 µm and a width that is selected from the range of 10 µm to 1 mm. The serpentine configuration may be meandering undergoing a plurality of directional changes relative to an average longitudinal direction defined by a straight line between the interconnect ends. In an aspect, the serpentine configuration is characterized by an average radius of curvature selected from the range of 100 µm to 10 mm.

In an aspect, the system comprises a plurality of interconnects arranged in at least two interconnect layers, with adjacent interconnect layers separated by a barrier layer that is an electrically insulative elastomeric layer. This configuration facilitates compact overlying interconnect wiring. In an aspect, the electronic devices comprise rigid device islands electrically connected to at least one interconnect, wherein the interconnect bent configuration accommodates stresses from bending and stretching of the thin elastomeric substrate. In an aspect, the bending and stretching stresses are from flipping the inner and outer surfaces of the flexible or stretchable substrate.

In an aspect, the system has a neutral mechanical plane (NMP), that is positioned at a depth that corresponds to a depth of a strain-sensitive component. For example, the NMP may run along a surface defined by or within the strain-sensitive components, such as a strain sensitive component that is a semiconductor or metal material. Optionally, NMP positioning is by providing substrate or barrier layers, including by varying the thickness of those layers.

In an aspect, at least a portion of the one or more inorganic semiconductor components, one or more metallic components or both are printable structures. In an embodiment, at least a portion of the one or more sensors, actuators or both are assembled on the flexible or stretchable substrate via transfer printing. In an embodiment, at least a portion of the one or more sensors, actuators or both are assembled on said flexible or stretchable substrate via microtransfer printing, dry contact transfer printing, solution-based printing, soft lithography printing, replica molding, or imprint lithography.

In an embodiment, the enclosure has an interior volume and at least one opening for receiving and covering an appendage. In an aspect, the enclosure interior volume that is greater than or equal to 1 cm$^3$ and less than or equal to 10,000 cm$^3$.

In an aspect, the enclosure has a shape, such as a substantially cylindrical or hemispherical shape. In an aspect the enclosure is shaped to receive a hand, a finger, a finger-tip or any portion thereof.

In an embodiment, the enclosure has one or two access openings for receiving the appendage, such as one opening to receive an appendage that is a finger or a head portion, or two openings to receive an arm, leg, or torso, wherein a portion of the appendage extends through the enclosure first and second access openings.

In an aspect, the flexible or stretchable substrate wraps around the appendage under a longitudinally-directed tension or is rolled over the appendage under a circumferentially-directed tension.

In an embodiment, the appendage is part of a living animal, such as a finger, an arm, a leg, a head, a torso, or any portion thereof.

In an aspect, any of the systems provided herein relate to first and second electronic devices supported by opposing surfaces, such as inner and outer surfaces, wherein the devices are in communication with each other. Depending on the type of device, the communication is characterized by a parameter, such as an electrical parameter (capacitance) or thermal (temperature), that varies with substrate thickness between the devices. Preferably, the substrate is elastomeric. In this manner, a pressure sensor is provided, wherein the communication parameter depends on substrate thickness, which in turn depends on the applied force or pressure exerted on the substrate.

In an aspect, the enclosure has a receiving dimension that is smaller than a corresponding dimension of the appendage, wherein during use a strain in the flexible or stretchable substrate increases the receiving dimension to accommodate the appendage within enclosure without adversely impacting the flexible or stretchable electronic device. In an embodiment, the strain generates a contact force between the elastomeric substrate and the appendage within the enclosure to establish and maintain intimate and conformal contact between the flexible or stretchable electronic device supported by the substrate inner surface and a surface of the appendage. In an aspect, the strain is selected from a range that is greater than or equal to 1% and less than or equal to 100%.

In an embodiment, the array of sensors, actuators or both, are described in terms of a spatial density, such as a spatial density selected from a range that is between about 1 mm$^{-2}$ and 1 cm$^{-2}$.

In an aspect, any of the systems are multifunctional, wherein the inner surface supports a first array of actuators or sensors, and the outer surface supports a second array of sensors or actuators. In an embodiment, the first array comprises electrotactile stimulators to interface with skin of a living animal in conformal contact with the electronic devices of the first array, and the second array comprises tactile sensors to measure a physical parameter from tactile interaction with an external surface. In an aspect, the tactile sensor comprises opposing electrodes on the inner and the outer surfaces to measure a capacitance between the electrodes, wherein the capacitance varies with substrate thickness between the opposing electrodes.

In an aspect, the inner surface supports a first electronic device and the outer surface supports a second electronic device, wherein the electronic devices are in an opposed configuration and in communication with each other, wherein they form, for example, a pressure sensor. In an aspect, the communication is electrical communication (capacitance) wherein an electrical property varies with substrate thickness between the first and second opposed electronic devices. In an aspect, the devices are in thermal communication, wherein a thermal property changes with substrate thickness between the opposed electronic devices. In an aspect the devices are in mechanical communication (pressure or force).

In an embodiment, the first and second electronic devices are in thermal communication with each other. For example, one electronic device may be a heater and a second electronic device may be a thermal sensor, with the heater placed on an inner or outer surface and the thermal sensor on the opposite surface, wherein the heater can maintain a constant temperature on its support surface. In this manner, the thermal communication between the heater and sensor is used to assess a pressure or force exerted against a substrate whose thickness varies depending on the magnitude of the pressure or force applied against the substrate. Generally, with higher applied pressures, substrate thickness decreases thereby increasing thermal conductivity from the heater to the sensor which is detected by an increase in the temperature detected by the thermal sensor. In an aspect, the heater is a resistive heater whose temperature increases with increasing current, such as by electrically conductive wires connected to a heating pad. In an aspect where the appendage is living tissue, preferably the heater is placed on the outer surface to avoid unwanted heating of the living tissue. Accordingly, the thermal sensor may be aligned with the heater on an inner surface. In an aspect, the system may be calibrated by the use of an unpaired thermal sensor to adjust for fluctuations in ambient temperature. Alternatively the communication may be optically, between an optical source and optical detector, wherein optical transmission varies as a function of substrate thickness between source and detector.

In an aspect, a sensor is provided on the inner surface of any of the systems described herein. The sensor or sensors may be one or more of a thermal sensor to measure body temperature including as a measure of body core temperature, a hydration sensor to measure hydration levels including as a measure of whole body hydration, or another sensor to detect a biological parameter of interest (e.g., pH, oxygenation level, etc.). Such measures are useful in providing warning about potential risk of an adverse event, such as heat-stroke or dehydration.

In an embodiment, the first and second electronic devices are in electrical communication with each other, wherein change in substrate thickness changes electrical capacitance or electrical resistance between the electronic devices. In this manner, pressure or force is determined by measuring capacitance between a pair of aligned electrodes on the inner and outer surfaces. In an aspect, the second array of sensors generates an electrical output that is input to the first array of actuators, wherein the first array of actuators interface with the appendage surface that is skin of a user to provide information to the user about the external surface. In this context, "information" refers to a property that is detected by the sensor, and so accordingly, can be a physical property such as contact force or pressure generated by surface contact or a property inherent to an external surface, such as temperature, pH, hydration, or presence of a chemical or biological material.

An example of an appendage mountable electronic system includes: (i) an elastomeric substrate having an inner surface and an outer surface, wherein the inner surface defines an enclosure capable of receiving an appendage having a curved surface; (ii) a first electronic device supported by the inner surface; (iii) a second electronic supported by the outer substrate, wherein the first and second electronic devices are in an opposed configuration with respect to each other and separated by a thickness of the elastomeric substrate to form a functional pressure sensor whose output varies as a function of elastomeric substrate thickness; wherein each of the first and second electronic devices may comprise a thin electrically conductive material having a thickness less than 1 mm and a lateral dimension less than 5 mm and the elastomeric substrate has a resting thickness that is less than 10 mm to for an output that is capacitance when an electrode is energized.

In another embodiment, the appendage mountable electronic system comprises: an elastomeric substrate having an inner surface and an outer surface, wherein the inner surface defines an enclosure capable of receiving an appendage having a curved surface, and the elastomeric substrate has a resting thickness that is less than 10 mm; a first electronic device supported by the inner surface; a second electronic device supported by the outer substrate, wherein the first and second electronic devices are in an opposed configuration with respect to each other and separated by a thickness of the elastomeric substrate to form a pressure sensor whose output varies as a function of elastomeric substrate thickness; each of the first and second electronic devices comprises one or more inorganic semiconductor components, one or more metallic components, or one or more inorganic semiconductor components and one or more metallic components, having a thickness less than 1 mm and a lateral dimension less than 5 mm.

In an aspect, the system further comprises a first plurality of electrical interconnects to electrically connect each member of the array of first electrodes and a second plurality of electrical interconnects to electrically connect each member of the second array of electrodes, wherein the electrical interconnects are in a serpentine configuration. The electrical interconnects may be independently encapsulated by an encapsulation layer. A barrier layer may electrically isolate the first plurality of electrical interconnects from the second plurality of electrical interconnects. An applied pressure to the elastomeric substrate decreases substrate thickness between the pair of electrodes, thereby increasing the capacitance. Another example is first and second electronic devices that are in thermal communication with each other, wherein one of the electronic devices is a thermal source and the electronic device is a thermal detector that measures a temperature, and a change in elastomeric substrate thickness between the thermal source and the thermal detector changes the temperature measured by the thermal detector.

The systems discussed herein are also referred to as an "appendage mountable electronic system" or "appendage conforming system", and may comprise a thin flexible and/or stretchable substrate having an inner surface and an outer surface. The substrate inner surface defines an enclosure for receiving a curved surface (e.g., an appendage surface), such as by covering and conformally contacting the surface associated with an appendage in the enclosure. Optionally, the substrate is described in terms of a thickness, such as a thickness that is less than 10 mm, a thickness that is less than 1 mm, a thickness that is less than 500 µm, or a thickness selected over a range that is greater than or equal to 100 µm and less than or equal to 1 mm. Thickness may be selected based on the operating conditions and relevant application. For example, in applications having substantial surface abrasion, the substrate may be correspondingly thicker and/or have higher durability characteristics. A functional electronic device is supported by the elastic substrate inner surface or the elastic substrate outer surface. The functional electronic device comprises a device component that is one or more inorganic semiconductor components, one or more metallic components, or one or more inorganic semiconductor components and one or more metallic components. The functional electronic device, including any device components thereof, is stretchable and bendable. The functional electronic device, including any device components thereof, have a thickness, such as a thickness that is less than or equal to 10 µm. The thin lay-out geometry of the devices and the properties of the elastomeric substrate provide a number of functional benefits in terms of the interaction between object surfaces and the electronic device, and also to facilitate certain unique transfer printing processes for making any of the devices herein.

For example, the inner surface of the substrate may be visually and/or physically inaccessible in that the three-dimensional shape of the enclosure is a closed surface that defines an interior volume. Such an enclosure, particularly if small, is difficult to access, making it difficult to place functional electronic devices on the enclosure surface. Although such an enclosure may have one or two openings, it still may not be readily accessible for transfer printing of functional electronic devices, in comparison to an open enclosure having a free end that may be used to open the enclosure to transfer printing. The elastomeric substrate properties of the instant invention allow for the specially configured functional electronic devices on an outer surface to be flipped so that functional electronic devices are on the inner surface defining the enclosure. This is achieved by the special configured thin device component layouts and correspondingly thin functional electronic device, that can be substantially stretched, bent, and/or folded without adversely impacting device functionality. Accordingly, an aspect of the instant invention relates to an inner surface that is not physically accessible to conventional electronic device transfer printing processes. The outer surface of any of the substrates discussed herein, in contrast, faces away from the interior and is visually and physically accessible with no or minimal applied force. For example, the outer surface may have invaginations that become physically accessible by a relatively straight-forward minimal force application to stretch the substrate and remove invaginations or folds over a desired region. Transfer printing functional electronic device arrays to the outer surface, followed by substrate surface flipping, facilitates placement of functional electronic device and arrays in extremely confined interior volumes and enclosures not otherwise accessible to conventional transfer printing techniques.

In an embodiment, any of the substrates in any of the devices and methods provided herein, has an inner and outer surface that are interchangeably flippable without substantial degradation of a functionality parameter of the functional electronic device supported by the inner surface or the outer surface. In this embodiment, it does not matter which surface supports the functional electronic device, as the substrate surfaces can be readily flipped so that an outward facing electronic device can be flipped inward by flipping the substrate surfaces. Similarly an inward facing electronic device can be flipped outward by flipping the substrate surfaces. Accordingly, in an aspect, the elastomeric substrate material and the attached functional electronic devices, are selected so as to have appropriate physical characteristics to allow flipping without adversely impacting the substrate integrity or device functionality. For example, the material may have a relatively low modulus, such as less than 1 MPa, less than 500 kPa, less than 100 kPa, or selected from a range that is greater than or equal to 10 kPa and less than or equal to 200 kPa. Similarly, the substrate may have a relatively high fracture strain, such as a fracture strain that is greater than or equal to about 200%, 500%, 800%, or that is selected from a range that is greater than or equal to 400% and less than or equal to 1,200%. In an aspect, including for interfacing with a user's skin, the substrate may be a silicone material, such as Ecoflex® silicone (Shore 00-30 hardness (Smooth-On, Inc.)).

In one aspect, any of the electronic devices provided herein comprise an array of functional electronic devices. In one embodiment, the functional electronic devices are sensors, actuators, or both sensors and actuators. For example, a sensor may provide information about a physical parameter related to the electronic device, such as sensor motion, velocity, acceleration, or about a physical parameter associated with a surface in which the electronic device physically contacts, e.g., pressure, force, temperature, electric potential, conductivity, hydration, moisture, electromagnetic radiation, or for any parameter that a sensor is capable of measuring. An actuator, in contrast, functions to provide a signal or stimulus to a surface. Optionally, the plurality of actuators may be controlled by a plurality of sensors, such as actuators on an inner surface and sensors on either the outer surface or the outer surface of another substrate. In this manner, virtual reality systems are provided, such as a user that "feels" what another surface "feels" like without actually touching the surface, such as by a remote controlled instrument or robotic device having a surface covered with any of the devices provided herein. Alternatively, a multi-functional device, such as a glove, may have sensors on the outer surface to sense a parameter which is then transmitted to a stimulator on the inner surface in conformal contact with the user skin. In this manner, information about a condition outside the glove is detected by a user via the stimulator on the inner surface.

One manner in which the ability to flip and/or stretch substrate surfaces to accommodate shaped surfaces, even highly irregular shapes, without sacrificing device functionality is by specially constructing and packaging the electronic layout and geometry so that rigid materials most susceptible to fracture are insulated from high stresses. For example, flexible and stretchable interconnects may be incorporated into the functional electronic devices and positioned so as to accommodate bending and flexing stresses, thereby insulating rigid or brittle materials from unduly high stresses. The interconnects electrically connect a functional electronic device, including multiple functional electronic devices, that may be configured as rigid device islands. In an embodiment, the flexible and stretchable electrical interconnect comprises an electrically conductive metal in a bent configuration. Examples of bent configurations include wavy geometry (see, e.g., U.S. Pat. No. 7,622,367 (38-04A)), buckle geometry (see, e.g., U.S. Pat. No. 8,217,381 (134-06)), and/or serpentine configurations (see, e.g., U.S. Pat. Pub. 2010/0002402 (213-07); PCT Pub. WO2011/084450 (126-09WO); U.S. Pat. Pub. 2013/0041235 (29-11)).

Optionally, an interconnect comprises a nanowire in a serpentine configuration. High flexibility and bendability is achieved particularly by providing interconnect cross-sectional dimensions that are small relative to the more rigid components that the interconnects connect. For example, the nanowire can have a rectangular cross-section, with a thickness selected from a range that is greater than or equal to 50 nm and less than or equal to 1 μm, and a width that is selected from a range that is greater than or equal to 1 μm and less than or equal to 1 mm. In an aspect, the serpentine configuration is characterized by an average radius of curvature, such as selected from a range that is greater than or equal to 100 μm and less than or equal to 10 mm.

In an aspect, the electronic device comprises a plurality of interconnects arranged in at least two interconnect layers, with adjacent interconnect layers separated by a barrier layer that is an electrically insulative elastomeric layer, thereby providing compact wiring with overlying interconnects.

The electrical interconnects are particularly advantageous in embodiments wherein the functional electronic devices are relatively rigid, such as being made from relatively brittle components, including semiconductor components such as thin layers. In an aspect, the functional electronic devices comprise rigid device islands that are electrically connected to at least one interconnect. In this aspect, the interconnect bent configuration accommodates stresses from bending and stretching of the thin elastomeric substrate, thereby isolating the rigid device islands from applied stresses. In an aspect, the bending and stretching stresses are from flipping the inner and outer surfaces of the thin elastomeric substrate.

Any of the electronic devices provided herein may comprise an array of functional electronic devices characterized by a total number of functional electronic devices, such as a number selected from a range that is greater than or equal to 2 and less than or equal to 1000. In an aspect, the number is from between about 4 and 100. In an aspect, the number is from between about 4 and 20. In an aspect, any of the arrays described herein are further defined in terms of a footprint area, wherein the footprint area is the surface area covered by the array, and can be defined as the outermost portion of individual devices within the array. Accordingly, based on the number of functional electronic devices and the footprint area, a spatial density is determined. For applications requiring fine spatial resolution, there may be as many as about 1 to 10 devices per mm$^2$. For other applications where fine spatial resolution is not necessary, the devices may be more sparsely distributed, such as 1 to 10 devices per cm$^2$.

In an aspect, the functional electronic device comprises a multiplexed array of electrotactile stimulators for interfacing with a curved surface, wherein the curved surface corresponds to living tissue.

In an embodiment, any of the electronic devices provided herein are part of a human-machine interface, such as an instrumented glove or a medical glove for surgery. The electronic devices are readily used in other applications, including an array of force or pressure sensors for measuring force or pressure exerted against a surface. Such an application can provide a highly accurate understanding of, for example, forces exerted against a surface and correspondingly provide warnings or alarms if threshold values are exceeded. This can occur, for example, on any biological surface.

In an aspect, the inorganic semiconductor components and/or the metallic conductor components independently comprise one or more thin film structures having a thickness that is less than or equal to 1 μm.

In an embodiment, the electronic device comprises one or more inorganic semiconductor components, such as inorganic semiconductor components independently comprising a nanomembrane structure, a polycrystalline semiconductor material, single crystalline semiconductor material or a doped polycrystalline or single crystalline semiconductor material.

In an aspect, the device has a neutral mechanical plane (NMP), wherein the NMP is positioned at a depth that corresponds to the inorganic semiconductor position within the device, such as an inorganic semiconductor that is a nanomembrane. Such NMP positioning further assists in device tolerance to bending and stretching stresses, such as occurs during flipping of the substrate inner and outer surfaces.

In an aspect, the device comprises one or more metallic conductor components, such as a metallic conductor component that is an electrical interconnect having a curved geometry. The curved geometry may be at least partially free-standing. The curved geometry may comprise a serpentine configuration, with the bending either in plane, out of plane, or a combination thereof. In an embodiment, electrical interconnects electrically connect rigid device islands. In an aspect, rigid device islands comprise an inorganic semiconductor, such as a silicon nanomembrane.

In an aspect, the rigid device islands correspond to positions of sensors or actuator components that tend to be strain-sensitive due to various parts that are relatively brittle and susceptible to physical fracture. In an aspect, the sensors or actuators are electrotactile devices, motion sensors, pressure sensors, pressure actuators, thermal sensors, thermal sources, or a combination thereof the configuration may be described as a mesh geometry, in that the curved interconnects are configured to accommodate stresses not otherwise well-tolerated by a rigid device island.

As described, the functional electronic device can be supported by the substrate outer surface or by the substrate inner surface, particularly in view of the embodiment where the substrate is flippable. In an aspect, the outer surface that supports the functional electronic device is flipped, so that after flipping the functional electronic device supported by the outer surface is the functional electronic device supported by the inner surface. In an aspect, after flipping at least 90% of the functional electronic devices on the inner surface remain functional after flipping from an outer surface facing to an inner facing surface geometry. In this manner, the enclosure defined by the inner surface actually corresponds to a substrate surface that was originally an outer surface.

In an embodiment, for example, at least a portion of the one or more inorganic semiconductor components, one or more metallic components or both are printable structures. In an embodiment, for example, at least a portion of the one or more sensors, actuators or both are assembled on said flexible or stretchable substrate via transfer printing. In an embodiment, for example, at least a portion of said one or more sensors, actuators or both are assembled on said flexible or stretchable substrate via microtransfer printing, dry contact transfer printing, solution-based printing, soft lithography printing, replica molding, or imprint lithography.

In an embodiment, the thin elastomeric substrate inner surface defines an enclosure or an interior volume having at least one opening for receiving and covering a curved surface. In an aspect, the surface to be covered and contained within the enclosure is an object that is part of a living animal, such as an appendage, a finger, an arm portion, a leg portion, a head portion or a torso portion.

In an embodiment, the thin elastomeric substrate inner surface that defines the enclosure for receiving a curved surface and the substrate has physical properties to receive, accommodate and conformally contact under a self-generated contact force, the curved surface. In an aspect, the physical properties correspond to a substrate Young's modulus that is less than or equal to 500 kPa, and a substrate fracture strain that is greater than or equal to 500%. Functionally, this ensures the substrate can conformally contact even highly irregularly shaped surfaces and also can undergo surface flipping without adverse impact to structural integrity.

In an aspect the enclosure has a receiving dimension that is smaller than a corresponding dimension of the curved surface, wherein during use a strain in the thin elastomeric substrate increases the receiving dimension to accommodate the received surface within the enclosure without adversely impacting the functional electronic device. For example, if the substrate is for receiving a finger, the enclosure may have a diameter that is less than the diameter of the finger. Accordingly, during use the finger stretches the elastomeric substrate, thereby generating a radially-directed contact force between the finger surface and the substrate. In this manner, the strain generates an intimate contact force between the thin elastomeric substrate and the curved surface within the enclosure to establish and maintain intimate and conformal contact between the device component on the substrate inner surface and the curved surface.

The amount of strain in the substrate may be varied so as to control the amount of contact force between the substrate, and therefore any functional devices on the inner substrate surface, and the surface within the enclosure. For applications where greater contact force is required, a characteristic dimension of the enclosure is corresponding decreased relative to the size of the object being accommodated. For example, the enclosure volume reduced by decreasing a diameter of the enclosure. In an aspect, the electronic device during use has a strain that is selected from a range that is greater than or equal to 1% and less than or equal to 100%.

Of course, due to the large fracture strain of the elastomeric substrate as well as the highly flexible and elastic electronic devices, such as by the use of flexible and stretchable interconnects and thin layout geometry, the invention can accommodate even higher strains and stresses as desired.

The electronic device may be further described in terms of the enclosure (also referred herein as, and used interchangeably with, interior portion or interior volume), including interior portion length, width, depth and/or volume. For example, the enclosure may be cylindrically shaped with an average diameter of 5 mm to 30 cm, and/or an average length of 5 mm to 30 cm. In an aspect, the enclosure has a volume that is greater than or equal to 1 cm$^3$ and less than or equal to 10,000 cm$^3$.

In an aspect, the electronic device is an array of electronic devices with an electronic device spatial density selected from a range that is between about 1 mm$^{-2}$ (high density coverage) and 1 cm$^{-2}$ (low density coverage).

In an embodiment, the enclosure has a substantially cylindrical or partially spherical or hemispherical shape. The cylindrical shape is optionally covered at one end, such as to cover a finger-tip. Accordingly, any of the electronic devices may have an interior portion shaped to receive a finger or a finger-tip. The cylindrical shape may also be a tube that is open at both ends.

In an aspect, the enclosure is a partially-closed volume, so that the curved surface is covered such as by forcing the curved surface into the interior portion. In contrast, an open volume refers to an enclosure having at least one end free to move in that is not contiguously connected with another portion of the substrate. In this manner, an open volume may correspond to wrapping the inner surface around a curved surface and securing a loose end of the substrate to form the interior portion. This can be achieved by wrapping the thin elastomeric substrate around the curved surface under a longitudinally-directed tension ensures surface cover and conformal contact, under a substrate self-generated force. Alternatively, the thin elastomeric substrate can be rolled over the biological surface under a circumferentially-directed tension, such as by forcing an opening of the partially-closed volume to open further to receive the biological surface.

In an embodiment, any of the electronic devices described herein may be multifunctional. Multifunctional refers to there being at least two different types of functional electronic devices that provide different functions, such as an electrotactile stimulator and a sensor device. In an aspect, the inner surface supports a first array of functional electronic devices, and the outer surface supports a second array of functional electronic devices, with the first array having a different functionality than the second array. For example, the first array may comprise electrotactile stimulators for interfacing with skin of a living animal in conformal contact with the electronic devices of the first array, and the second array may comprise sensors for measuring a physical parameter from tactile interaction between the electronic devices of the second array and an external surface. Examples of sensors include strain gauge sensors and tactile sensors, such as piezoresistive, piezoelectric, capacitive and elastoresistive sensors.

In an aspect, the first array of electrotactile stimulators interface with skin of a living animal in accordance with a physical parameter measured by the second array of sensors, such as sensors and stimulators on the outside and inside of a substrate covering a finger.

In an embodiment, the array of functional electronic devices have a footprint surface area defined by the outer-most members of the array. The methods of making the devices are compatible with a wide range of footprint surface areas, depending on the application of interest. In one example, the footprint surface area is selected from a range that is greater than or equal 0.5 cm$^2$ and less than or equal to 100 cm$^2$.

In an embodiment, the array of functional electronic devices comprise a multiplexed array of electrotactile stimulators for interfacing with living tissue. In an aspect, the array of functional electronic devices comprises an array of electrodes, such as electrodes for sensing an electrical parameter and/or for application of an electrical parameter, such as electric potential. In an embodiment, each electrode comprises an inner disk having a diameter that is less than 1 mm and an outer ring that surrounds the inner disk, wherein the inner disk and outer ring are concentrically positioned relative to each other, with a separation distance between the inner disk and outer ring selected from a range that is greater than or equal to 100 μm and less than or equal to 500 μm. In an aspect, the thickness of the electrodes is less than 1 μm, such as on the order of hundreds on nanometers (e.g., 100 nm to 900 nm). In an aspect, any of the semiconductor components comprise a silicon nanomembrane that is part of an electronic device that is a diode, such as diode having a thickness that is less than 1 μm, or on the order of hundreds of nanometers (e.g., 100 nm to 900 nm). The diodes and electrodes may comprise part of a multiplexed circuit to facilitate device control and output processing, especially for arrays comprising a large number of functional electronic devices.

In another embodiment, the invention is a method for making any of the devices described herein. In an aspect, provided is a method of making an electronic device to cover and interface with a curved surface by providing an elastomeric substrate having an inner facing surface and an outer facing surface. A functional electronic device, such as an array of functional electronic devices, is transfer printed to the elastomeric substrate outer facing surface. The elastomeric substrate is flipped, so that after flipping the outer facing surface is the inner facing surface and the inner facing surface is the outer facing surface, thereby providing the array of device components on the inner facing surface, wherein after flipping the array of functional electronic devices remain functional. Remain functional refers to at least 90%, at least 95%, or all functional electronic devices remaining functional after flipping. The desired functionality level is achieved by incorporating any one or more of the device geometries provided herein, including by using ultrathin devices and device components (e.g., less than 1 μm), flexible and stretchable interconnects, including serpentine geometries, and neutral mechanical plan (NMP) layouts. Accordingly, any one or more of these device layouts and geometries may be incorporated in any one or more of the methods disclosed herein to achieve robust devices even after stresses associated with surface flipping.

In an aspect, the inner facing surface defines an interior volume or portion for receiving, covering and interfacing with the curved surface. In an aspect, the enclosure of the elastomeric substrate is obtained by casting an elastomeric precursor against a curved surface or a mold thereof and curing the elastomeric precursor to obtain the elastomeric substrate having an inner facing surface and an outer facing surface. In this fashion, the substrate may be tailored to specific curved surfaces that will be used in the system. In particular, an elastomeric substrate having a surface curvature at rest that corresponds to the curved surface may be generated. Optionally, the resultant cured substrate has a slightly smaller interior volume dimension than the corresponding dimension of the object that has the to-be-received curved surface. For example, the mold of the surface may be correspondingly slightly reduced in size. This is one means for ensuring there is a self-generated contact force generated by strain of the elastomeric substrate to accommodate the to-be-received curved surface. In an aspect, the mold size is selected so as to generate a strain in the elastomeric substrate that is selected from a range that is greater than or equal to 1% and less than or equal to 100%, or between about 1% and 20%. Alternatively, the substrate curvature at rest may be made by another process known in the art, such as extrusion.

In an aspect, the transfer printing comprises transferring the array functional electronic devices from a transfer stamp to an outer surface of the elastic substrate, such as by transfer printing (see, e.g., U.S. Pat. Nos. 7,943,491; 7,799,699; 7,932,123; 8,217,381; 8,198,621, 7,622,367, all of which are specifically incorporated by reference). In an embodiment, particularly for elastomeric substrates having a curved surface, the transfer printing further comprises flattening the elastomeric substrate into a flat geometry and transferring the array of functional electronic device to the elastic substrate in the flat geometry. After transfer, the elastomeric substrate may be released to relax back into its curved surface geometry. In another aspect, the transfer printing comprises rolling the transfer stamp over the outer surface of said elastic substrate in a curved geometry.

In an aspect, the curved surface to-be-received in the interior volume or portion has a surface shape that corresponds to a finger or a finger-tip surface shape.

In an aspect, the electronic device is incorporated into a finger or fingertip of a glove. In an aspect, the functional electronic device comprises an array of sensors, actuators, or sensors and actuators.

In an embodiment, the functional electronic device comprises an array of electrotactile electrodes in a mesh configuration, wherein electrical interconnects are electrically connected to the electrotactile electrodes.

In an aspect, the invention is a method of using any of the devices herein, such as a method of interfacing with a surface of an object. In an embodiment, the method comprises providing a thin elastomeric substrate having an inner facing surface defining an enclosure, and an outer facing surface. A functional electronic device is supported on the inner facing surface or the outer facing surface. The functional electronic device comprises a device component that is one or more inorganic semiconductor components, one or more metallic components, or one or more inorganic semiconductor components and one or more metallic components. The functional electronic device is stretchable and bendable with a thickness that is less than or equal to 10 µm. The surface that supports the functional electronic device is physically contacted with an object surface to interface the functional electronic device with the object surface of an object. In an aspect, the enclosure receives an object and attendant surface so as to provide physical support to the substrate. In an aspect, the method relates to expanding the volume of the enclosure so as to accommodate the object and curved surface being received within the enclosure.

For devices on the inner substrate surface, the method further comprises introducing the surface of an object to the enclosure for interfacing. For example, the object may be part of a living animal and the object surface corresponds to skin or epidermal layer. The functional electronic device may comprise an array of sensors, actuators, or both sensors and actuators. In an embodiment, the device comprises an array of electrotactile stimulators, such as for stimulating nerves in the skin or epidermal layer underlying the electrotactile stimulators.

Alternatively, for functional electronic devices supported by an outer facing surface, the physically contacting step may comprise introducing the surface of an object that is external to the substrate enclosure to the outer facing surface. In this aspect, the functional electronic devices on the outer surface interface with the externally located object surface, including sensors that measure a tactile sensation. In an aspect, the method further comprises the step of inserting a supporting object into the interior portion to physically support the elastomeric substrate. For example, in remote sensing the supporting object may be part of a remotely controlled object or a robotically controlled device. In this aspect, the functional electronic device may comprise an array of sensors for measuring a physical parameter of the object surface, ranging from a tactile-generated force parameter, to an inherent surface-related parameter such as temperature, conductivity, hardness, resilience or another parameter depending on the application of interest.

In another embodiment, a first functional electronic device is supported by the inner facing surface and a second functional electronic device is supported by the outer facing surface, and the physically contacting step comprises introducing a surface of a first object to the interior portion and a surface of a second object to the outer surface. For example, the first object may correspond to an appendage of a living person, and the first functional electronic device is part of an array of electrotactile stimulators that interfaces with a tissue overlying the appendage. The appendage may be a finger or fingertip where an electrotactile stimulation is provided that depends on the interaction of the of the second functional electronic device supported on the outer surface with the second object surface. In the case of a surgical glove, the second object surface may be part of a patient, such as biological tissue.

Any of the devices and processes provided herein may relate to an enclosure that receives a portion of the human body, including a finger, a fingertip or any other parts disclosed herein.

Provided herein are electronic devices configured to conform to a biological surface of user, including an epidermal layer or a skin layer. In an embodiment, the biological surface corresponds to an appendage. In an embodiment, the biological surface is a finger or multiple fingers, including the finger-tip. In an embodiment, the biological surface is a part of the human body, including the epidermis or skin. The device is particularly useful for mounting to a shaped portion of a user surface, including a user surface that moves and/or deforms. One aspect of the invention is that the electronic device is provided on a flexible, deformable and/or bendable substrate that, when appropriately mounted on the user, provides a self-generated force to ensure the electronic device is in good contact with the user surface, with the contact well-maintained and durable even over long periods of time, ranging from many minutes to many hours or days, as desired depending on the application of interest.

In an embodiment, the electronic device has a substrate with a three-dimensional curvature matched to a biological surface curvature. "Three-dimensional curvature" refers to a surface that is defined by (x, y, z) co-ordinates, or transformations thereof. The curvature is considered "matched" to a biological surface when there is substantial correspondence between the substrate surface and biological surface, particularly for that portion of the substrate receiving surface that supports the array of components. In this embodiment, the receiving surface of the substrate, and the array of components, is capable of physical contact, including conformal contact, with the biological surface. The substrate receiving surface, when oriented in an inner-facing direction, defines an enclosure having an inner volume that is configured to receive the biological surface, such as a finger, appendage, or other accessible portion of the user.

A functional benefit of the device configuration that provides an enclosure and inner volume for receiving a user body part is that the device substrate can provide a self-generated force to ensure intimate contact between the biological surface and the components of the array. In an aspect, the self-generated force is sufficient that no adhesive components or external force generation is required, and absence of those components does not impact the ability to reliably generate and maintain conformal contact.

The self-generated force from the device substrate may be a physical force applied in a normal direction with respect to an individual component within the array of components. Although force is applied in multiple directions, with a direction and magnitude that may vary over the biological surface, for an individual component a normal force on that component can be calculated from this force distribution. This normal force can be generated by various embodiments. In one embodiment, the electronic device is wrapped over a biological surface under tension, thereby providing the desired force. Alternatively, the electronic device can be rolled over a surface, with an effective circumferentially-directed tension providing the normal force to ensure conformal contact between the device and the underlying biological surface, even over a range of curved surfaces spatially varying over each of the three spatial dimensions.

The configuration of the device ensures that even when the device experiences substantial stresses, such as during application of the device to the skin, finger, or other region of the body, a majority of the components in the array remain functional. In an aspect, at least 70%, at least 90%, at least 95%, or about all of the components or functional electronic devices remain functional after application to the biological surface, including by manipulation of the surface orientation to ensure the array of components are inner-facing and positioned for physical and/or conformal contact with the skin.

In an aspect, the device inner volume is formed by flipping the array of components supported by the receiving surface from an outer-facing to an inner-facing configuration. This aspect is particularly relevant for those devices where the array of components is transfer printed to a physically-accessible surface, e.g., the outer-facing surface. Such an outer-facing surface is properly configured to provide conformal contact by flipping the substrate so that the previously positioned outer-surface corresponds to the inner-facing surface.

In an embodiment, the substrate forms an open-tube volume, where the substrate has two open ends, and between the open ends there is conformal contact with a biological surface. Such a configuration is relevant for devices that are slipped over an appendage with a portion of the appendage extremity not covered, such as a finger sleeve (e.g., fingertip less gloves), arm-band, leg-band or forehead-band, or wraps thereof. In this aspect, the inner volume does not have physical end surfaces, but instead ends defined by the edges of the substrate. Alternatively, the substrate forms a partially closed volume, such as for a finger confined by the fingertip portion of a glove. In this aspect, one end of the inner volume has a corresponding physical surface, with the other end open to receive the biological surface. In either embodiment, the inner volume may be defined by a depth and a diameter, or characteristic measures thereof, including for example by averaging over the entire substrate for those substrate shapes that are complicated (e.g., non-cylindrical).

The device is compatible, depending on the desired application, with any number or types of sensors, effectors, actuators or circuit elements, including as disclosed in any of 126-09, 29-11P, 134-06, 3-11, 7-11, 150-11, 38-04C, 38-04D and any other as provided hereinbelow, which are hereby explicitly incorporated by reference for the materials, components, configurations and methods of making and using, as disclosed therein.

In an aspect, the device is further characterized by any one or more relevant parameters, including dimensions, array characteristics including component number and density, and footprint surface area. Footprint surface area refers to the coverage area of the array, and corresponding area of the biological surface in conformal contact with the array of components. The device is well-suited for configuration over any size area, ranging from relatively small (e.g., 0.5 cm$^2$) to relatively large (e.g., 100 cm$^2$ or greater).

Also provided herein are related methods for making or for using any of the devices disclosed herein. Various physical characteristics of the devices provide the ability to specially manipulate the device to achieve functional benefit. For example, the substrate is capable of being shaped to any desired surface and an electronically active material transferred thereto. For transfer printing, the outer surface of the substrate is configured as a receiving surface of the electronically active material as the outer-facing surface is generally more accessible than an inner-facing surface. The deformability of the substrate provides the ability to then flip the receiving surface from an outer-facing configuration to an inner-facing configuration, thereby facilitating intimate contact between the electronically active material with a biological surface when the device is mounted or applied to the biological surface.

In an aspect, the invention provides a method of making appendage mountable electronic system, the method comprising the steps of: (i) providing a flexible or stretchable substrate having an initially inner facing surface defining an original enclosure; and an initially outer facing surface; (ii) transfer printing a flexible or stretchable electronic device comprising one or more sensors, actuators or both to the initially outer facing surface of the flexible or stretchable substrate; the sensors, actuators or both comprising one or more inorganic semiconductor components, one or more metallic components, or one or more inorganic semiconductor components and one or more metallic components; wherein at least a portion of the inorganic semiconductor components, metallic components or both has a thickness less than or equal to 500 microns; and (iii) flipping the elastomeric substrate so that after flipping the initially outer facing surface becomes a subsequently inner facing surface defining a final enclosure for receiving an appendage and the original inner facing surface becomes a subsequently outer facing surface, thereby providing the electronic device on the subsequently inner facing surface; wherein after the step of flipping the substrate the flexible or stretchable device remains functional.

In an embodiment, for example, the appendage is a hand, a finger, a finger-tip, a skull, a foot, a toe, a let, a torso, or any portion thereof. In an embodiment, for example, the step of providing the flexible or stretchable substrate comprises: (i) casting an elastomeric precursor against a surface of the appendage or a mold thereof; and (ii) curing the elastomeric precursor to obtain the flexible or stretchable substrate having an enclosure shape at rest that corresponds to a shape of the appendage. In an embodiment, for example, the step of transfer printing comprises transferring an array of actuators, sensors, or actuators and sensors, via a technique selected from the group consisting of microtransfer printing, dry contact transfer printing, solution-based printing, soft lithography printing, replica molding, and imprint lithography. In an embodiment, for example, the step of transfer printing comprises transferring the array of actuators, sensors, or actuators and sensors from an elastomeric transfer stamp to the initially outer surface of the elastic substrate. In an embodiment, for example, the step of the transfer printing further comprises flattening the elastomeric substrate into a flat geometry and transferring the array of actuators, sensors, or actuators and sensors to the elastic substrate in the flat geometry. In an embodiment, for example, the step of the transfer printing further comprises rolling the elastomeric transfer stamp over the outer surface of the elastic substrate in a curved geometry. In an embodiment, for example, the final enclosure has an inner surface shape that corresponds to a finger or a finger-tip surface shape. In an embodiment, for example, the system is incorporated into a finger or fingertip of a glove.

In an embodiment, for example, the step of transfer printing one or more sensors, actuators or both to the subsequently outer surface of the flexible or stretchable substrate, thereby providing a first sensor, or actuator or both on the subsequently inner surface and a second sensor, or actuator or both on the subsequently outer surface. In an embodiment, for example, the first sensor, or actuator or both comprises an array of electrotactile stimulators, and the sensor, or actuator or both comprises an array of tactile sensors. In an embodiment, for example, the method further comprises the step of communicably connecting the tactile sensors with the electrotactile sensors so that the electrotactile sensors are controlled by an output from the tactile sensors. In an embodiment, for example, the array of electrotactile sensors generate a spatially-varying pattern of electrical stimulation.

In an aspect, the substrate curvature is obtained by casting a polymer against a desired shape. The desired shape can be the biological surface itself, such as for a custom-fit application. Alternatively, the desired shape can itself be a mold of a biological surface shape. Alternatively, substrate curvature is achieved by a non-casting process, including by use of a commercially available substrate (e.g., a surgical glove).

An example of a method of making an appendage mountable electronic system by such a casting process is by: (i) providing an appendage or mold thereof; (ii) providing a flexible or stretchable electronic device comprising one or more sensors, actuators or both to a surface of the appendage or mold thereof; said sensors, actuators or both comprising one or more inorganic semiconductor components, one or more metallic components, or one or more inorganic semiconductor components and one or more metallic components; wherein at least a portion of said inorganic semiconductor components, metallic components or both has a thickness less than or equal to 500 microns; (iii) introducing a prepolymer to the flexible or stretchable electronic device supported by the surface of the appendage or mold thereof; and (iv) polymerizing the prepolymer to form a flexible or stretchable substrate having an inner surface that supports the flexible or stretchable electronic device. Optionally, the method further comprises the step of removing the substrate and flexible or stretchable electronic device from the surface of the appendage or mold thereof.

Any of the methods may further comprise the step of transfer printing a flexible or stretchable electronic device comprising one or more sensors, actuators or both to an outer surface of the flexible or stretchable substrate; said sensors, actuators or both comprising one or more inorganic semiconductor components, one or more metallic components, or one or more inorganic semiconductor components and one or more metallic components; wherein at least a portion of said inorganic semiconductor components, metallic components or both has a thickness less than or equal to 500 microns. In this manner, electronic devices are provided to both internal and external surfaces without having to flip the substrate surfaces.

In an embodiment, the transfer printing comprises transferring the electronically active material to the substrate that has been flattened. Alternatively, such as for a substrate that remains positioned against the user surface or mold thereof, the transfer printing can be to the curved surface, such as by a rotational or rolling motion of the stamp over the curved surface.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

Figure 1:
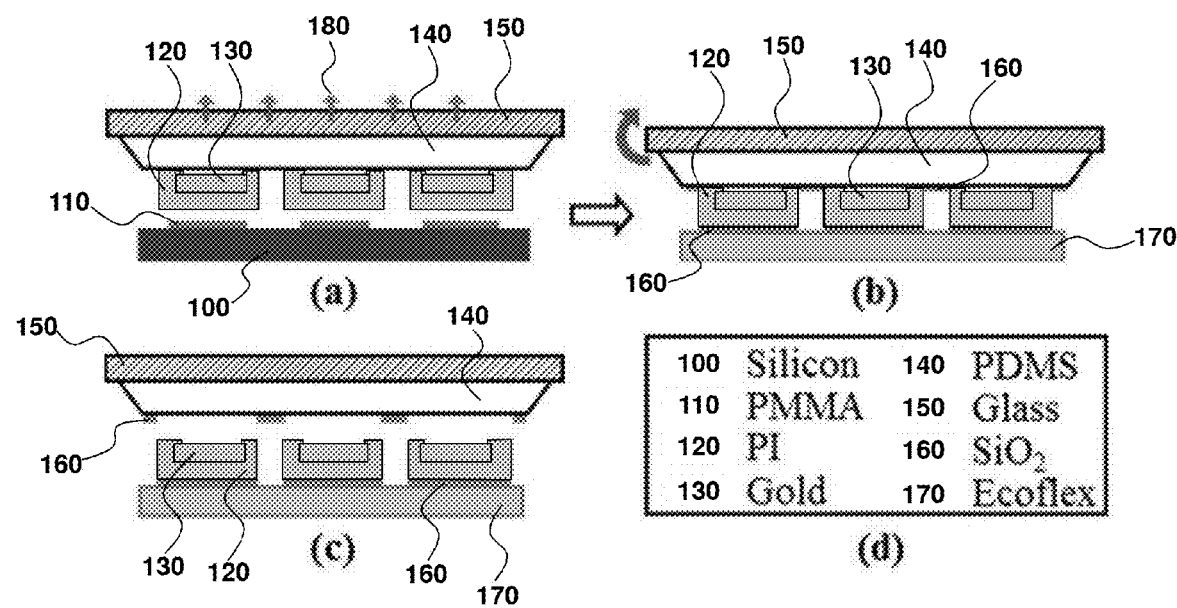
FIG. 1. Schematic illustration of the process for transfer printing an interconnected device structure from a substrate on which it is fabricated to an elastomeric sheet. (a) Interconnected sensors and electronics formed on a silicon wafer in an open mesh geometry are lifted onto the surface of a PDMS slab (i.e. stamp); (b) the backside of the mesh and the supporting PDMS stamp are coated with a thin layer of $SiO_2$ and then pressed onto an elastomeric sheet (Ecoflex); (c) removing the PDMS completes the transfer.

In general, the terms and phrases used herein have their art-recognized meaning, which can be found by reference to standard texts, journal references and contexts known to those skilled in the art. The following definitions are provided to clarify their specific use in the context of the invention.

"Enclosure", "interior volume", or "interior portion" are used interchangeably and refers to the space bounded by the inner surface of the elastomeric substrate. Accordingly, in aspects where the inner surface defines a small enclosure, or having an access opening that is small, the enclosure interior volume is correspondingly confined and not readily accessible from the outside. This confinement may make it not practical to reliably place and position functional electronic devices on the inner surface defining the enclosure. The invention is compatible with a wide range of substrates. For example, the substrate may be described in terms of various physical properties, such as a modulus or a thickness. In an embodiment, the modulus is a Young's modulus that is less than about 50 MPa, such as between about 100 kPa and 50 MPa. In an embodiment, the thickness is less than 1 mm, such as between about 0.1 mm and 1 mm.

As used herein, "conform" refers to a substrate which has a bending stiffness that is sufficiently low to allow the device, material or substrate to adopt any desired contour profile, for example a contour profile allowing for conformal contact with a surface having a three-dimensional curvature, including a curvature that may change over time or during use. The surface curvature may be highly irregular, in that the surface to be covered may have major surfaces that face each other. Accordingly, the conform aspect is not simply an overlay of a substantially two dimensional surface, but rather relates to covering a surface of a three-dimensional object having a defined volume.

"Appendage" is used broadly herein to refer to any three-dimensional object with a three-dimensional volume defined by one or more curved and/or planar surfaces. In certain embodiments, the appendage corresponds to living tissue. In an aspect, the appendage is a living tissue in a biological environment, such as part of a living animal. In an embodiment, the appendage surface corresponds to bone, skin or an epidermal layer of a living animal, including a human, so that the inner surface of the flexible or stretchable substrate conforms to one or more surface(s) of living tissue. Examples of appendages from a living animal include, but are not limited to, a hand, a finger, a finger-tip, a bone, a skull, a tooth, a head, a foot, a toe, a leg, an arm, a torso, a nose, an ear, genitalia or any portions thereof. In certain embodiments, the appendage corresponds to a non-living object, such as objects of remotely controlled instruments, robotics and the like, including for remote sensing applications. "Conformable" refers to a device, material or substrate which has a bending stiffness that is sufficiently low to allow the device, material and/or substrate to adopt any desired curved surface, for example for conformal contact with a surface having high curvatures. In certain embodiments, the curved surface is an appendage of a user.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface. In an embodiment, a method of the invention comprises establishing conformal contact between an inner surface of the elastomeric substrate that defines an enclosure and an object being inserted into the enclosure. Optionally, the conformal contact further includes one or more single crystalline inorganic semiconductor structures, one or more dielectric structures and/or one or more metallic conductor structures supported by the elastomeric substrate inner surface and a curved surface within the enclosure.

"Cover", as used herein refers to the conformal contact region between the elastomeric substrate inner surface and an object surface that is within the enclosure defined by the elastomeric substrate inner surface, specifically under a self-generated contact force that prevents relative movement between the two surfaces. In an aspect, the substrate portions that cover may have a constant and uniform thickness. In an aspect, the cover may have a spatial distribution of substrate thicknesses. Alternatively, cover includes embodiments where the substrate has perforations, such as a mesh or woven configuration, so as to permit surface breathability. The contact force may be uniformly distributed across the cover area or, alternatively, may be spatially distributed such as certain locations where it is critical the surfaces do not move with respect to each other having a higher contact force. That position could correspond, for example, to positions having a high functional electronic device density.

"Open mesh geometry" refers to a material having at least 20%, at least 40%, at least 60%, or at between about 20% and 80% of the surface area of the material that is open or void space, as defined by an outer perimeter of the material. Accordingly, the material may refer to electrical interconnects that overlay a substrate that may be a continuous surface or may itself be mesh. Interconnects having such an open mesh geometry are optionally tethered to a substrate surface either directly, or indirectly such as at ends connected to rigid device islands that are bonded to the substrate. Such mesh geometry may have a noticeable longitudinally-defined axis, including multiple axis having different alignments to facilitate bending and stretching in more than one direction. In an aspect, the mesh has two directions that are orthogonal or substantially orthogonal with respect to each other. In an aspect, substantially orthogonal refers to within about 10° of absolute perpendicular.

"Closed tube geometry" refers to a substrate having ends that are constrained and unable to move without substantially affecting other portions of the substrate. One example of a closed tube geometry is ends of a rectangular substrate that are joined into a cylindrical tube, for example.

Any of the flexible or stretchable substrates can be further defined in terms of "lateral dimensions", such as lateral dimensions for receiving an appendage surface. Examples of lateral dimensions include a length, diameter or perimeter along selected cross-sections. The substrate may also be defined in terms of a surface area, such as a surface area available for conformal contact to a surface of the appendage or for contact with an external surface. One advantage of the systems and methods provided herein is that they are compatible with a wide range of dimensions and are selected depending on the application of interest, ranging from 1 mm to 10 cm for small scale, up to and including 10 cm to 1000 cm scale for larger scale applications.

A central aspect of the various embodiments is an elastomeric substrate that provides a self-generated force to provide and maintain intimate and conformal contact with an object surface in the enclosure. Accordingly, one aspect of any of the devices and methods provided herein is an enclosure having an expandable and adjustable interior volume (in terms of both magnitude and shape) so as to accommodate or receive objects that are bigger than the at-rest enclosure volume or size. For example, a substrate that stretches or is actively stretched to accommodate a curved surface within the enclosure or interior portion, so that the inner surface is in conformal contact with the surface. This can be achieved such as by a substrate interior volume that is sized smaller than the to-be-received surface for an interior volume that is a closed surface. Alternatively, such as for an interior volume that is open, the substrate may be wrapped around the surface under tension, thereby ensuring intimate and conformal contact between an inner surface and the accommodated surface. The ends of the substrate may be fixed in position by an adhesive, a bonding mechanism (e.g., snaps, Velcro, hooks, and the like), or via self-adhesion. This aspect of a self-generated contact force to provide and maintain conformal contact, is particularly useful under strenuous operating conditions that would otherwise adversely affect conformal contact and, therefore, device fidelity. For example, a relatively high contact force may be employed in conditions involving vigorous and substantial movement and forces.

"Interchangeably flippable" refers to a substrate that can be turned inside-out without permanently impacting a substrate mechanical property or adversely affecting a functionality parameter of the functional electronic device.

"Functionality parameter" is used to assess whether an electronic device remains functional and/or the degree of functionality or damage. For example, many of the devices and methods provided herein relate to flipping of surfaces to which functional electronic devices are supported. Such flipping is associated with relatively high localized stresses, strains and bending moments. One important functional benefit of the instant invention is the ability to perform such flipping without adversely impacting the associated devices or device components. Conventional electronic devices that are not bendable and flexibly either break outright or have their functionality severely impacted by the act of surface flipping. One manner of quantifying this functional benefit is by comparing device performance before and after the flipping, referred broadly herein as a "functionality parameter". In an aspect, functionality parameter can reflect whether a functional electronic device is operating by assessing the output based on an input that is a physical signal (for a sensor) or an electronic input (for an actuator). This indication is appropriate for assessing degree of non-functionality by deviation for the equivalent input prior to flipping, or total non-functionality. In this case, a user-selected tolerance is selected, such as outputs that within 20%, within 10%, or within 5%, reflected as satisfying functionality. "Without substantial degradation" of a functionality parameter refers to a device satisfying the 20%, 10%, or 5% tolerance when referring to an individual functional electronic device. In an array aspect, it refers to at least 80%, at least 90%, or at least 95% of the array devices remaining functional after flipping.

"Functional electronic device" refers to an electronic device, such as a sensor or actuator, which interfaces with a surface that is brought into contact with the device. A functional electronic device provides useful information about the interfacing. For example, for tactile sensors the device provides an output that is proportional to a force between the sensor and the surface. For an electrotactile stimulator, there is an electric stimulation or actuation of a nerve underlying the stimulator. A positioning sensor, in contrast, provides an output that is based on the movement of the sensor and so does not interface with a surface, per se, but is still included within the scope of functional electronic device. Accordingly, "functional electronic device" is used broadly herein and includes any sensors or actuators having suitably thin geometry and layouts to maintain or facilitate high degree of flexibility and stretchability. Examples of functional electronic devices include: electrodes, actuators, strain sensors, motion sensors, displacement sensors, acceleration sensors, pressure sensors, force sensors, chemical sensors, pH sensors, tactile sensors, optical sensors, electromagnetic radiation sources, temperature sensors, heat sources, capacitive sensors; and combinations thereof. Tactile sensors provide an output that is proportional to a force between the sensor and the surface. An electrotactile stimulator provides an electric stimulation or actuation of a nerve underlying the stimulator, so as to provide a type of virtual reality system.

A "device component" is used broadly to refer to an individual part of a device but that, in and of itself, is insufficient to provide functional information. An "interconnect" is one example of a component, and refers to an electrically conducting structure capable of establishing an electrical connection with another component or between components. In particular, an interconnect may establish electrical contact between components that are separate. Depending on the desired device specifications, operation, and application, an interconnect is made from a suitable material. Suitable conductive materials include semiconductors and metallic conductors. Another useful device component is a thin nanomembrane, which may form part of a diode. Accordingly, a functional electronic device may be characterized as made up of a device component.

Other components include, but are not limited to, thin film transistors (TFTs), transistors, diodes, electrodes, integrated circuits, circuit elements, control elements, photovoltaic elements, photovoltaic elements (e.g. solar cell), sensors, light emitting elements, actuators, piezoelectric elements, receivers, transmitters, microprocessors, transducers, islands, bridges and combinations thereof. Components may be connected to one or more contact pads as known in the art, such as by metal evaporation, wire bonding, and application of solids or conductive pastes, for example, thereby forming device islands. Electronic devices of the invention may comprise one or more components, optionally provided in an interconnected configuration.

"Electronic device" generally refers to a device incorporating a plurality of components and functional electronic devices, and includes large area electronics, printed wire boards, integrated circuits, arrays, biological and/or chemical sensors, physical sensors (e.g., temperature, strain, etc.), nanoelectromechanical systems, microelectromechanical systems, photovoltaic devices, communication systems, medical devices, optical devices and electro-optic devices. An electronic device may sense a property of the surface and/or may control a property of the surface.

"Sensing" and "sensor" refers to a functional electronic device or device component useful for detecting the presence, absence, amount, magnitude or intensity of a physical, biological state, and/or chemical property. Useful electronic device components for sensing include, but are not limited to electrode elements, chemical or biological sensor elements, pH sensors, temperature sensors, tactile sensors, strain sensors, mechanical sensors, position sensors, optical sensors and capacitive sensors. Useful functional electronic devices include various device components operably arranged to provide electrodes for detecting adjacent electric potential, sensors for detecting a biological condition (e.g., disease state, cell type, cell condition) or a chemical, pH, temperature, pressure, position, electromagnetic radiation (including over desired wavelengths such as associated with a fluorescent dye injected into tissue), electric potential.

"Actuating" and "actuator" refers to a functional electronic device or device component useful for interacting with, stimulating, controlling, or otherwise affecting an external structure, material or fluid, for example a target tissue that is biological tissue. Useful actuating elements include, but are not limited to, electrode elements, electromagnetic radiation emitting elements, light emitting diodes, lasers and heating elements. Functional electronic devices include actuators that are electrodes for providing a voltage or current to a tissue, sources of electromagnetic radiation for providing electromagnetic radiation to a tissue, such as LEDs. Actuators also include ablation sources for ablating tissue, thermal sources for heating tissue, displacement sources for displacing or otherwise moving a tissue, reservoirs of biologics or chemicals for releasing biologics or chemicals to affect biological function, such as a biological response including cell death, cell proliferation, or cell therapy by application of biologics or chemicals. An actuator may be an electrotactile sensor.

A "tactile sensor" refers to a transducer that is sensitive to touch, such as by transducing force or pressure into a voltage output from the sensor. An "electrotactile stimulator" refers to an electronic device that electrically stimulates nerves of the skin to simulate a sensation, and may be classified as an actuator.

"Semiconductor" refers to any material that is an insulator at a very low temperature, but which has an appreciable electrical conductivity at a temperature of about 300 Kelvin. In the present description, use of the term semiconductor is intended to be consistent with use of this term in the art of microelectronics and electronic devices. Useful semiconductors include those comprising elemental semiconductors, such as silicon, germanium and diamond, and compound semiconductors, such as group IV compound semiconductors such as SiC and SiGe, group III-V semiconductors such as AlSb, AlAs, AlN, AlP, BN, BP, BAs, GaSb, GaAs, GaN, GaP, InSb, InAs, InN, and InP, group III-V ternary semiconductors alloys such as $Al_xGa_{1-x}As$, group II-VI semiconductors such as CsSe, CdS, CdTe, ZnO, ZnSe, ZnS, and ZnTe, group I-VII semiconductors such as CuCl, group IV-VI semiconductors such as PbS, PbTe, and SnS, layer semiconductors such as $PbI_2$, $MoS_2$, and GaSe, oxide semiconductors such as CuO and $Cu_2O$. The term semiconductor includes intrinsic semiconductors and extrinsic semiconductors that are doped with one or more selected materials, including semiconductors having p-type doping materials and n-type doping materials, to provide beneficial electronic properties useful for a given application or device. The term semiconductor includes composite materials comprising a mixture of semiconductors and/or dopants. Specific semiconductor materials useful for some embodiments include, but are not limited to, Si, Ge, Se, diamond, fullerenes, SiC, SiGe, SiO, $SiO_2$, SiN, AlSb, AlAs, AlIn, AlN, AlP, AlS, BN, BP, BAs, $As_2S_3$, GaSb, GaAs, GaN, GaP, GaSe, InSb, InAs, InN, InP, CsSe, CdS, CdSe, CdTe, $Cd_3P_2$, $Cd_3As_2$, $Cd_3Sb_2$, ZnO, ZnSe, ZnS, ZnTe, $Zn_3P_2$, $Zn_3As_2$, $Zn_3Sb_2$, $ZnSiP_2$, CuCl, PbS, PbSe, PbTe, FeO, $FeS_2$, NiO, EuO, EuS, PtSi, $TlBr$, $CrBr_3$, SnS, SnTe, $PbI_2$, $MoS_2$, GaSe, CuO, $Cu_2O$, HgS, HgSe, HgTe, $HgI_2$, MgS, MgSe, MgTe, CaS, CaSe, SrS, SrTe, BaS, BaSe, BaTe, $SnO_2$, TiO, $TiO_2$, $Bi_2S_3$, $Bi_2O_3$, $Bi_2Te_3$, $BiI_3$, $UO_2$, $UO_3$, $AgGaS_2$, PbMnTe, $BaTiO_3$, $SrTiO_3$, $LiNbO_3$, $La_2CuO_4$, $La_{0.7}Ca_{0.3}Mn_{0.3}$, CdZnTe, CdMnTe, $CuInSe_2$, copper indium gallium selenide (CIGS), HgCdTe, HgZnTe, HgZnSe, PbSnTe, $Tl_2SnTe_5$, $Tl_2GeTe_5$, AlGaAs, AlGaN, AlGaP, AlInAs, AlInSb, AlInP, AlInAsP, AlGaAsN, GaAsP, GaAsN, GaMnAs, GaAsSbN, GaInAs, GaInP, AlGaAsSb, AlGaAsP, AlGaInP, GaInAsP, InGaAs, InGaP, InGaN, InAsSb, InGaSb, InMnAs, InGaAsP, InGaAsN, InAlAsN, GaInNAsSb, GaInAsSbP, and any combination of these. Porous silicon semiconductor materials are useful for aspects described herein. Impurities of semiconductor materials are atoms, elements, ions and/or molecules other than the semiconductor material(s) themselves or any dopants provided to the semiconductor material. Impurities are undesirable materials present in semiconductor materials which may negatively impact the electronic properties of semiconductor materials, and include but are not limited to oxygen, carbon, and metals including heavy metals. Heavy metal impurities include, but are not limited to, the group of elements between copper and lead on the periodic table, calcium, sodium, and all ions, compounds and/or complexes thereof.

A "semiconductor component" broadly refers to any semiconductor material, composition or structure, and expressly includes high quality single crystalline and polycrystalline semiconductors, semiconductor materials fabricated via high temperature processing, doped semiconductor materials, inorganic semiconductors, and composite semiconductor materials.

"Nanostructured material" and "microstructured material" refer to materials having one or more nanometer-sized and micrometer-sized, respectively, physical dimensions (e.g., thickness) or features such as recessed or relief features, such as one or more nanometer-sized and micrometer-sized channels, voids, pores, pillars, etc. The relief features or recessed features of a nanostructured material have at least one physical dimension selected from the range of 1-1000 nm, while the relief features or recessed features of a microstructured material have at least one physical dimension selected from the range of 1-1000 μm. Nanostructured and microstructured materials include, for example, thin films (e.g., microfilms and nanofilms), porous materials, patterns of recessed features, patterns of relief features, materials having abrasive or rough surfaces, and the like. A nanofilm structure is also an example of a nanostructured material and a microfilm structure is an example of a microstructured material. In an embodiment, the invention provides device comprising one or more nanostructured or microstructured inorganic semiconductor components, one or more nanostructured or microstructured metallic conductor components, one or more nanostructured or microstructured dielectric components, one or more nanostructured or microstructured encapsulating layers and/or one or more nanostructured or microstructured substrate layers.

A component may be a nanomembrane material. A "nanomembrane" is a structure having a thickness selected from the range of 1-1000 nm or alternatively for some applications a thickness selected from the range of 1-100 nm, for example provided in the form of a ribbon, cylinder or platelet. In some embodiments, a nanoribbon is a semiconductor, dielectric or metallic conductor structure of an electronic device. In some embodiments, a nanoribbon has a thickness less than 1000 nm and optionally less than 100 nm. In some embodiments, a nanoribbon has ratio of thickness to a lateral dimension (e.g., length or width) selected from the range of 0.1 to 0.0001.

"Neutral mechanical plane" (NMP) refers to an imaginary plane existing in the lateral, b, and longitudinal, l, directions of a device. The NMP is less susceptible to bending stress than other planes of the device that lie at more extreme positions along the vertical, h, axis of the device and/or within more bendable layers of the device. Thus, the position of the NMP is determined by both the thickness of the device and the materials forming the layer(s) of the device. In an embodiment, a device of the invention includes one or more inorganic semiconductor components, one or more metallic conductor components or one or more inorganic semiconductor components and one or more metallic conductor components provided coincident with, or proximate to, the neutral mechanical plane of the device. Examples of a variety of NMP systems incorporating multiple layers are provided, for example, in U.S. Pat. Pub. No. 2010/0002402 (Atty Ref 213-07), which is specifically incorporated by reference for methods of positioning NMP.

"Coincident" refers to the relative position of two or more objects, planes or surfaces, for example a surface such as a neutral mechanical plane that is positioned within or is adjacent to a layer, such as a functional layer, substrate layer, or other layer. In an embodiment, a neutral mechanical plane is positioned to correspond to the most strain-sensitive layer or material within the layer.

"Proximate" refers to the relative position of two or more objects, planes or surfaces, for example a neutral mechanical plane that closely follows the position of a layer, such as a functional layer, substrate layer, or other layer while still providing desired conformability without an adverse impact on the strain-sensitive material physical properties. "Strain-sensitive" refers to a material that fractures or is otherwise impaired in response to a relatively low level of strain. In general, a layer having a high strain sensitivity, and consequently being prone to being the first layer to fracture, is located in the functional layer, such as a functional layer containing a relatively brittle semiconductor or other strain-sensitive device element. A neutral mechanical plane that is proximate to a layer need not be constrained within that layer, but may be positioned proximate or sufficiently near to provide a functional benefit of reducing the strain on the strain-sensitive device element when the device is conformed to a tissue surface. In some embodiments, proximate to refers to a position of a first element within 100 microns of a second element, or optionally within 10 microns for some embodiments, or optionally within 1 microns for some embodiments.

A "component" is used broadly to refer to a material or individual component used in a device. An "interconnect" is one example of a component and refers to an electrically conducting material capable of establishing an electrical connection with a component or between components. In particular, an interconnect may establish electrical contact between components that are separate and/or can move with respect to each other. Depending on the desired device specifications, operation, and application, an interconnect is made from a suitable material. For applications where a high conductivity is required, typical interconnect metals may be used, including but not limited to copper, silver, gold, aluminum and the like, and alloys. Suitable conductive materials further include semiconductors, such as silicon and GaAs and other conducting materials such as indium tin oxide.

An interconnect that is "stretchable" or "flexible" is used herein to broadly refer to an interconnect capable of undergoing a variety of forces and strains such as stretching, bending and/or compression in one or more directions without adversely impacting electrical connection to, or electrical conduction from, a device component. Accordingly, a stretchable interconnect may be formed of a relatively brittle material, such as GaAs, yet remain capable of continued function even when exposed to a significant deformatory force (e.g., stretching, bending, compression) due to the interconnect's geometrical configuration. In an exemplary embodiment, a stretchable interconnect may undergo strain larger than 1%, optionally 10% or optionally 30% or optionally up to 100% without fracturing. In an example, the strain is generated by stretching an underlying elastomeric substrate to which at least a portion of the interconnect is bonded. For certain embodiments, flexible or stretchable interconnects include interconnects having wavy, meandering or serpentine shapes.

In the context of this description, a "bent configuration" refers to a structure having a curved conformation resulting from the application of a force. Bent structures may have one or more folded regions, convex regions, concave regions, and any combinations thereof. Useful bent structures, for example, may be provided in a coiled conformation, a wrinkled conformation, a buckled conformation and/or a wavy (i.e., wave-shaped) configuration. Bent structures, such as stretchable bent interconnects, may be bonded to a flexible substrate, such as a polymer and/or elastic substrate, in a conformation wherein the bent structure is under strain. In some embodiments, the bent structure, such as a bent ribbon structure, is under a strain equal to or less than 30%, optionally a strain equal to or less than 10%, optionally a strain equal to or less than 5% and optionally a strain equal to or less than 1% in embodiments preferred for some applications. In some embodiments, the bent structure, such as a bent ribbon structure, is under a strain selected from the range of 0.5% to 30%, optionally a strain selected from the range of 0.5% to 10%, and optionally a strain selected from the range of 0.5% to 5%. Alternatively, the stretchable bent interconnects may be bonded to a substrate that is a substrate of a device component, including a substrate that is itself not flexible. The substrate itself may be planar, substantially planar, curved, have sharp edges, or any combination thereof. Stretchable bent interconnects are available for transferring to any one or more of these complex substrate surface shapes.

A "device component" is used to broadly refer to an individual component within an electrical, optical, mechanical or thermal device. Components include, but are not limited to, a photodiode, LED, TFT, electrode, semiconductor, other light-collecting/detecting components, transistor, integrated circuit, contact pad capable of receiving a device component, thin film devices, circuit elements, control elements, microprocessors, transducers and combinations thereof. A device component can be connected to one or more contact pads as known in the art, such as metal evaporation, wire bonding, application of solids or conductive pastes, for example. Electrical device generally refers to a device incorporating a plurality of device components, and includes large area electronics, printed wire boards, integrated circuits, device components arrays, biological and/or chemical sensors, physical sensors (e.g., temperature, light, radiation, etc.), solar cell or photovoltaic arrays, display arrays, optical collectors, systems and displays.

"Island" or "device island" refers to a relatively rigid device element or component of an electronic device comprising multiple semiconductor elements or active semiconductor structures. "Bridge" or "bridge structure" refers to stretchable or flexible structures interconnecting two or more device islands or one device island to another device component. Specific bridge structures include flexible semiconductor interconnects.

"Encapsulate" refers to the orientation of one structure such that it is at least partially, and in some cases completely, surrounded by one or more other structures, such as a substrate, adhesive layer or encapsulating layer. "Partially encapsulated" refers to the orientation of one structure such that it is partially surrounded by one or more other structures, for example, wherein 30%, or optionally 50% or optionally 90%, of the external surfaces of the structure is surrounded by one or more structures. "Completely encapsulated" refers to the orientation of one structure such that it is completely surrounded by one or more other structures. The invention includes devices having partially or completely encapsulated inorganic semiconductor components, metallic conductor components and/or dielectric components, for example, via incorporation a polymer encapsulant, such as an elastomer encapsulant.

"Barrier layer" refers to a device component spatially separating two or more other device components or spatially separating a device component from a structure, material or fluid external to the device. In one embodiment, a barrier layer encapsulates one or more device components. In embodiments, a barrier layer separates one or more device components from an aqueous solution, a biological tissue and/or a biological environment. In some embodiments, a barrier layer is a passive device component. In some embodiments, a barrier layer is a functional, but non-active, device component. In a specific embodiment, a barrier layer is a moisture barrier. As used herein, the term "moisture barrier" refers to a barrier layer which provides protection to other device components from bodily fluids, ionic solutions, water or other solvents. In one embodiment, a barrier layer provides protection to an external structure, material or fluid, for example, by preventing leakage current from escaping an encapsulated device component and reaching the external structure, material or fluid. In a specific embodiment, a barrier layer is a thermal barrier. As used herein, the term "thermal barrier" refers to a barrier layer which acts as a thermal insulator, preventing, reducing or otherwise limiting the transfer of heat from one device component to another or from a device component to an external structure, fluid or material. Useful thermal barriers include those comprising materials having a thermal conductivity of 0.3 W/m·K or less, such as selected over the range of 0.001 to 0.3 W/m·K. In some embodiments, a thermal barrier comprises active cooling components, such as components known in the art of thermal management, such as thermoelectric cooling devices and systems. Thermal barriers also include those barriers comprising thermal management structures, such as structures useful for transporting heat away from a portion of a device or tissue; in these and other embodiments, a thermal barrier comprises thermally conductive material, for example material having a high thermal conductivity, such as a thermal conductivity characteristic of a metal.

"Biocompatible" refers to a material that does not elicit an immunological rejection or detrimental effect, referred herein as an adverse immune response, when it is disposed within an in-vivo biological environment. For example, a biological marker indicative of an immune response changes less than 10%, or less than 20%, or less than 25%, or less than 40%, or less than 50% from a baseline value when a biocompatible material is implanted into a human or animal. Alternatively, immune response may be determined histologically, wherein localized immune response is assessed by visually assessing markers, including immune cells or markers that are involved in the immune response pathway, in and adjacent to the implanted device. In an aspect, a biocompatible device does not observably change immune response as determined histologically. In some embodiments, the invention provides biocompatible devices configured for long-term implantation, such as on the order of weeks to months, without invoking an adverse immune response. The implantation does contemplate some immune response and associated scarring as may occur for any minimally invasive procedures, so long as the immune response is locally confined, transient and does not lead to large-scale inflammation and attendant deleterious effects and the implanted device does not substantially elevate the response compared to the corresponding physical trauma only.

"Bioinert" refers to a material that does not elicit an immune response from a human or animal when it is disposed within an in-vivo biological environment. For example, a biological marker indicative of an immune response remains substantially constant (plus or minus 5% of a baseline value) when a bioinert material is implanted into a human or animal. In some embodiments, the invention provides bioinert systems, devices and related methods.

"Multiplexed" refers to an electronic circuit to provide convenient control over an array of elements. For example, PCT Pub. WO2011/084450 (126-09WO) describes multiplexing circuits in electrophysiology applications, which is specifically incorporated by reference. Other examples include, U.S. Patent Application Publication 2003/0149456 discloses a multi-electrode cardiac lead adapter which incorporates a multiplexing circuit allowing for control by a conventional single lead cardiac pacing pulse generator. Similarly, U.S. Patent Application Publication 2006/0173364 discloses a multichannel electrophysiology acquisition system which utilizes a digital multiplexing circuit build on a conventional integrated circuit.

"Ultrathin" refers to devices of thin geometries that exhibit extreme levels of bendability. In an embodiment, ultrathin refers to circuits having a thickness less than 1 µm, less than 600 nm or less than 500 nm. In an embodiment, a multilayer device that is ultrathin has a thickness less than 200 µm, less than 50 µm, or less than 10 µm.

"Thin layer" refers to a material that at least partially covers an underlying substrate, wherein the thickness is less than or equal to 300 µm, less than or equal to 200 µm, or less than or equal to 50 µm. Alternatively, the layer is described in terms of a functional parameter, such as a thickness that is sufficient to isolate or substantially reduce the strain on the electronic device, and more particularly a functional layer in the electronic device that is sensitive to strain.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomeric stamp" and "elastomeric transfer device" are used interchangeably and refer to an elastomeric material having a surface that can receive as well as transfer a material. Exemplary conformal transfer devices useful in some methods of the invention include elastomeric transfer devices such as elastomeric stamps, molds and masks. The transfer device affects and/or facilitates material transfer from a donor material to a receiver material. In an embodiment, a method of the invention uses a conformal transfer device, such as an elastomeric transfer device (e.g. elastomeric stamp) in a microtransfer printing process, for example, to transfer one or more single crystalline inorganic semiconductor structures, one or more dielectric structures and/or one or more metallic conductor structures from a fabrication substrate to a device substrate.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. In some embodiments, an elastomeric stamp comprises an elastomer. Exemplary elastomers include, but are not limited to silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly (phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a polymer is an elastomer.

"Young's modulus" is a mechanical property of a material, device or layer which refers to the ratio of stress to strain for a given substance. Young's modulus may be provided by the expression:

$$E = \frac{(\text{stress})}{(\text{strain})} = \left(\frac{L_0}{\Delta L}\right)\left(\frac{F}{A}\right), \quad (I)$$

where E is Young's modulus, $L_0$ is the equilibrium length, $\Delta L$ is the length change under the applied stress, F is the force applied, and A is the area over which the force is applied. Young's modulus may also be expressed in terms of Lame constants via the equation:

$$E = \frac{\mu(3\lambda + 2\mu)}{\lambda + \mu}, \quad (II)$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably about 10 times larger for some applications, more preferably about 100 times larger for other applications, and even more preferably about 1000 times larger for yet other applications. In an embodiment, a low modulus layer has a Young's modulus less than 100 MPa, optionally less than 10 MPa, and optionally a Young's modulus selected from the range of 0.1 MPa to 50 MPa. In an embodiment, a high modulus layer has a Young's modulus greater than 100 MPa, optionally greater than 10 GPa, and optionally a Young's modulus selected from the range of 1 GPa to 100 GPa. In an embodiment, a device of the invention has one or more components, such as substrate, encapsulating layer, inorganic semiconductor structures, dielectric structures and/or metallic conductor structures, having a low Young's modulus. In an embodiment, a device of the invention has an overall low Young's modulus.

"Inhomogeneous Young's modulus" refers to a material having a Young's modulus that spatially varies (e.g., changes with surface location). A material having an inhomogeneous Young's modulus may optionally be described in terms of a "bulk" or "average" Young's modulus for the entire material.

"Low modulus" refers to materials having a Young's modulus less than or equal to 10 MPa, less than or equal to 5 MPa or less than or equal to 1 MPa. In an aspect, the functional layer has a low modulus and the delivery substrate has a higher Young's modulus, such as 10 times, 100 times, or 1000 times larger than the functional layer Young's modulus.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

Figure 9:
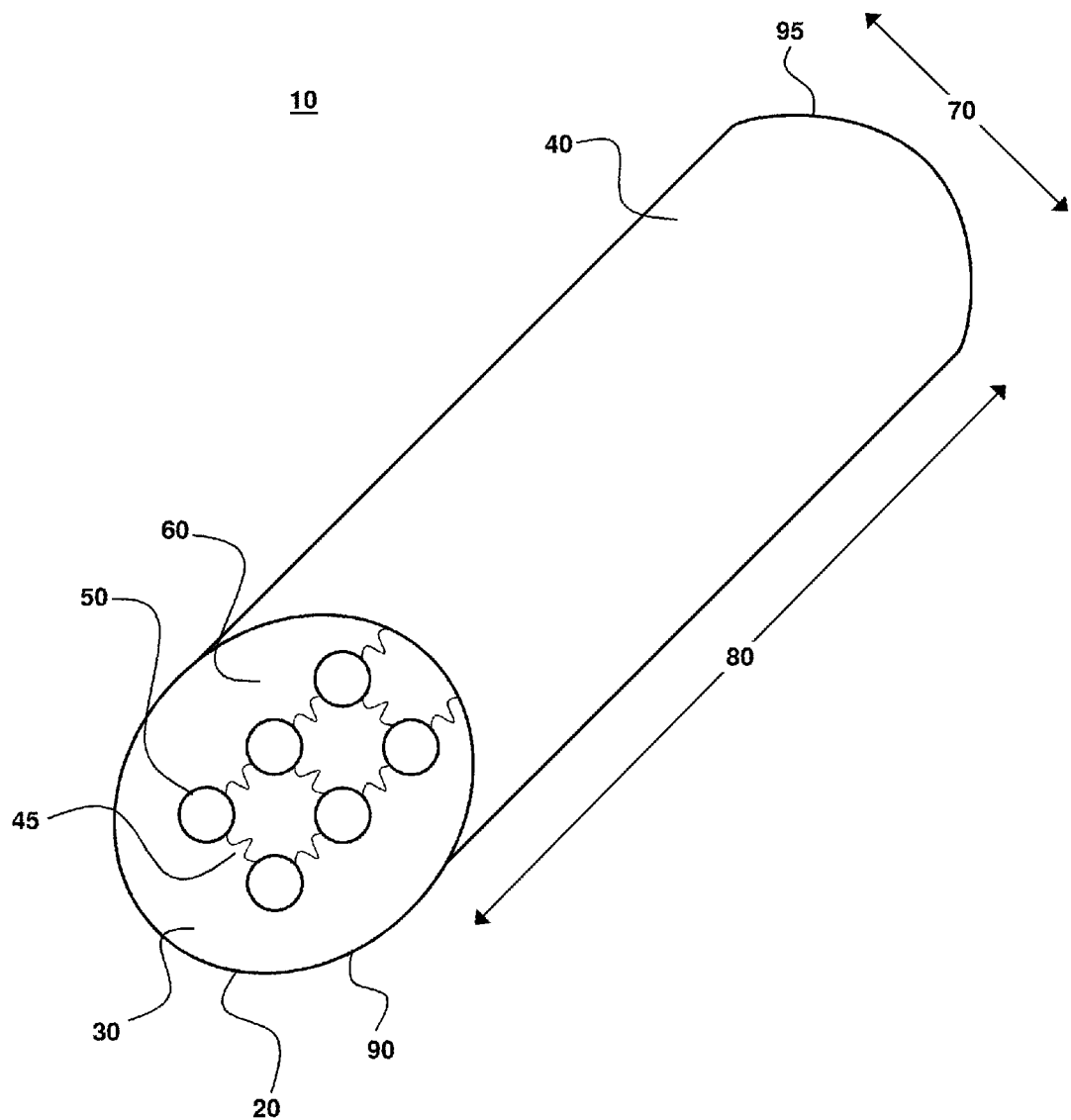
FIG. 9. Schematic illustration of an array of functional electronic devices on an inner surface of an elastomeric substrate.
Figure 10:
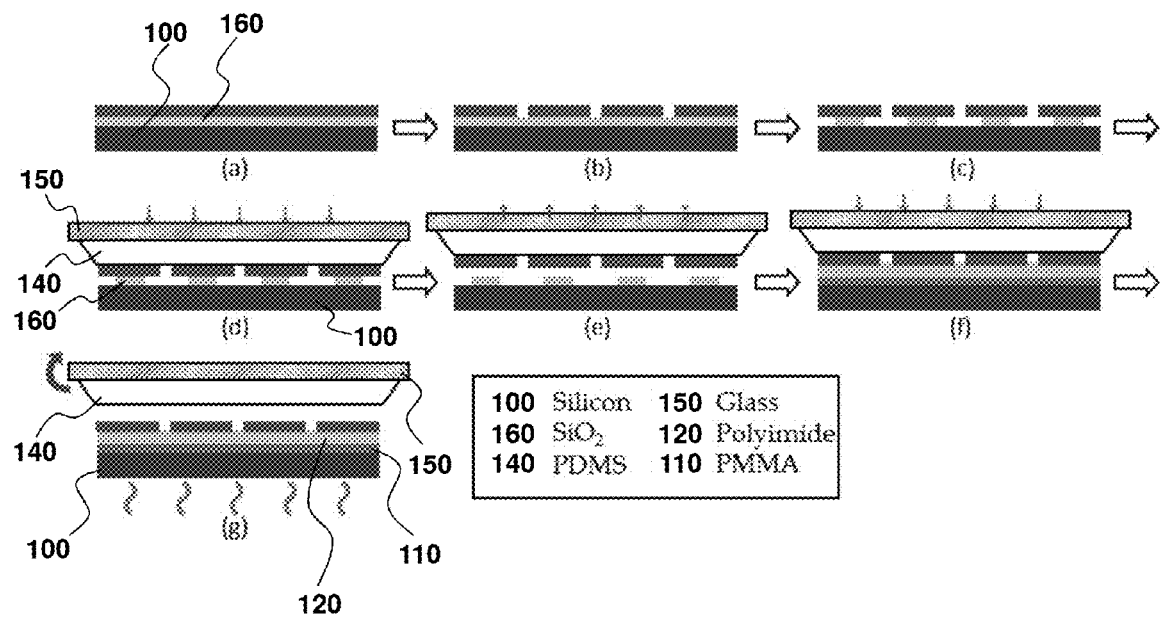
FIG. 10. Schematic of silicon transfer printing. (a) silicon on insulator (SOI) substrate; (b) RIE etch release holes (3 μm) in Si layer; (c) wet etch (buffered oxide etch) of SiO2 layer to release Si layer; (d) PDMS stamp pressed into contact with Si; (e) Si transfer to PDMS stamp upon removal; (f) PDMS stamp with transferred Si pressed onto PI layer; (g) After heating at 150° C. for 4 min, Si transferred to device upon stamp removal.
Figure 11:
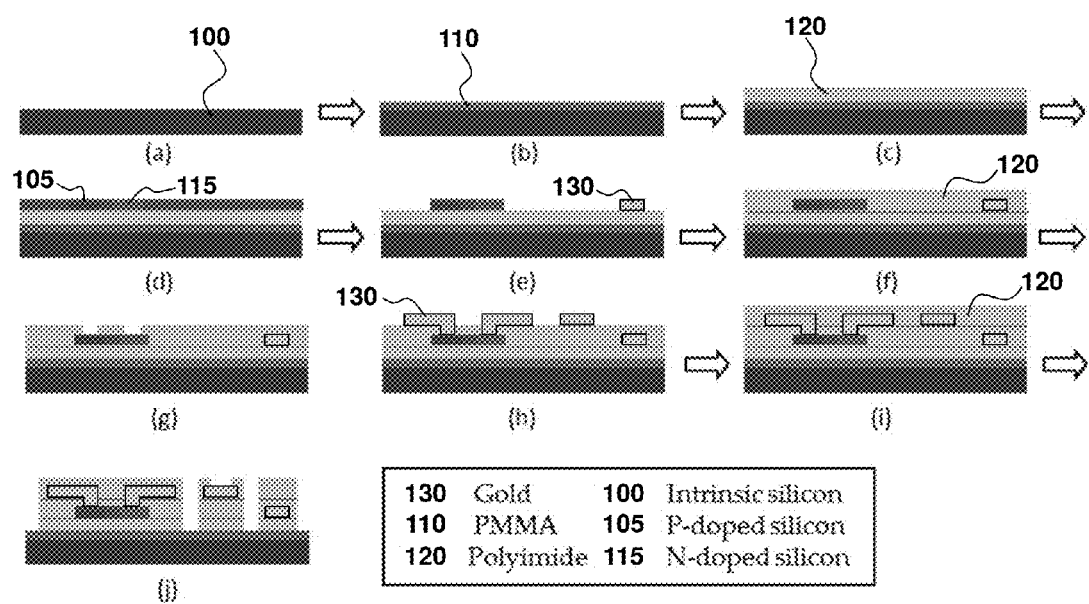
FIG. 11. Schematic of the fabrication process for electrotactile stimulators. (a) silicon substrate; (b) spin coat 100 nm sacrificial PMMA; (c) spin coat/250° C. bake 1.2 μm polyimide; (d) transfer of Si layer with PIN diodes (release holes not shown); (e) RIE isolation of Si nanomembrane PIN diodes and Au evaporation/patterning; (f) spin coat/250° C. bake 1.2 μm polyimide; (g) contact vias for diodes formed in PI with O2 RIE; (h) Au evaporation/patterning; (i) spin coat/250° C. bake 1.2 μm polyimide; (j) O2 RIE to form polyimide mesh structure and expose electrotactile electrodes.
Figure 12:
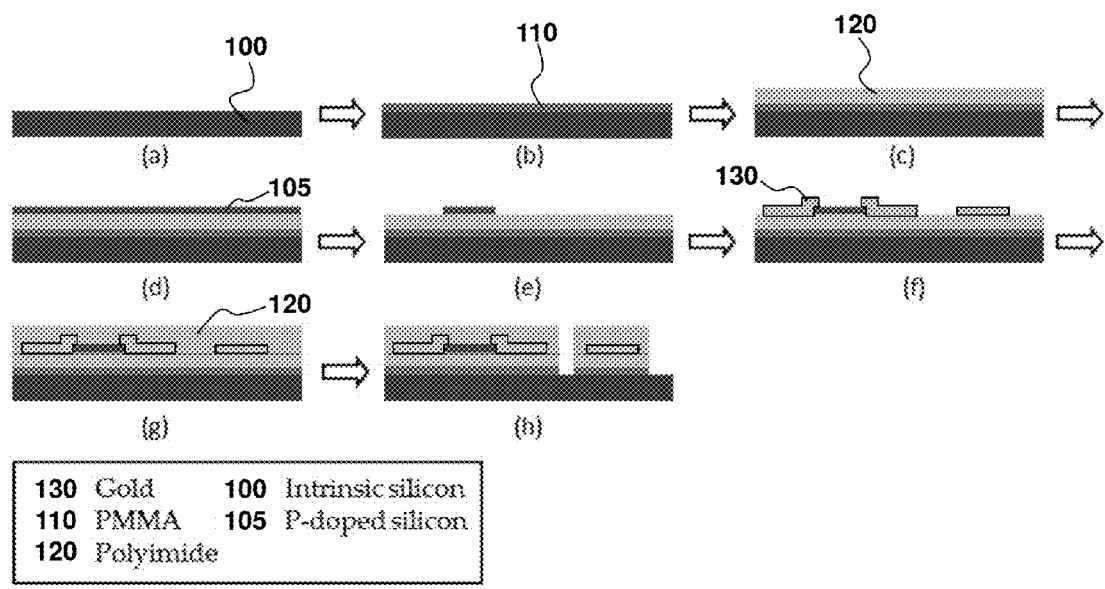
FIG. 12. Schematic of the fabrication process for strain gauges. (a) silicon substrate; (b) spin coat 100 nm sacrificial PMMA; (c) spin coat/250° C. bake 1.2 μm polyimide; (d) transfer of p-doped Si (release holes not shown); (e) RIE isolation of Si strain gauge nanomembranes; (f) Au evaporation/patterning; (g) spin coat/250° C. bake 1.2 μm polyimide; (h) O2 RIE to form polyimide mesh structure.
Figure 13:
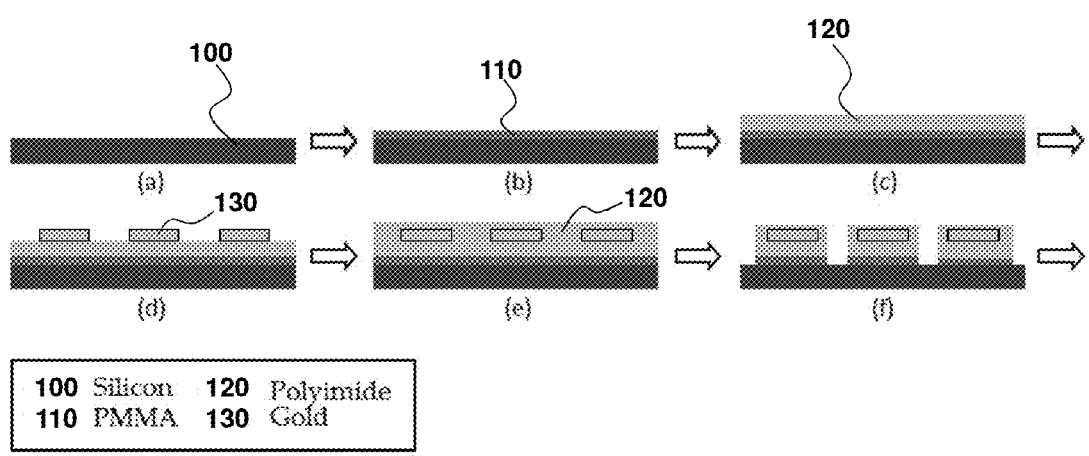
FIG. 13. Schematic of the fabrication process for tactile electrodes. (a) silicon substrate; (b) spin coat 100 nm sacrificial PMMA; (c) spin coat/250° C. bake 1.2 μm polyimide; (d) Au evaporation/patterning; (e) spin coat/250° C. bake 1.2 μm polyimide; (f) O2 RIE to form polyimide mesh structure.

An example of a device is schematically illustrated in FIG. 9. The electronic device 10 comprises a thin elastomeric substrate 20 with an inner surface 30 and an outer surface 40. An array of functional electronic devices 50 is illustrated as supported by the inner surface 30. The array comprises various device components, such as a flexible and stretchable interconnect in a curved configuration 45. The inner surface 30 defines an enclosure 60, having a characteristic dimension such as diameter 70 or length 80 between ends 90 and 95, or volume. Interior portion 60 is considered a closed volume as the substrate 20 does not have unbound ends that freely moved. Instead, movement of ends 80 and 90 are constrained. If ends 80 and 90 are able to freely move (such as if the tube were longitudinally cut), the device is considered to have an open-tube volume. Interior portion 60 can accommodate an object having a curved surface, even an irregular shaped object such as finger. Preferably, diameter 70 is slightly smaller than the maximum diameter of the object that is being received by the interior portion 60. Such a size difference requires the substrate 20 to stretch to receive the object, thereby ensuring tight conformal contact between the substrate 20, functional electronic devices 50, and the object surface within interior portion 60. For clarity, devices 50 are not shown on the outer surface 40. As explained further in Example 1, however, inner surface devices 50 may be provided by first printing functional electronic devices to the outer surface 40. The substrate surfaces may then be physically flipped, with the outer becoming the inner, and vice versa, to obtain the electronic device 10 illustrated in FIG. 9.

Example 1

Silicon Nanomembranes for Fingertip Electronics

This example relates to the use of semiconductor nanomaterials, advanced fabrication methods and unusual device designs for a class of electronics capable of integration onto the inner and the outer surfaces of thin, elastomeric sheets in closed-tube geometries, specially formed for mounting on the fingertips. Multifunctional systems of this type allow electrotactile stimulation with electrode arrays multiplexed using silicon nanomembrane (Si NM) diodes, high-sensitivity strain monitoring with Si NM gauges, and tactile sensing with elastomeric capacitors. Analytical calculations and finite element modeling of the mechanics quantitatively capture the key behaviors during fabrication/assembly, mounting and use. The results provide design guidelines that highlight the importance of the NM geometry in achieving the required mechanical properties. This type of technology is compatible with applications ranging from human-machine interfaces to 'instrumented' surgical gloves and many others.

Electrotactile stimulators and tactile sensors are of interest as bi-directional information links between a human operator and a virtual environment, in a way that could significantly expand function in touch-based interfaces to computer systems, with applications in simulated surgery, therapeutic devices, robotic manipulation and others [1-5]. Electrotactile stimulation allows information to be presented through the skin, as an artificial sensation of touch, commonly perceived as a vibration or tingling feeling [6,7]. Such responses manifest through the excitation of cutaneous mechanoreceptors as a result of passage of a suitably modulated electrical current into the tissue [8]. Developed originally in the 1950's and further advanced in the 1970's, electrotactile stimulation has been traditionally explored for programmable braille readers and displays for the visually impaired as well as for balance control in individuals who suffer from vestibular disorders [5, 9-12]. Tactile sensors, on the other hand, measure pressure created by physical contact, in a way that provides complementary information for potential use in feedback loops with the electrotactile process. Additional classes of sensors that can be important in this context include those for motion and temperature. Incorporating such technologies into a conformal, skin-like device capable of intimate, non-invasive mounting on the fingertips might, therefore, represent a useful achievement. Recent advances in flexible and stretchable electronics create opportunities to build this type of device [13-17].

Disclosed herein are materials, fabrication strategies and device designs for ultrathin, stretchable silicon-based electronics and sensors that can be mounted on the inner and outer surfaces of elastomeric closed-tube structures for integration directly on the fingertips. The active components and interconnects incorporate advanced mechanics designs, capable of accommodating large strains induced not only by natural deformations of the tubes during use, but also during a critical step in the fabrication process in which the tubes, specially formed to match the shapes of fingertips, are flipped inside-out. This 'flipping-over' process allows devices initially mounted on the outer surface of the tube to be reversed to the inner surface, where they can press directly against the skin when mounted on the fingers. Analytical calculations and finite element modeling (FEM) provide quantitative insights into design layouts that avoid plastic deformation or fracture. We demonstrate these concepts in multifunctional fingertip devices that include electrotactile electrode arrays multiplexed with Si nanomembrane (NM) diodes, strain sensors based on Si NM gauges, and tactile sensor arrays that use capacitors with low-modulus, elastomeric dielectrics.

FIG. 1 schematically illustrates steps for integrating devices based on Si NMs in stretchable, interconnected geometries with elastomeric substrates, following adapted versions of procedures described elsewhere [13, 18]. The fabrication uses a Si wafer with a 100 nm thick coating of polymethylmethacrylate (PMMA) as a temporary substrate for the initial parts of the process. A layer of polyimide (PI; 1.25 µm thick) formed by spin coating a poly (amic acid) precursor and baking in an inert atmosphere at 250° C., serves as the support for the devices. Electronically active materials are deposited (e.g. metallization) or transfer printed (e.g. Si NMs) onto the PI and patterned by photolithography and etching. Another layer of PI (1.25 mm thick) spin cast and cured on top of the device layers provides encapsulation and locates the devices near the neutral mechanical plane (NMP). Next, patterned reactive ion etching through the entire multilayer stack (i.e. PI/devices/PI) defines an open mesh structure. This same process removes PI in regions of the electrotactile stimulation electrodes, to allow direct contact with the skin. Immersion in an acetone bath washes away the underlying PMMA, thereby allowing the entire mesh to be lifted off, in a single piece, onto the surface of a flat slab of polydimethylsiloxane (PDMS), using procedures described previously [19,20]. Evaporating a layer of $SiO_2$ onto the mesh/PDMS and exposing the silicone target substrate (Ecoflex 0030, Smooth-On, Inc.) to UV-ozone (to creating reactive —OH groups the surface) enables bonding between the two upon physical contact [21]. (Low pressures avoid contact between the PDMS and the finger-tube, thereby allowing bonding only to the mesh.) Removal of the stamp completes the transfer process, as shown in FIG. 1c.

The electrotactile electrodes use 600 nm thick layers of Au in a concentric design, consisting of an inner disk (400 µm radius) surrounded by an outer ring (1000 µm radius) with a 250 µm wide gap between the two. Interconnects consist of 100 µm wide traces of Au in serpentine geometries (radii of curvature ~800 µm); these traces connect the electrotactile electrodes to Si NM diodes (lateral dimensions of 225 µm×100 µm and thicknesses of 300 nm). Two layers of Au interconnects (200 nm and 600 nm thick), isolated by a 1.25 µm PI layer and connected through etched PI vias, establish a compact wiring scheme with overlying interconnects. The 600 nm thick Au interconnect layer allowed robust electronic contact though the PI vias. The strain gauge arrays consist of four Si NMs (strips with lateral dimensions of 1 mm×50 µm and thicknesses of 300 nm) electrically connected by 200 nm thick, 60 µm wide Au traces patterned in serpentine shapes (radii of curvature ~400 µm). The tactile sensors use 200 nm thick Au electrodes and interconnects in the geometry of the electrotactile arrays but with the concentric electrode pairs replaced by single, disc-shaped electrodes (radii ~1000 µm).

Figure 2:
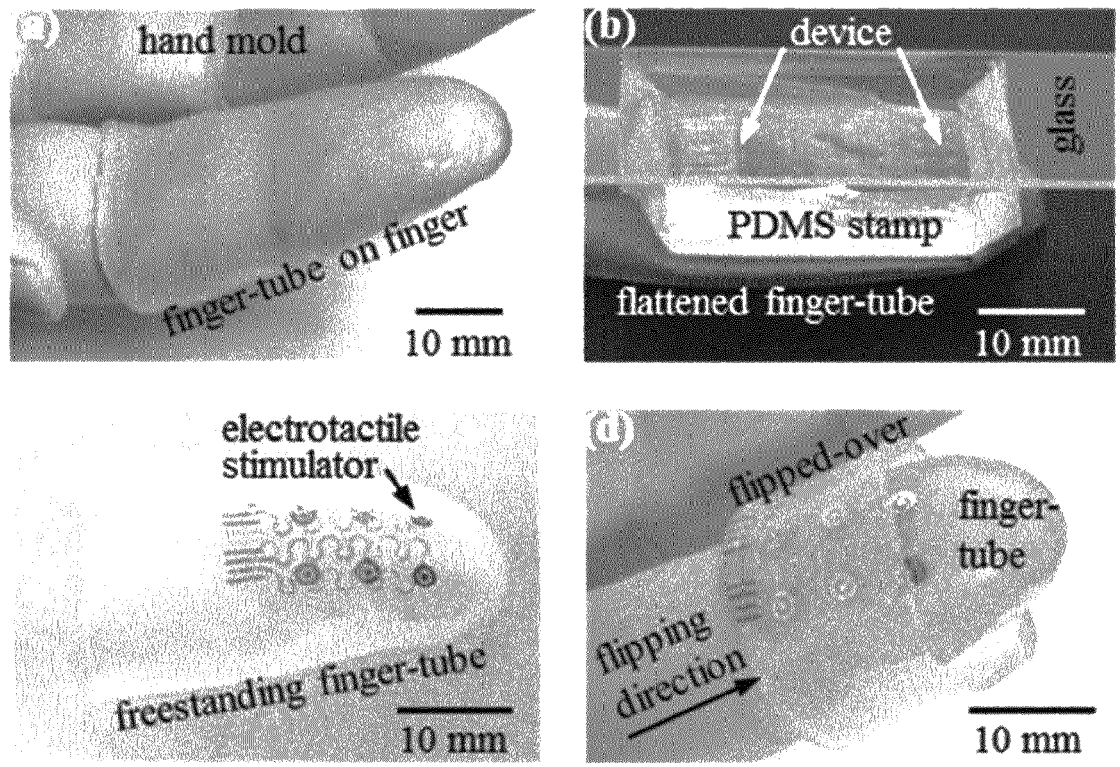
FIG. 2. Process for fabricating a multiplexed array of electrotactile stimulators in a stretchable, mesh geometry on the inner surface of an elastomeric finger-tube. (a) casting and curing an elastomer precursor on the finger of a model hand yields a thin (~500 μm thick), closed-form membrane, i.e. a finger-tube; (b) a PDMS stamp (here, backed by a glass microscope slide) delivers the electrotactile device to the outer surface of this finger-tube, while compressed into a flattened geometry; (c) electrotactile array on the outside of the freestanding finger-tube; (d) turning or flipping the tube inside out relocates the array on the inner surface of the finger-tube, shown here at the midway point of this flipping process, so that the previous outer surface is the inner surface and the previous inner surface is the outer surface.

The Ecoflex substrates, which we refer to as finger-tubes, adopt three dimensional forms specifically matched to those of fingers on a plastic model of the hand. The fabrication involves pouring a polymer precursor to Ecoflex onto a finger of the model and curing at room temperature for 1 hour, to create a conformal sheet with ~125 µm thickness. Pouring a second coating of precursor onto this sheet and curing for an additional 1 hour doubles the thickness; repeating this process 4 times results in a thickness of ~500 µm. Removing the Ecoflex from the model and completing the cure by heating at 70° C. for 2 hours forms a free standing structure, i.e. a finger-tube, like the one illustrated in FIG. 2. Ecoflex is an attractive material for this purpose because it has a low modulus (~60 kPa) and large fracture strain (~900%). The former allows soft, intimate contact with the skin; the latter enables the 'flipping-over' process referred to previously, and described in quantitative detail in a following section. Transfer printing delivers the device mesh structure to the outer surface of the finger-tube, while pressed into a flattened geometry (FIG. 2b). The entire integrated system is then flipped inside-out, to move the mesh from the outer to the inner surface of the tube, as shown in FIG. 2c,d. Multifunctional devices incorporate electrotactile stimulators on the inside, and strain gauge arrays and tactile sensors on the outside.

Figure 3:
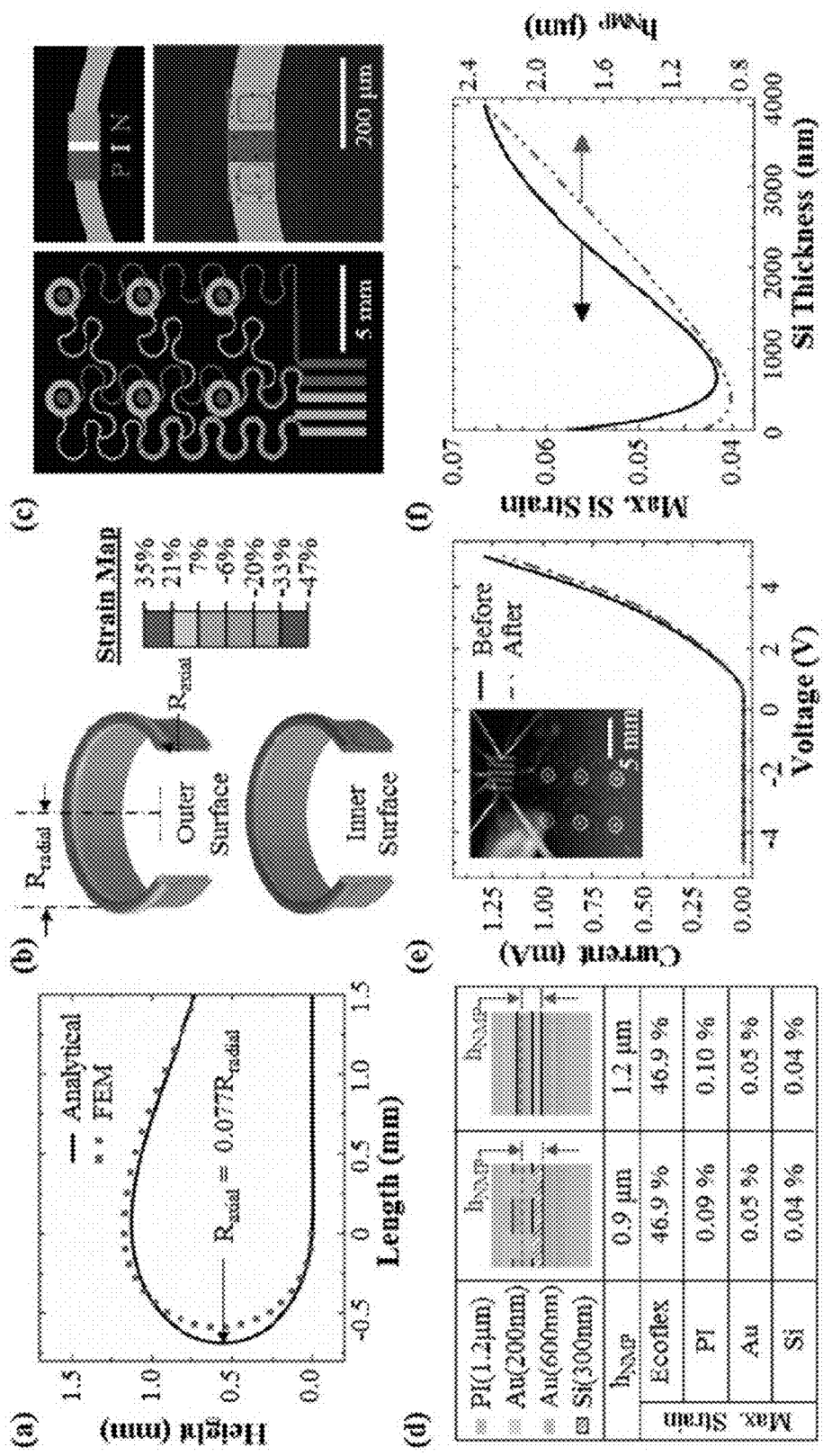
FIG. 3. Mechanics modeling of the "flipping-over" process and application to arrays of electrotactile stimulators multiplexed with Si NM diodes. (a) Calculated (analytical and FEM) profiles of an Ecoflex finger-tube during bending associated with flipping the tube inside out, showing a linear relationship between the radius ($R_{radial}$=7.5 mm) of the tube and the minimum bending radius ($R_{axial}$). (b) FEM results for maximum strains on the inner and outer surfaces during this process; (c) schematic illustration of a multiplexed electrotactile array with serpentine mesh interconnects, with magnified diagram (right top) and image (right bottom) of a PIN Si NM diode (after flipping-over); (d) schematic cross sectional illustrations of two regions of the device, with the position of the NMP indicated with a dashed red line, and analytical results for the maximum strains during the flipping-over process; (e) I-V characteristics of a Si NM diode before and after flipping-over; (f) maximum strain in the Si NM diode and $h_{NMP}$ (the offset between the neutral mechanical plane and the lower surface of the Si NM) as a function of thickness of the Si NM.

Device designs described previously have the advantage that they are conformal to the finger, in a way that naturally presses the electronics on the interior surface of the finger-tube (in this case the electrotactile stimulating electrodes) into intimate contact with the skin. The flipping-over process represents a critical step, enabled by careful design of the mechanics in the device mesh. Quantitative mechanics modeling provides important insights. The finger-tube can be approximated as a self-equilibrated, axisymmetric tube with two dimensional symmetry. Energy minimization using linear elastic shell theory determines the resulting shapes. FIG. 3a shows analytical and FEM results for an Ecoflex cylinder with radius ($R_{radial}$) of 7.5 mm and thickness of 500 μm when bent back on itself, at a mid-way point during the flipping-over process. The minimum axial radius of curvature ($R_{axial}$) of 596 μm, as indicated in FIG. 3a, defines the location of maximum induced strain as the tube is flipped over. The maximum strains on the inner and outer surfaces in this configuration, as shown in the color map of FIG. 3b, are ~30-40% (see supplementary file at stacks.iop.org/Nano). The device mesh structures must, therefore, be able to accommodate strains in this range. This requirement is non-trivial for systems like the ones described here, due to their incorporation of brittle materials such as silicon (fracture strain ~1%).

Circuit layouts, guided by theory, can be identified to satisfy these requirements. As an example, FIG. 3c provides a diagram of a multiplexed electrotactile array in a mesh configuration with narrow, serpentine interconnects. The orange and blue regions correspond to Au layers separated by layers of PI, respectively; the red regions indicate Si NM (300 nm thick) diodes in a PIN (p-doped/intrinsic/n-doped) configuration. The short dimensions of the diodes lie parallel to the flipping-over direction, to minimize strains in the Si during this process. These optimizations lead to maximum calculated strains that are only 0.051%, 0.10%, and 0.040% for the Au, PI, and the Si, respectively (see FIG. 3d). The computed position of the NMP also appears in FIG. 3d. Since the moduli of the device layers are several orders of magnitude larger than that of Ecoflex, the location of the NMP plane is largely independent of the Ecoflex. Appropriate selection of the thicknesses of the PI layers allows the NMP to be positioned at the location of the Si NMs, thereby minimizing the induced strains in this brittle material [21, 22]. The thicknesses of the Si NM diodes influences the maximum strains that they experience, as shown in analytical calculations of FIG. 3f. A minimum occurs at the thickness that places the NMP at the shortest distance from the Si NM diode (i.e. $h_{NMP}$). The position of this minimum can also be adjusted by changing the thicknesses of the PI layers, for example. Further reductions in strain can be realized by reducing the lengths of the devices. Implementing designs that incorporate these considerations and exploiting interconnects with optimized serpentine layouts ensures robust device behavior throughout the fabrication sequence. For example, FIG. 3e shows negligible change in the I-V characteristics (Agilent 4155C semiconductor parameter analyzer) of a Si NM diode before and after the flipping-over process.

Figure 4:
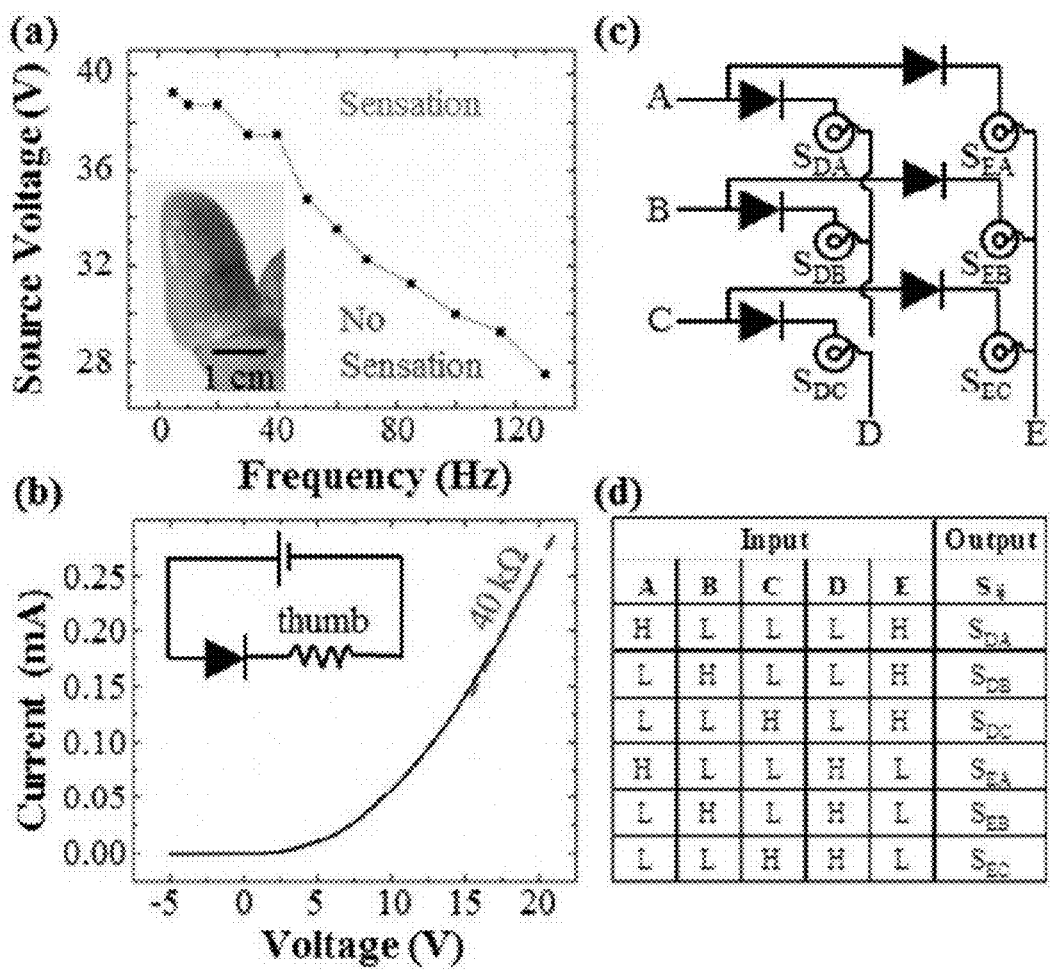
FIG. 4. Mechanics and electrical characteristics of a 2×3, multiplexed electrotactile array on a fingertube. (a) Voltage required for electrotactile sensation as a function of stimulation frequency. Inset: electrotactile array on human finger during experiments; (b) I-V characteristics of multiplexed electrotactile electrodes in contact with a human thumb; (c) circuit diagram of the diode multiplexing scheme; (d) function table showing inputs for addressing each of the six channels (H=High; L=Low).

Experimental results demonstrate expected functionality in the electrotactile arrays. FIG. 4a shows the perception of touch on a dry human thumb as a function of voltage and frequency, applied between the inner dot and outer ring electrodes (FIG. 3d). Stimulation used a monophasic, square-wave with 20% duty cycle, generated using a custom setup. The inset provides an image of a device, with connection to external drive electronics via a flexible anisotropic conductive film (ACF). The required voltage for sensation decreases with increasing frequency, consistent with equivalent circuit models of skin impedance that involve resistors and capacitors connected in parallel. The absolute magnitudes of these voltages depend strongly on the skin hydration level, electrode design, and stimulation waveform [23]. FIG. 4b shows I-V characteristics of an electrotactile electrode pair while in contact with a hydrated human thumb, measured through a multiplexing diode. At high positive voltages, the resistance of the diode is negligible compared to the skin; here, the slope of the I-V characteristics yield an estimate of the resistance of the skin-electrode contact plus the skin. The value (~40 kΩ) is in a range consistent with measurements using conventional devices [24,25]. The diode is stable to at least 20 V, corresponding to currents of 0.25 mA, which is sufficient for electrotactile stimulation on the skin and tongue [2, 6, 7].

These diodes enable multiplexed addressing, according to an approach that appears schematically in FIG. 4c. Each unit cell consists of one diode and one electrotactile electrode pair. FIG. 4d presents a table of the inputs required to address each of the six electrotactile channels. For example, channel $S_{DA}$ can be activating by applying a high potential (+5 V) to inputs A and E and a low potential (0 V) to inputs B, C, and D, thereby yielding a +5 V bias across the outer ring (+5 V) and inner ring electrode (0 V) of this channel. This configuration forward biases the Si NM diode, which results in stimulation current, as shown in FIG. 4b. At the same time, channels $S_{EB}$ and $S_{EC}$ experience a bias of −5 V across the electrodes but in these cases the Si NM diodes are reverse biased, thus preventing stimulating current. Channels $S_{DB}$, $S_{DC}$, and $S_{EA}$ have the same potential on the inner and outer electrodes, resulting in zero bias. Electrical isolation of adjacent channels is a consequence of inner to outer electrode separations (250 μm) that are small compared to the distances between channels (6000 μm). Advanced multiplexing schemes that use several diodes per stimulation channel, or active transistors, are compatible with the fabrication process and design principles outlined here.

Figure 5:
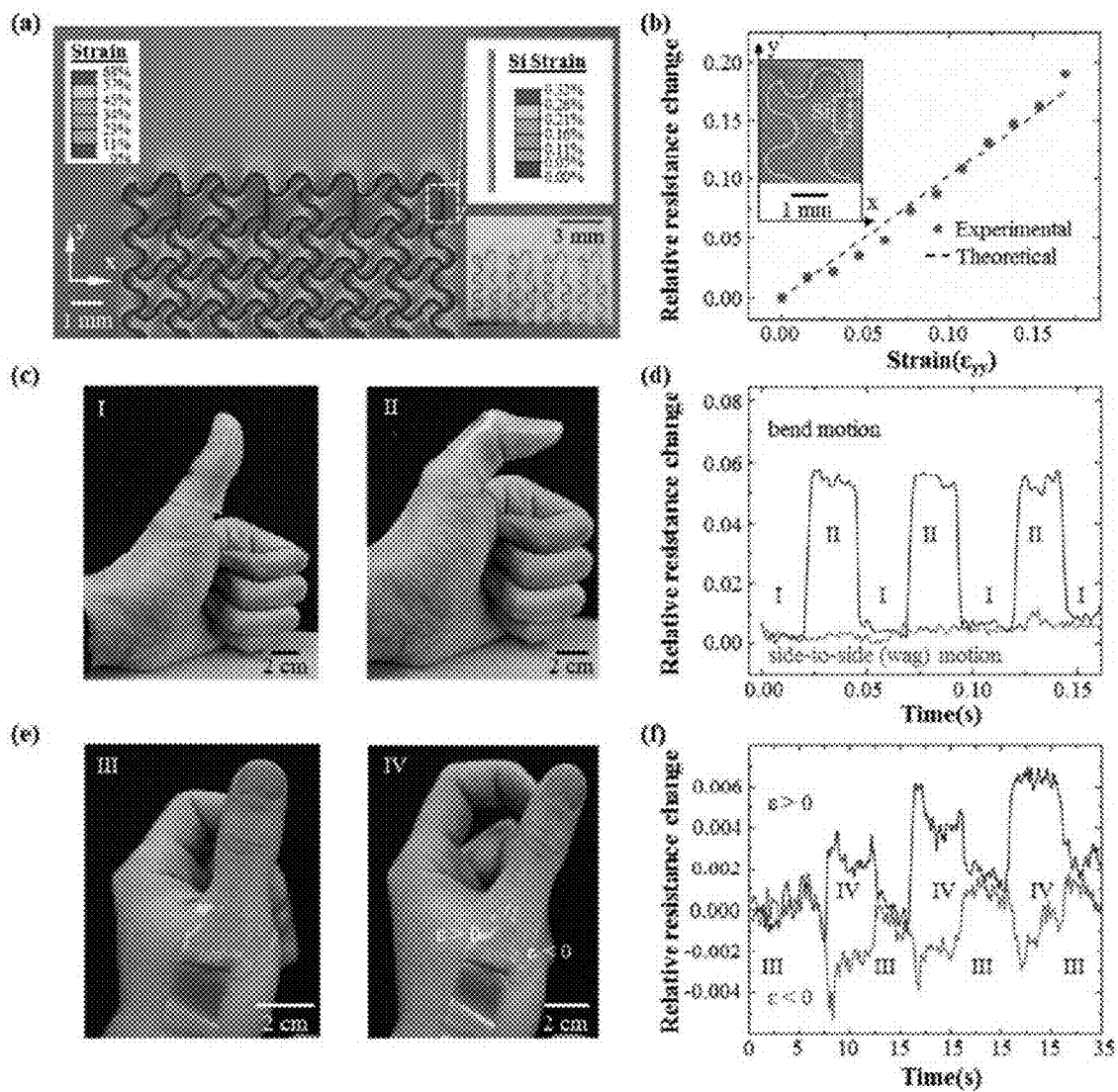
FIG. 5. Detection of finger motion with arrays of stretchable Si NM strain gauges. (a) FEM results of the maximum principle strain for a 1×4 array of gauges (straight, vertical structures near the top of the serpentine interconnect mesh) due to an overall 10% strain applied along the longitudinal (y) direction. The upper inset shows the strains in the gauge highlighted by the yellow dashed box. The lower inset provides an image of a fabricated device with a layout that matches that of the FEM results; (b) experimentally measured and analytically calculated changes in resistance for a representative Si NM strain gauge as a function of applied strain along the longitudinal direction. The inset provides an SEM image of a portion of the device, with the Si NM gauge located in the dashed box; (c) images of a strain gauge array on a finger-tube mounted on the thumb, in straight (I) and bent (II) positions; (d) change in resistance of a representative gauge during three bending cycles (black) and side-to-side motion (red); (e) images of a strain gauge array on a thin, elastomeric sheet laminated onto the metacarpal region of the thumb in straight (III) and sideways deflected (IV) positions; (f) change in resistance of gauges at two ends of the array during three cycles of side-to-side motion.

FIG. 5 shows a set of straight, uniformly doped Si NMs as strain gauges addressed with interconnects in a mesh geometry. FEM calculations summarized in FIG. 5 reveal strain profiles in a 1×4 array of gauges (vertical strips; yellow dashed box and upper inset highlights an individual device) on Ecoflex, under a uniaxial in-plane strain of 10%. These results show that the overall strain is mostly accommodated by changes in the shapes of the serpentine interconnects and, of course, the Ecoflex itself. The Si NM gauges experience strains (~$10^{-3}$) that are ten times lower than the applied strain, as shown in the inset in FIG. 5a.

The ability to use Si NMs as high performance strain gauges in stretchable forms results from the strong piezoresistance properties of Si, combined with serpentine layouts. These characteristics, taken together, determine the fractional change in resistance per applied strain. The associated effective gauge factor ($GF_{eff}$) can be related to the intrinsic gauge factor of a silicon gauge, $GF_{Si}=\Delta R/(R \in_{Si})$ where $\Delta R$ is the change in resistance, R is the initial resistance, and $\in_{Si}$ is the strain in the silicon, by the following expression $GF_{eff}=GF_{Si}/(\in_{Si}/\in_{app})$ where $\in_{app}$ is the strain applied to the overall, integrated system. The designs reported here yield values of $\in_{Si}/\in_{app}$ that are much smaller than one, specifically to avoid fracture-inducing strains in the Si during fabrication, mounting and use over physiologically relevant ranges of strain. FIG. 5b shows experimentally measured values of $\Delta R$ (evaluation at 1 V, using an Agilent 4155C semiconductor parameter analyzer) as a function of $\in_{app}$, which corresponds to $GF_{eff}$~1. By fitting the experimental and FEM results to FIG. 5b, the $GF_{Si}$ is ~95, consistent with a recent report on Si NM strain gauges, with otherwise similar designs, on flexible sheets of plastic [26]. We emphasize that device design parameters, such as the size of the gauge and the dimensions of the serpentine interconnects, enable engineering control over $GF_{eff}$, from values as large as $GF_{Si}$ to those that are much smaller, with a correspondingly increased range of strains over which measurements are possible.

FIG. 5c shows a strain gauge array on a finger-tube located near the knuckle region of the thumb, in straight (I) and bent (II) positions. Upon bending, the gauges experience tensile strain, resulting in an increase in resistance, as shown for three bending cycles in FIG. 5d. The relative resistance changes suggest that the strain associated with bending reaches ~6%. As expected, side-to-side motions induced no changes. FIG. 5e shows a similar array on a thin sheet of Ecoflex, mounted near the metacarpal region of the thumb. Here, the device adheres to the skin by van der Waals interactions, similar to mechanisms observed in epidermal electronic systems [13]. The images in FIG. 5e correspond to the thumb in straight (III) and sideways deflected (VI) positions. The changes in resistance for the two gauges on opposite ends of the 1×4 array for three side-to-side cycles of motion appear in FIG. 5f. For each cycle, the change in resistance of the rightmost gauge indicates compressive strain; the leftmost indicates corresponding tensile strain. The results suggest that arrays of gauges can be used to identify not only the magnitude but also the type of motion.

Figure 6:
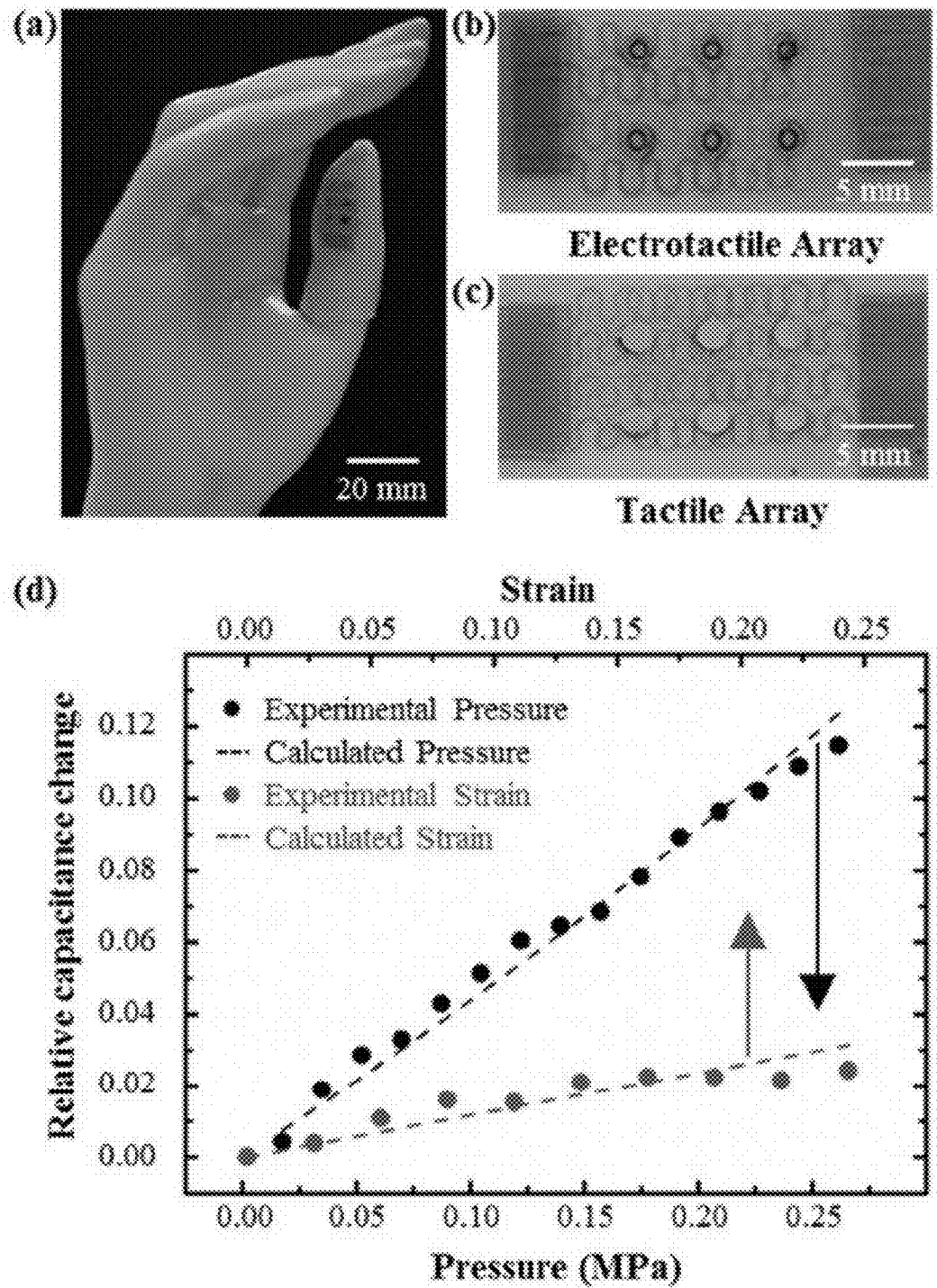
FIG. 6. Tactile sensing with integrated capacitance sensors. (a) sensors on the anterior of the thumb; (b) inner electrodes for a 2×3 array of sensors (electrotactile electrodes); (c) outer electrodes for the same array; (d) measured and analytically calculated change in capacitance of a single sensor with applied pressure and tensile strain.
Figure 7:
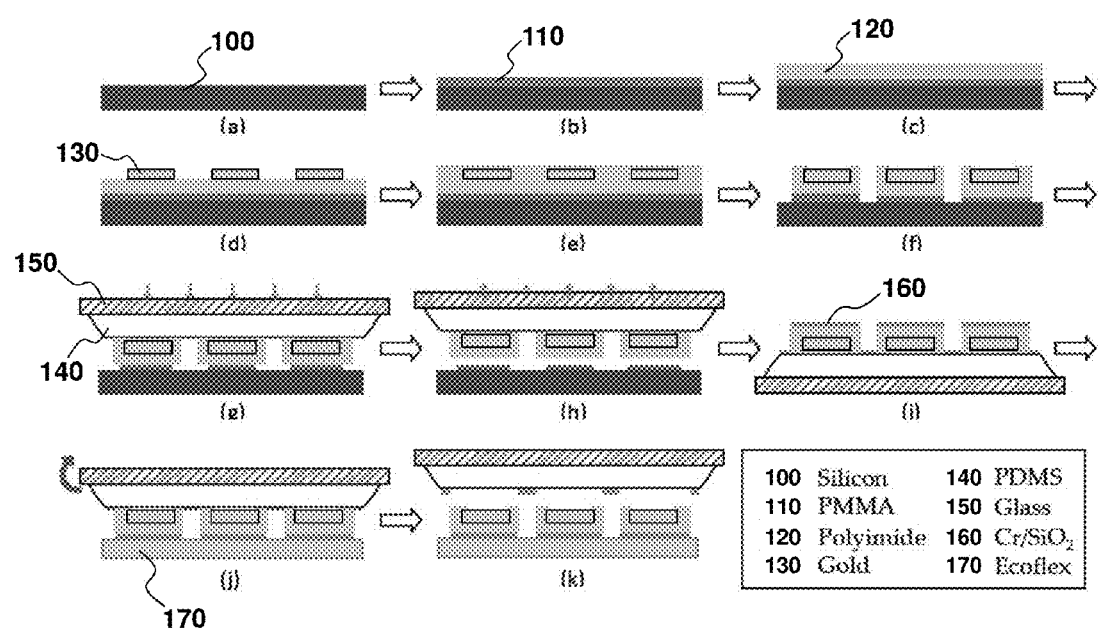
FIG. 7. Schematic of the basic fabrication process. (a) Si substrate; (b) spin coat sacrificial PMMA; (c) spin coat polyimide (PI) precursor/250° C. bake in inert atmosphere; (d) Au evaporation/patterning; (e) spin coat PI precursor/250° C. bake in inert atmosphere; (f) $O_2$ RIE to expose Au electrodes and form PI mesh structure; (g) PMMA undercut in acetone/application of PDMS stamp; (h) devices transferred to PDMS stamp; (i) Cr/SiO$_2$ evaporated onto back of device; (j) PDMS stamp pressed onto UV exposed Ecoflex; (k) transfer completed with PDMS stamp removal.

As a final demonstration, we built a type of tactile (pressure) sensor suitable for integration on the finger-tube platform. The devices exploit changes in capacitance associated with opposing electrodes on the inner and outer surfaces of the Ecoflex. Applied pressure decreases the thickness of the Ecoflex, thereby increasing the capacitance of this structure. Here, layouts like those for the electrotactile devices serve as inner electrodes; a mirror image of this array mounted in an aligned configuration on the outer surface defines a collection of parallel plate capacitors with the Ecoflex as the dielectric. An array of such devices on the anterior surface of a model of the hand appears in FIG. 6a. FIGS. 6b and 6c show images of the inner and outer electrode arrays. The relative change in capacitance with applied pressure for a representative device appears in FIG. 6d (black symbols). Here, capacitance was measured (Agilent E4980A LCR meter) as a function of pressure applied with a series of weights mounted on a platform with a constant contact area, taking care to minimize effects of parasitic capacitances and to eliminate ground loops. Approximately linear behavior is observed over the range studied, consistent with simple mechanical models, $\Delta C/C_o = P/(\overline{E}_{Ecoflex} - P)$, where $\Delta C$ is the capacitance change, $C_o$ is the initial capacitance, P is the applied pressure, and $\overline{E}_{Ecoflex}$ is the effective Ecoflex modulus. This simple model assumes no electrostriction or strain induced changes in dielectric force (FIG. 6d, black line). Due to the Poisson effect, the devices also respond to in-plane strains ($\in_{applied}$), as shown in FIG. 6d (red), consistent with the simple model $\Delta C/C_o = [(EA)_{system}/(EA)_{electrodes}] v \in_{applied}$, where the Poisson's ratio (v) is 0.496, and $(EA)_{system}$ and $(EA)_{electrodes}$ are the tensile stiffness of the system and electrodes respectively. This type of technology provides a simple alternative to recently reported devices that offer similar functionality, but on flexible substrates, and based on conductive elastomers, elastomeric dielectrics, or compressible gate dielectrics in organic transistors. [14, 16, 18, 27, 28].

The results presented here establish some procedures and design rules for electronics and sensors that can be mounted conformally onto the fingers. Other appendages of the body can be addressed in similar manner. Furthermore, most of the considerations in mechanics and fabrication are agnostic to the specific device functionality or mounting locations. As a result, many of these concepts can be applied generally, to other types of systems and modes of use. Future challenges include the development of capabilities for wireless power supply and data transfer.

Example 2

Methods of Making the Electronic Devices

1. Electrotactile Arrays:
a. Cut 1'×1' SOI wafers ((110), 300 nm Si) and clean with acetone and IPA.
b. Form a 900 nm layer of $SiO_2$ by PECVD as p-dope diffusion mask.
c. Pattern diffusion mask by: i. Pattern photoresist (PR) AZ5214: Spin coat PR AZ5214 (3000 rpm, 30 s), pre-bake (110° C., 1 min), align mask and expose, develop with MIF327 (40 s), post-bake (110° C., 3 min). ii. Wet etch with buffered oxide etchant (BOE) (NH4F: HF=6:1) for 1.5 min and remove PR with acetone.
d. P-type doping: i. Clean wafers with Nano-strip™ (Cyantek), place next to boron doping source, and put into furnace (1000° C.) for 30 min. ii. Etch $SiO_2$ mask completely with HF (30 sec), and form another 900 nm layer of $SiO_2$ by PECVD as n-dope diffusion mask. iii. Pattern diffusion mask: Same as 1c.
e. N-type doping: i. Clean wafers with Nano-Strip™, place next to phosphorous doping source at 1000° C. for 10 min. ii. Etch $SiO_2$ mask completely with HF (30 sec).
f. Create holes (3 µm dia., spacing 30 µm) for releasing Si film: i. Spin coat PR Shipley S1805 (3000 rpm, 30 s), pre-bake (110° C., 1 min), align mask and expose, develop with MIF327 (9 s), post-bake (110° C., 3 min). ii. Etch Si with RIE (50 mtorr, 40 sccm SF6, 100 W, 1 min).
g. Undercut oxide layer of SOI: i. Immerse wafers in HF solution for 15~20 min until the Si layer is detached from the substrate.
h. Pick up the Si film from the SOI wafer with a PDMS stamp.
i. Prepare target Si wafer: i. Spin coat Si wafer with polymethylmethacrylate (PMMA, 3000 rpm, 30 s, ~100 nm), cure at 180° C. for 1.5 min. ii. Spin coat polyimide precursor (4000 rpm, 30 s) and partially cure at 150° C. for 40 sec.
j. Transfer Si to target Si wafer: i. Press the stamp into contact with the target wafer and apply force with hands for 10 s. ii. Put stamp and target wafer on a hotplate at 110° C. and slowly release the stamp when thermal expansion of the stamp is observed. iii. Put target wafer (now with Si film) on hotplate at 150° C. for another 5 min and remove PR with acetone (2 s). iv. Bake in an inert atmosphere at 250° C. for 1 hr.

k. Si diode isolation: i. Pattern PR AZ5214. ii. Etch exposed Si with RIE (50 mtorr, 40 sccm SF6, 100 W, 1 min) and strip PR with acetone.

l. 1st Au interconnect layer: i. Deposit Cr (5 nm)/Au (200 nm) with electron beam evaporator. ii. Pattern PR AZ5214. iii. Wet etch Au and Cr. iv. Strip PR with acetone.

m. PI insulation layer with vias: i. Spin coat polyimide precursor (4000 rpm, 30 s). ii. Prebake on hotplate (150° C., 5 min). iii. Bake in an inert atmosphere at 250° C. for 1 hr. iv. Spin coat PI with PR AZ4620 (3000 rpm, 30 s), pre-bake (110° C., 1 min), align via mask and expose, develop with 3:1 diluted MIF400 (40 s). v. Etch exposed polyimide with RIE (100 W, 150 mTorr, 20 sccm $O_2$, 20 min). vi. Strip PR with acetone.

n. 2nd Au interconnect layer: i. Deposit Cr (10 nm)/Au (600 nm) with electron beam evaporator. ii. Pattern PR AZ5214. iii. Wet etch Au and Cr. iv. Strip PR with acetone.

o. Final PI encapsulation and etch: i. Form PI layer: Same as 1n. ii. Pattern PR AZ4620. iii. Etch exposed polyimide with RIE (100 W, 150 mTorr, 20 sccm $O_2$, 50 min) to form PI mesh structure. iv. Strip PR with acetone.

p. Transfer printing: i. Immerse device in heated acetone bath (100° C.) to undercut PMMA. ii. Press PDMS stamp into contact with the device and quickly remove to transfer device onto the stamp. iii. Deposit Cr (5 nm)/SiO2 (20 nm) with e-beam evaporator. iv. Ultra-violet/ozone (UV-0) treat the target substrate (Ecoflex finger tube) for 4 min. v. Press the PDMS stamp onto Ecoflex and remove stamp slowly.

2. Strain Gauge Arrays:

a. Cut 1'×1' (110) SOI wafers (300 nm Si) and clean with acetone and IPA.

b. P-type doping: same as 1d with a 4 min doping time.

c. Transfer print Si to target wafer: same as 1f-j.

d. Si strain gauge isolation: same as 1k.

e. Au interconnect layer: same as 1l.

f. Final encapsulation: same as 1o with 30 min $O_2$ RIE.

g. Transfer printing: same as 1p.

3. Contact Sensor Array:

a. Cut 1'×1' Si wafers and clean with acetone and IPA.

b. Spin coat PMMA (3000 rpm, 30 s) as sacrificial layer.

c. Form polyimide layer as substrate: Same as 1m.

d. Au interconnect layer: same as 1l.

e. Final encapsulation: same as 2f.

f. Transfer printing to overlay with electrotactile electrodes: same as 1p.

Summaries of various methods for making sensors and actuators useful in the devices and methods provided herein are summarized in FIGS. 10-13.

Figure 8:
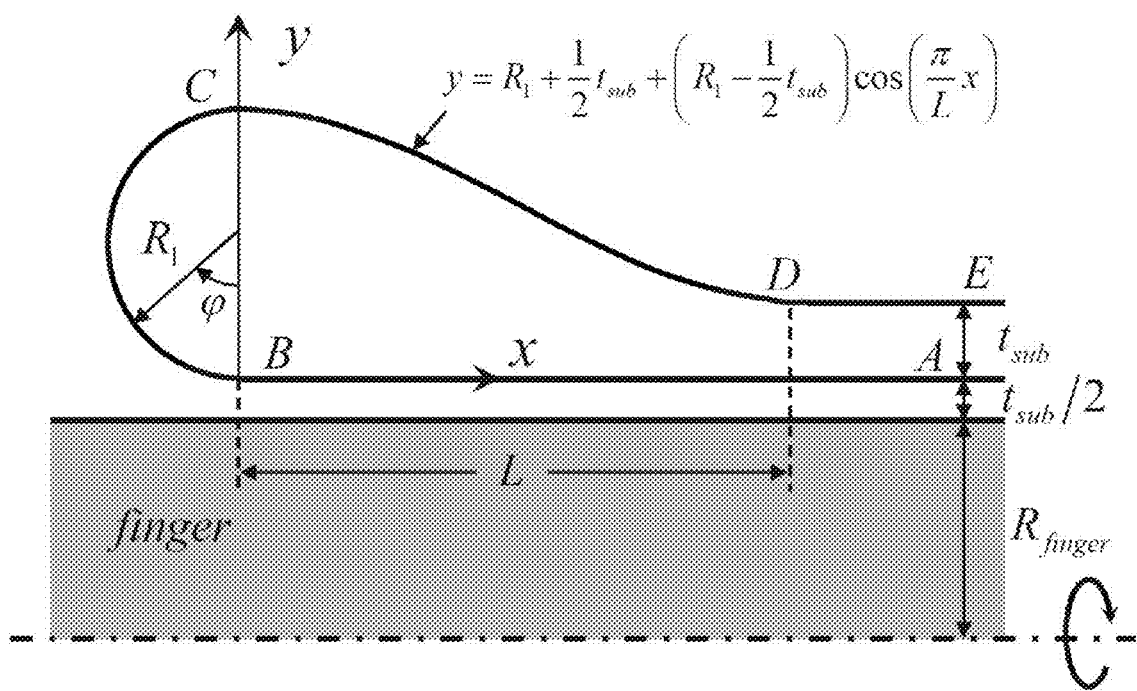
FIG. 8. Schematic illustration of the flipped-over elastomeric Ecoflex tube in the plastic hand model.

Mechanics Modeling:

Strain of the multiplexed electrotactile arrays during the flipping-over process. The elastomeric Ecoflex finger-tube with the thickness $t_{sub}$ is flipped over twice on the finger model with the radius $R_{finger}$. FIG. 8 illustrates a self-equilibrated, axisymmetric Ecoflex tube during the flipping-over process; AB represents the cylindrical portion in contact with the surface of plastic hand; the outer surface DE is also cylindrical; transition between the two can be approximated by a semi-circle BC (with radius $R_1$ to be determined in FIG. 8) and a sinusoidal curve CD (with half wavelength L to be determined). For the profile shown in FIG. 8, the linear elastic shell theory gives the bending energy and the membrane energy. Minimization of the total energy then gives $R_1$ and L. For $R_{finger}$=7.5 mm and $t_{sub}$=500 μm, energy minimization gives the bending radius $R_1$=596 μm and L=2.47 mm for the Poisson's ratio of Ecoflex v=0.496. The maximum tensile and compressive strains in Ecoflex are $\in_{tensile}$=34.4% and $\in_{compressive}$=−49.5%, which agree well with the FEM results ($\in_{tensile}$=35.1% and $\in_{compressive}$=−46.9%).

The multiplexed electrotactile arrays are modeled as a composite beam with multiple layers. The bending moment and membrane force obtained from the above analytical model are imposed on the multiplexed electrotactile arrays. This gives the analytical expressions of the maximum strain in Si and Au, which are validated by FEM for relatively long Si diodes. For relatively short Si diodes, the analytical expressions overestimate the maximum strain in Si and Au.

Mechanical analysis of the tactile (pressure) sensor: The inner dot and outer ring electrodes form pairs of parallel capacitors. The capacitance change is related to the applied pressure that results in the decrease of the thickness of Ecoflex dielectric $$\frac{\Delta C}{C_0} = \frac{P}{\overline{E}_{ecoflex} - P}, \quad (S1)$$

where:

$$\overline{E}_{ecoflex} = (1-v)E/[(1+v)(1-2v)]$$

is the effective modulus of Ecoflex dielectric under uniaxial stretching, and E=60 kPa is the Young's modulus of Ecoflex. As shown in FIG. 6d, Eq. (S1) agrees well with experiments.

For an applied tensile strain $\in_{applied}$, the strain in the Ecoflex dielectric between electrodes is related to the tensile stiffness $(EA)_{system}$ of the system and tensile stiffness $(EA)_{electrodes}$ of the electrodes by $\in_{applied}(EA)_{system}$ $(EA)_{electrodes}$. The capacitance change of a single element of the pressure sensor array is also determined by the decrease of the thickness of the Ecoflex dielectric, and is given by $$\frac{\Delta C}{C_0} = \frac{(EA)_{system}}{(EA)_{electrodes}} v\varepsilon_{applied}. \quad (S2)$$

REFERENCES FOR EXAMPLES 1-2

1. Barfield W, Hendrix C, Bjorneseth O, Kaczmarek K A and Lotens W 1995 *Presence-Teleoperators and Virtual Environments* 4 329
2. Matteau I, Kupers R, Ricciardi E, Pietrini P and Ptito M 2010 *Brain Research Bulletin* 82 264
3. Tan H Z, Durlach N I, Reed C M and Rabinowitz W M 1999 *Perception & Psychophysics* 61 993
4. Sparks D W, Kuhl P K, Edmonds A E and Gray G P 1978 *Journal of the Acoustical Society of America* 63 246
5. Danilov Y P, Tyler M E and Kaczmarek K A 2008 *International Journal of Psychophysiology* 69 162
6. Kaczmarek K A, Webster J G, Bachyrita P and Tompkins W J 1991 *Ieee Transactions on Biomedical Engineering* 38 1
7. Lozano C A, Kaczmarek K A and Santello M 2009 *Somatosens. Mot. Res.* 26 50
8. Warren J P, Bobich L R, Santello M, Sweeney J D and Tillery S I H 2008 *Ieee Transactions on Neural Systems and Rehabilitation Engineering* 16 410

9. Bach-y-Rita P, Tyler M E and Kaczmarek K A 2003 *International Journal of Human-Computer Interaction* 15 285
10. Jones L A and Safter N B 2008 *Human Factors* 50 90
11. Vuillerme N, Pinsault N, Chenu O, Demongeot J, Payan Y and Danilov Y 2008 *Neuroscience Letters* 431 206
12. Vidal-Verdu F and Hafez M 2007 *Ieee Transactions on Neural Systems and Rehabilitation Engineering* 15 119
13. Kim D H et al., 2011 *Science* 333 838
14. Lipomi D J, Vosgueritchian M, Tee B C, Hellstrom S L, Lee J A, Fox C H and Bao Z 2011 *Nature Nanotech.* 6 788
15. Rogers J A and Huang Y G 2009 *Proc. Natl. Acad. Sci. U.S.A.* 106 16889
16. Someya T, Sekitani T, Iba S, Kato Y, Kawaguchi H and Sakurai T 2004 *Proc. Natl. Acad. Sci. U.S.A.* 101 9966
17. Rogers J A, Lagally M G and Nuzzo R G 2011 *Nature* 477 45
18. Kim D H et al., 2011 *Nat. Mater.* 10 316
19. Meitl M A et al. 2006 *Nat. Mater.* 5 33
20. Yu J and Bulovic V 2007 *Appl. Phys. Lett.* 91
21. Kim D H et al. 2008 *Science* 320 507
22. Rogers J A, Someya T and Huang Y G 2010 *Science* 327 1603
23. Kaczmarek K A and Haase S J 2003 *Ieee Transactions on Neural Systems and Rehabilitation Engineering* 11 9
24. Woo E J, Hua P, Webster J G, Tompkins W J and Pallasareny R 1992 *Medical & Biological Engineering & Computing* 30 97
25. Hua P, Woo E J, Webster J G and Tompkins W J 1993 *Ieee Transactions on Biomedical Engineering* 40 335
26. Won S M et al. 2011 *Ieee Transactions on Electron Devices* 58 4074
27. Someya T et al. 2005 *Proc. Natl. Acad. Sci. U.S.A.* 102 12321
28. Takei K et al. 2010 *Nat. Mater.* 9 821

Example 3

Appendage Mountable Electronic Devices Conformable to Biological Surfaces

Figure 14:
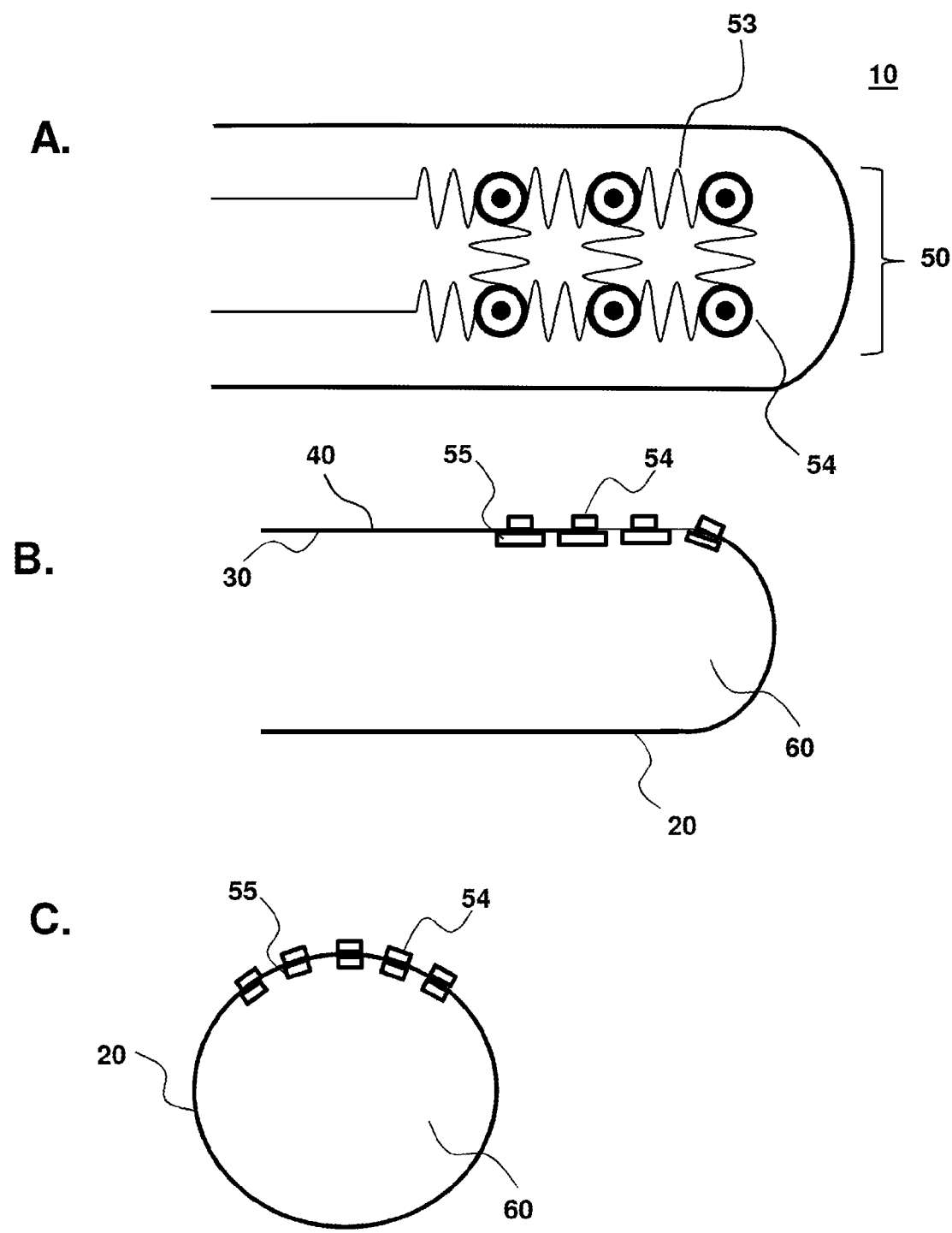
FIG. 14(A-C) provides different views of an appendage mountable electronic system of the invention.

One example of an appendage mountable electronic system is schematically summarized in FIGS. 14-17, including an appendage corresponding to a finger or a finger-tip. Different views of an appendage mountable electronic system 10 is provided in FIG. 14(A-C), with a top view (A), a side cross-section view (B) and a cross-section viewed from an end (C). Referring to the different views of FIG. 14, the system 10 comprises a flexible and stretchable substrate 20 having an inner surface 30 and an outer surface 40. In this example, the electronic device 50 comprises a plurality of flexible or stretchable sensors 54 supported by the outer surface 40, and a plurality of flexible or stretchable actuators 55 supported by the inner surface 30. The electronic device further comprises various components to provide desired functionality and operating characteristics. For example, FIG. 14 illustrates electrical interconnects 53 in a curved or serpentine configuration that electrically interconnect more rigid components (e.g., rigid device islands), such as electrodes 54 having an interior disk-shaped electrode positioned within and concentric to a ring-shaped electrode. The cross-sectional views provided in FIGS. 14B and 14C illustrate that electronic device 50 may be supported by the inner surface 30, the outer surface 40, or by both surfaces. Optionally, the electronic device may comprise an array of sensors 54, such as tactile sensors, supported by the outer surface and an array of stimulators 55, such as electrotactile stimulators, supported by the inner surface 30, for interfacing with a surface of an appendage.

Figure 15:
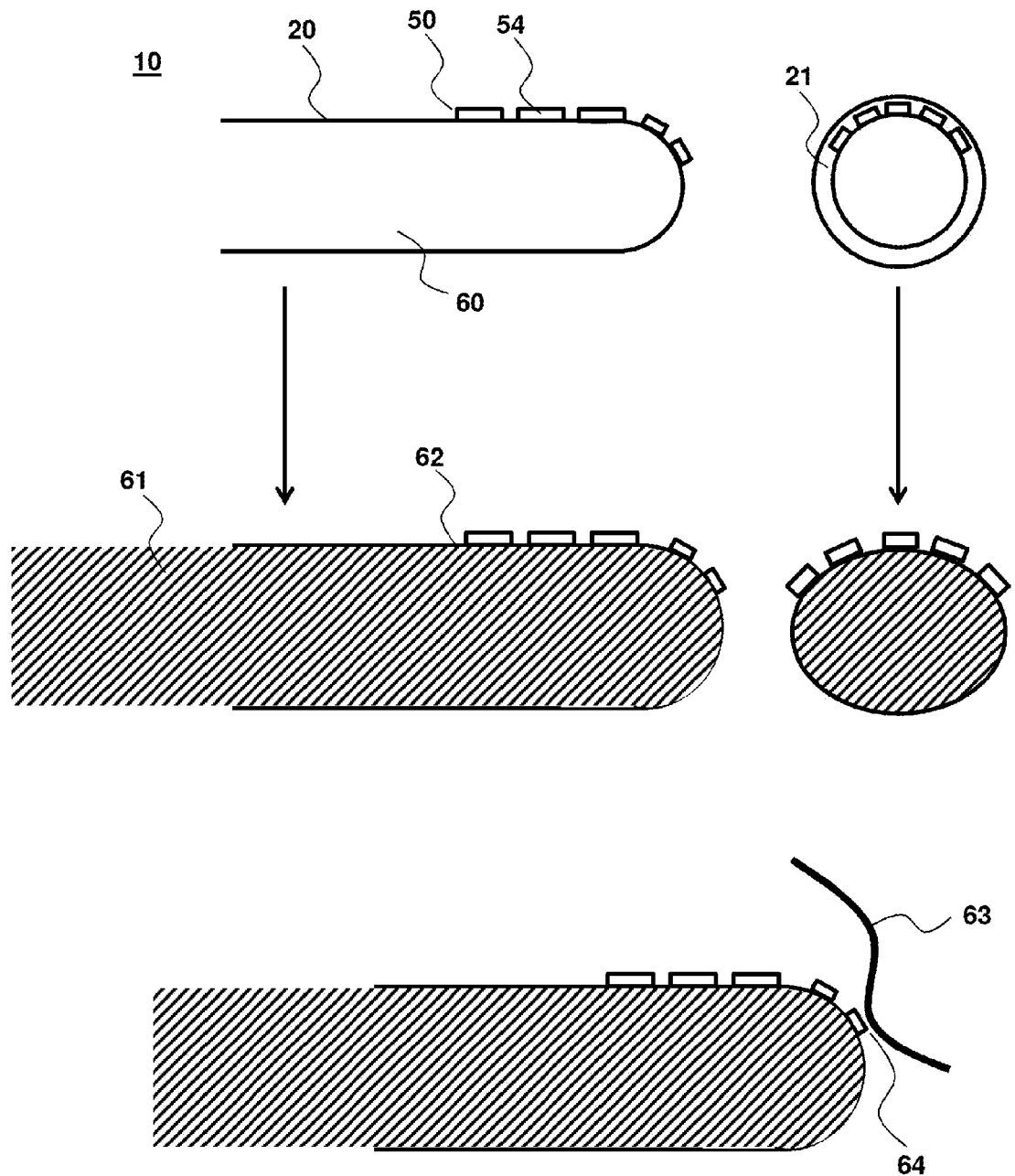
FIG. 15 provides view of an appendage mountable electronic system of the invention accommodating an appendage and interacting with an external surface.

An enclosure 60 is defined by inner surface 30. Referring to FIG. 15, enclosure 60 receives an appendage 61 such that a surface 62 of the appendage is in conformal contact with the inner surface 30 of the substrate 20. FIG. 15 illustrates electronic device 50 on the outer surface 40 that is a system 10 with outer surface supported sensors, such as tactile sensors, for assessing a tactile parameter such as contact force or pressure with external surface 63. Optionally, the substrate 20 may stretch to accommodate the appendage 61 within the enclosure 60. Optionally, the enclosure does not stretch to accommodate an appendage.

Figure 16:
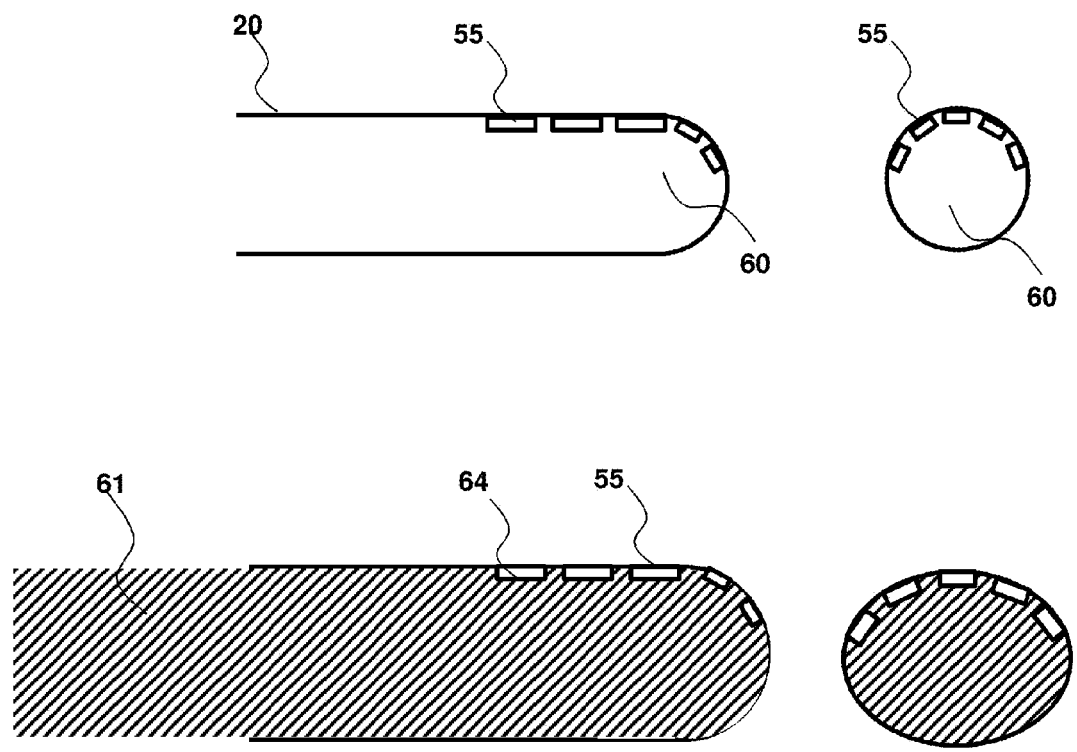
FIG. 16 shows a system having electronic devices supported on the inner surface 30 of the substrate.

For comparison, FIG. 16 shows a system 11 having electronic devices supported on the inner surface 30 of the substrate 20. The electronic devices may be electrotactile stimulators that interface with living tissue of an appendage within the enclosure, or a sensor to measure a parameter of interest of the appendage (e.g., temperature, hydration). The panels on the right side of FIGS. 15-16 indicate an aspect where the shape of the enclosure changes upon receipt of the appendage as illustrated by an end view cross-section of the system 10. As desired, one or more barrier or encapsulation layers 21 may encapsulate at least a portion of the electronic device, such as the sensors and/or actuators, including those supported by the outer surface (illustrated in top right panel of FIG. 15) and/or those by the inner surface.

One useful aspect of outer surface mounted sensors is for interfacing with an external surface 63. For a sensor 54 that is a tactile sensor, the tactile sensor interface provides a measure of the contact force or pressure between the sensor 54 and the external surface 63. For other sensor types, such as temperature, optical, pH or any others disclosed herein, the sensor provides an output corresponding to the functionality of the sensor. This is generally referred to as "external interfacing" or an external interface parameter and is indicated by 64. In contrast, referring to FIG. 16, actuators 55 supported by the inner surface may interface with living tissue of an appendage within the enclosure. This is generally referred to as "internal interfacing" or an internal interface parameter. In an aspect, any of the systems provided herein are for external interfacing (FIG. 15), internal interfacing (16), or both external and internal interfacing (combination of FIGS. 15 and 16, as indicated by the electronic devices in FIG. 14B and C).

Figure 17:
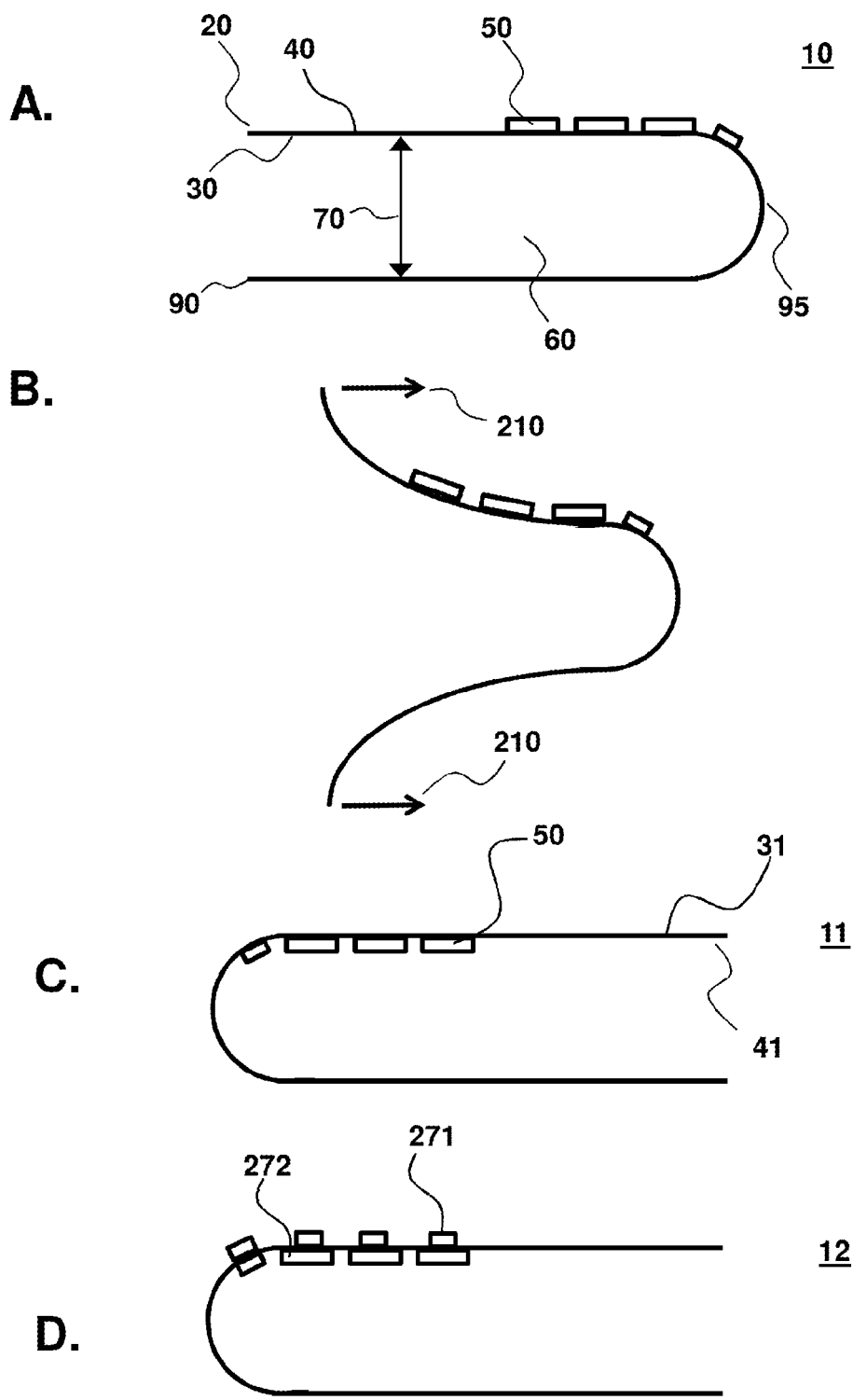
FIG. 17 shows a method for making an appendage mountable electronic system of the invention.

One example of a method for making any of the devices provided herein is schematically illustrated in FIG. 17. FIG. 17A shows an appendage mountable electronic system 10 having an electronic device 50 supported on the substrate 20 outer surface 40 with inner surface 30 defining an enclosure 60. The enclosure 60, may be described by a characteristic dimension such as diameter 70 or length between ends 90 and 95, or volume of 60. In an embodiment, diameter 70 is slightly smaller than the maximum diameter of the object that is being received by the interior portion 60. Such a size difference requires the substrate 20 to stretch to receive the object, thereby ensuring tight conformal contact between the substrate 20, electronic devices 50, and the appendage surface within interior portion enclosure 60 (see, e.g., FIGS. 15-16).

FIG. 17B illustrates application of a substrate surface flipping force 210 that flips outer surface 40 to the inner surface 41 and, correspondingly, inner surface 30 to outer surface 31, as illustrated in FIG. 17C. FIG. 17D indicates that new outer surface may receive another electronic device, such that a first array 271 of devices is supported by the outer surface and a second array 272 of devices is supported by the inner surface, such as to provide a multi-functional system 12.

Figure 18:
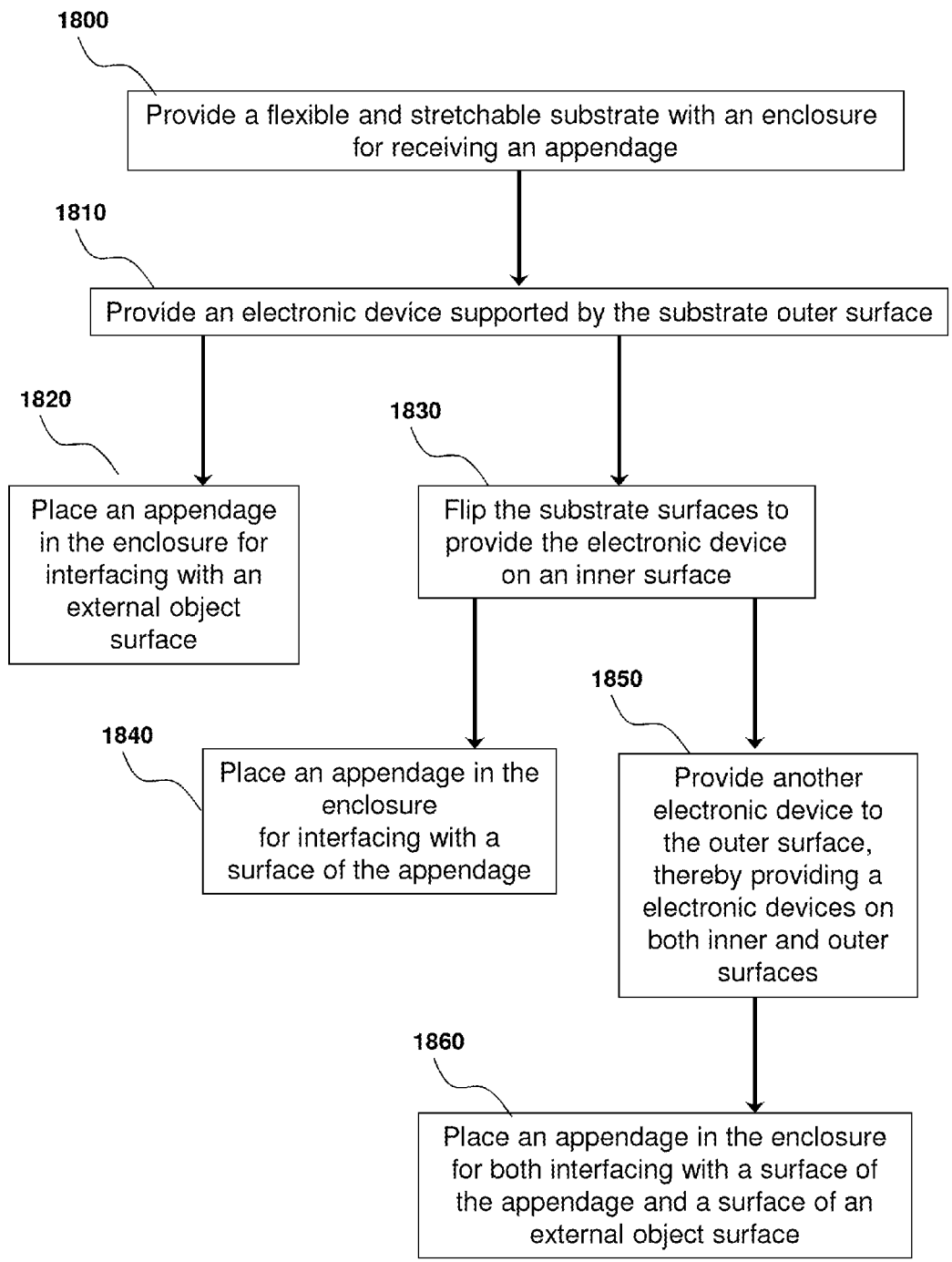
FIG. 18 is a process flow summary of one embodiment for making any of the systems disclosed herein.

FIG. 18 is a process flow summary of one embodiment for making any of the systems disclosed herein. In step 1800 a flexible and stretchable substrate is provided, such as having an enclosure defined by the substrate inner surface. An electronic device is provided to the substrate outer surface 1810. The device may be partially encapsulated by a barrier layer. Depending on the application of interest, an appendage may be placed in the enclosure, as outlined in 1820. This device may then be used to interface with an object that is external to the enclosure, such as for surface sensing applications. Alternatively, if the system is for an application to interface with the appendage, flipping 1830 may be performed, so that the electronic device is on the inner surface. If only interfacing with the appendage is desired, step 1840 is followed. Alternatively, another electronic device may be provided to the outer surface as indicated in 1850, which is optionally at least partially or completely encapsulated with a barrier layer. In this fashion, dual functionality is obtained for external and internal interfacing 1860. In contrast, 1820 is for external interfacing only, and 1840 is for internal interfacing only. As outlined herein, any of the electronic devices are provided to a surface such as by transfer printing of various metallic and semiconductor components, preferably thin components in a layout that can accommodate bending and stretching.

Figure 20:
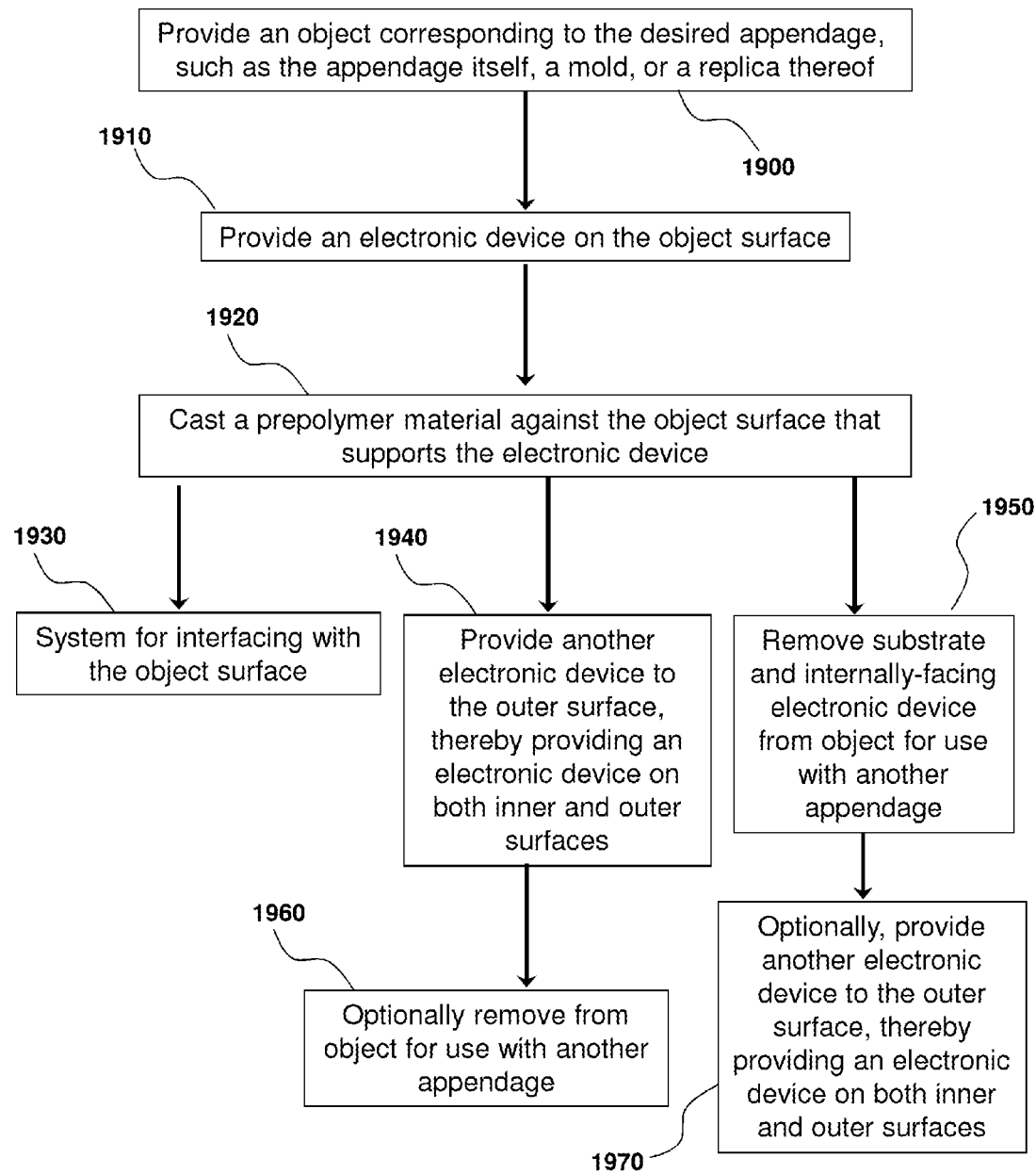
FIG. 20 is a process flow summary of one embodiment for making any of the systems disclosed herein by casting a substrate against an object surface.

FIG. 20 is a process flow summary of another embodiment for making any of the systems disclosed herein by providing an object 1900 that corresponds to the appendage, or model or mold thereof. An electronic device is provided to the surface of the object 1910. A prepolymer or other substrate-precursor is cast against the object surface and the electronic device 1920. Depending on the application of interest, the device is then ready for use 1930 or may receive another electronic device on the outer substrate 1940. As indicated by steps 1950 1960 and 1970, the printing to the external surface can be before or after removal from the object provided in step 1910.

Example 4

Tactile Sensor on External and Internal Surfaces

In another example, any of the systems provided herein has electronic devices on both the inner and outer surfaces, wherein the inner and outer surface devices are in communication with each other such as to functionally provide a pressure or force sensor. In one embodiment, the communication is an electrical communication for a pair of opposed electrodes. Another example of functional communication include direct electrical contact, where output from a device on one surface is provided to a device on the outer surface. In another aspect, the devices are in thermal contact with each other, such as between a heat source and a thermal or temperature sensor.

Figure 19:
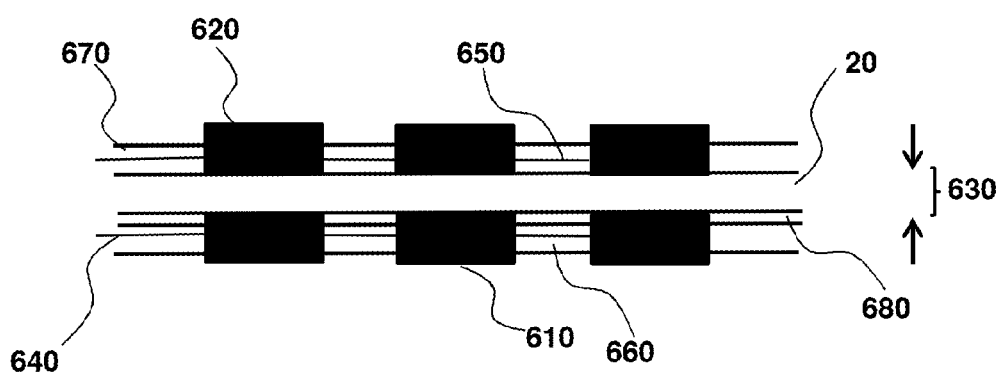
FIG. 19 is a schematic of a capacitance-based tactile sensor on both inner and outer substrate surfaces.

An aspect of the invention is a tactile sensor that provides information about contact forces or pressures based on a change in thickness of a material between two opposed electrodes. Examples include pressure sensors based on capacitance or thermal sensing. Referring to FIG. 19, a first electronic device 610 and a second electronic device 620 are supported by inner and outer surfaces of elastomeric substrate 20. For simplicity, only a portion of a side-view cross-section of the system is illustrated in FIG. 19, with an enclosure volume for conformally contacting an appendage (not shown) adjacent to an array of first electronic device 610. For simplicity, FIG. 19 exemplifies electronic devices that are electrodes 610 and 620. Electrical interconnects 640 (first plurality of electrical interconnects) and 650 (second plurality of electrical interconnects) provide an electrical connection, either independently or in a multiplexed configuration, to each electrode. The interconnects may be in a bent configuration, such as serpentine geometry. The interconnects may be embedded within first and second encapsulation layers 660 670, respectively. Optionally, a barrier layer 680 is used to further electrically isolate the interconnects from each other and/or the surrounding environment. The barrier layer and encapsulation layers positions are determined in part by the desired application. For example, a barrier layer that is a thermal barrier may be positioned between a thermal source/thermal sensor and the appendage/external environment, depending on positions of the sensor and source.

Electronic devices, e.g., thermal sensors/sources or electrodes 610 and 620 may be spatially aligned with respect to each other and separated by elastomeric substrate 20 of a defined thickness 630, thereby functionally forming a capacitor whose capacitance varies with thickness 630. In this manner, a pressure or force sensor is provided that measures pressure or force based on a change in the thickness 630. In this aspect, it is important that substrate 20 be formed of an elastic material that will change thickness in accordance with an applied contact force or pressure. Preferably, the material is elastomeric in that its response characteristics are reversible and will compress and relax back to an uncompressed state with minimal change in resting thickness. Elastomeric materials can help provide more accurate, robust and reliable measure of force or pressure. Force and pressure are generally used interchangeably in that one can be calculated from the other based on the expression F=P/A, where F is the force (Newtons), P is the pressure (Pascals) and A is the area over which the pressure is applied ($m^2$). Functionally, a thermal-based system is similarly arranged, except decrease in thickness results in increase in temperature. Similarly, optical sources and detectors may be employed, where optical transmission is dependent on substrate thickness. In this manner, any of the systems provided herein may include any of the above-referenced pressure sensors for providing tactile information, such as a force applied to or from an external surface, including a pressure that may spatially-vary over the contact area region of the applied force.

There is tolerance with respect to the degree of alignment between the inner 610 and outer electronic devices 620, particularly as the systems are readily calibrated by applying known forces or pressures and observing the resultant change in capacitance (see, e.g., FIG. 6(d)), temperature or optical transmission. In an aspect, the substrate is at least partially translucent or transparent to facilitate alignment during printing of the outer-facing electronic devices to the outer surface with the inner-facing electronic devices.

Use of aligned electrode array pairs provides arrays of capacitors, thereby allowing detection of a force or pressure distribution over the surface of the system by virtue of spatially varying changes in substrate thickness 630 that are detected by the different capacitors.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure. Specific names of compounds are intended to be exemplary, as it is known that one of ordinary skill in the art can name the same compounds differently.

Every formulation or combination of components described or exemplified herein can be used to practice the invention, unless otherwise stated.

Whenever a range is given in the specification, for example, a physical property range, a size range, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The following patents and patent applications are hereby incorporated by reference in their entireties: U.S. Pat. Nos. 7,195,733; 7,622,367; 7,557,367; 7,799,699; 7,943,491; 7,521,292; 8,367,035; 8,217,381; 7,932,123; 7,972,875; 8,198,621; 7,704,684; 7,982,296; 8,039,847; 7,705,280; 2010/0002402; 2010/0052112; 2010/0317132; 2012/0105528; 2012/0157804; 2008/0055581; 2011/0230747; 2011/0187798; 2013/0072775; Ser. No. 13/624,096 (filed Sep. 21, 2012).

We claim:

1. An appendage mountable electronic system, said system comprising:
 a flexible or stretchable substrate having an inner surface and an outer surface, wherein the inner surface defines an enclosure capable of receiving an appendage having a curved surface; and
 a flexible or stretchable electronic device comprising one or more sensors, actuators or both supported by the inner surface or the outer surface of said flexible or stretchable substrate; said sensors, actuators or both comprising one or more inorganic semiconductor components, one or more metallic components, or one or more inorganic semiconductor components and one or more metallic components; wherein at least a portion of said inorganic semiconductor components, metallic components or both has a thickness less than or equal to 500 microns;
 wherein said flexible or stretchable substrate and said electronic device provide a net bending stiffness of the system low enough such that the inner surface of the substrate is capable of establishing conformal contact with a surface of said appendage provided within said enclosure.

2. an appendage mountable electronic system, said system comprising:
  a flexible or stretchable substrate having an inner surface and an outer surface, wherein the inner surface defines an enclosure capable of receiving an appendage having a curved surface; and a flexible or stretchable electronic device comprising one or more sensors, actuators or both supported by the inner surface or the outer surface of said flexible or stretchable substrate; said sensors, actuators or both comprising one or more inorganic semiconductor components, one or more metallic components, or one or more inorganic semiconductor components and one or more metallic components;
  wherein at least a portion of said inorganic semiconductor components, metallic components or both has a thickness less than or equal to 500 microns;
  wherein said flexible or stretchable substrate and said electronic device provide a net bending stiffness of the system low enough such that the inner surface of the substrate is capable of establishing conformal contact with a surface of said appendage provided within said enclosure; wherein said flexible or stretchable substrate and said electronic device provide said net bending stiffness of the system less than or equal to $1\times10^8$ GPa $\mu m^4$, a net flexural rigidity of the system less than or equal to $1\times10^{-4}$ Nm, or a net bending stiffness of the system low enough such that said one or more sensors, actuators or both supported by the inner surface of the substrate are capable of establishing conformal contact with said surface of said appendage provided within said enclosure.

3. The system of claim 2, wherein the instrumented glove is a medical glove for surgery.

4. The system of claim 1 comprising a human-machine interface system, a device for robotic manipulation, or an instrumented glove that is a medical glove for surgery.

5. The system of claim 1, wherein the substrate is a flexible substrate and the electronic device is a flexible electronic device or the substrate is a stretchable substrate and the electronic device is a stretchable electronic device.

6. The system of claim 1, wherein said electronic device comprises 2 to 1000 of said one or more sensors, actuators or both, or at least 3 different types of said one or more sensors, actuators or both.

7. The system of claim 1, wherein said one or more sensors, actuators or both are provided in an open mesh geometry.

8. The system of claim 1, wherein said one or more sensors, actuators or both have a footprint surface area selected from the range of 0.5 cm$^2$ to 100 cm$^2$.

9. The system of claim 1, wherein said electronic device comprises one or more sensors selected from the group consisting of an electrode, a tactile sensor, a strain gauge, a capacitance sensor, a temperature sensor, a pressure sensor, a motion sensor, a position sensor, a displacement sensor, an acceleration sensor, a force sensor, a chemical sensor, a pH sensor, a capacitive sensor, an optical sensor, a photodetector, an imaging system and any arrays and combinations thereof; or one or more actuators selected from the group consisting of an electrotactile stimulator, an electrode, a heat source, a piezoelectric element, an acoustic element, a source of RF energy, a magnetic actuator, a source of electromagnetic radiation, a laser, a light emitting diode and arrays and any arrays and combinations thereof.

10. The system of claim 1, wherein at least a portion of said sensors, actuators or both are supported by said inner surface of said flexible or stretchable substrate and at least a portion of said sensors, actuators or both are supported by said outer surface of said flexible or stretchable substrate.

11. The system of claim 1, wherein said flexible or stretchable electronic device comprises a plurality of said electro-tactile stimulators provided in an array and supported by said inner surface, outer surface, or both inner and outer surfaces of said substrate for electrically stimulating said appendage in the enclosure.

12. The system of claim 11, wherein said flexible or stretchable electronic device comprises a multiplexed array of said electro-tactile stimulators, wherein said electro-tactile stimulators of said array are electrically interconnected via a network of serpentine electrical interconnects.

13. The system of claim 11, wherein each of said electro-tactile stimulators comprise a thin film metal structure having an inner region surrounded by an outer region, wherein a gap is provided between said inner region and said outer region, wherein said inner region has lateral dimensions selected from the range of 10 μm to 1000 μm, said outer ring has lateral dimensions selected from the range of 10 μm to 5000 μm, and said gap has lateral dimensions selected from the range of 10 μm to 1000 μm.

14. The system of claim 13, wherein each of said inner region is a conductive disk-shaped electrode and said outer region is a conductive ring-shaped electrode positioned concentric with said disk-shaped electrode.

15. The system of claim 11, wherein each of said electro-tactile sensors comprise a thin film metal structure having lateral dimensions selected from the range of 100 μm to 5000 μm.

16. The system of claim 1, wherein said electronic device comprises one or more tactile sensors supported by the outer surface and one or more electro-tactile stimulators supported by said inner surface, wherein said one or more tactile sensors are in electrical communication with said one or more electrotactile stimulators such that an output from the one or more tactile sensors is provided to the one or more electrotactile stimulators to electrically stimulate said appendage in proportion to the tactile sensor output.

17. The system of claim 1, wherein said electronic device comprises a plurality of electrodes, each electrode comprising:
  an inner disk having a diameter that is less than 1 mm; and
  an outer ring that surround the inner disk, wherein the inner disk and outer ring are concentrically positioned relative to each other, with a separation distance between the inner disk and outer ring selected from a range that is greater than or equal to 100 μm and less than or equal to 500 μm.

18. The system of claim 1, comprising said one or more inorganic semiconductor components, wherein each of said one or more inorganic semiconductor components independently comprises a polycrystalline semiconductor material, a single crystalline semiconductor material or a doped polycrystalline or single crystalline semiconductor material, each of said one or more inorganic semiconductor components independently has a thickness that is less than or equal to 100 μm.

19. The device of claim 18, wherein each of said inorganic semiconductor components of the electronic device has a net flexural rigidity less than or equal to $1\times10^{-4}$ Nm, a Young's modulus selected from the range of 0.5 MPa to 10 GPa, a net bending stiffness less than or equal to $1\times10^8$ GPa μm$^4$, or independently comprises a semiconductor nanomembrane structure.

20. The system of claim 1, comprising said one or more metallic components, wherein said one or more metallic conductor components comprise a plurality of electrodes provided in an array and each of said electrodes in said array independently has a thickness less than or equal to 100 μm.

21. The system of claim 20, wherein the stretchable or flexible electrode array comprises a plurality of electrode unit cells, wherein adjacent electrode unit cells of the electrode array are separated from each other by a distance less than or equal to 50 μm.

22. The system of claim 21, wherein each electrode unit cell of the electrode array comprises a contact pad, amplifier and multiplexer, wherein the contact pad provides an electrical interface to the tissue and is in electrical communication with the amplifier and multiplexer.

23. The system of claim 20, wherein said one or more metallic conductor components further comprise a plurality of stretchable electrical interconnects, wherein said stretchable electrical interconnects electrically connect rigid device islands comprising at least a portion of said one or more one or more inorganic semiconductor components, one or more metallic components, or one or more inorganic semiconductor components and one or more metallic components.

24. The system of claim 23, wherein said rigid device islands comprise the one or more sensors, actuators or both, wherein said sensors or actuators are selected from the group consisting of: an electrode, a tactile sensor, a strain gauge, a capacitance sensor, a temperature sensor, a pressure sensor, a motion sensor, a position sensor, a displacement sensor, an acceleration sensor, a force sensor, a chemical sensor, a pH sensor, a capacitive sensor, an optical sensor, a photodetector, an imaging system, an electrotactile stimulator, an electrode, a heat source, a piezoelectric element, an acoustic element, a source of RF energy, a magnetic actuator, a source of electromagnetic radiation, a laser, a light emitting diode and arrays and any arrays and combinations thereof.

25. The system of claim 1, wherein the inner surface and outer surface are interchangeably flippable without substantial degradation of a functionality parameter of the one or more sensors, actuators or both supported by the inner surface or the outer surface of said flexible or stretchable substrate and an outer surface that supports the electronic device is flipped, so that after flipping the functional electronic device supported by the outer surface is the functional electronic device supported by the inner surface.

26. The system of claim 1, wherein said flexible or stretchable substrate is characterized by a fracture strain greater than or equal to 500%.

27. The system of claim 1, further comprising a barrier layer at least partially encapsulating at least a portion of said functional device, wherein said barrier layer limits a net leakage current from the electronic device to an amount which does not adversely affect a material in contact with said system, limits a heat transfer from the electronic device to an amount which does not adversely affect a material in contact with said system, or substantially prevents passage of an external fluid to at least a portion of said electronic device.

28. The system of claim 1, further comprising one or more stretchable interconnects that electrically connect at least a portion of said one or more sensors, actuators or both, wherein the one or more stretchable interconnects comprises a nanowire in a serpentine configuration, the nanowire having a rectangular cross-section, with a thickness selected from the range of 50 nm to 1 μm and a width that is selected from the range of 10 μm to 1 mm, the serpentine configuration characterized by an average radius of curvature selected from the range of 100 μm to 10 mm.

29. The system of claim 1, wherein a first electronic device is supported by the inner surface and a second electronic device is supported by the second surface; wherein the first and second electronic devices are spatially aligned and in communication with respect to each other, wherein the communication is characterized by a parameter that varies with a substrate thickness between the first and second electronic devices, thereby forming a pressure sensor.

30. The system of claim 1, wherein the enclosure has a receiving dimension that is smaller than a corresponding dimension of the appendage, wherein during use a strain in the flexible or stretchable substrate increases the receiving dimension to accommodate the appendage within enclosure without adversely impacting the flexible or stretchable electronic device, wherein the strain generates a contact force between the flexible or stretchable substrate and the appendage within the enclosure to establish and maintain intimate and conformal contact between the flexible or stretchable electronic device supported by the substrate inner surface and the curved surface of the appendage.

31. The system of claim 1, wherein said flexible or stretchable substrate and said electronic device provide said net bending stiffness of the system less than or equal to $1 \times 10^8$ GPa μm$^4$.

32. The system of claim 1, wherein said flexible or stretchable substrate and said electronic device provide a net flexural rigidity of the system less than or equal to $1 \times 10^{-4}$ Nm.

33. The system of claim 1, wherein said flexible or stretchable substrate and said electronic device provide a net bending stiffness of the system low enough such that said one or more sensors, actuators or both supported by the inner surface of the substrate are capable of establishing conformal contact with said surface of said appendage provided within said enclosure.

34. An appendage mountable electronic system, said system comprising:
an elastomeric substrate having an inner surface and an outer surface, wherein the inner surface defines an enclosure capable of receiving an appendage having a curved surface, and the elastomeric substrate has a resting thickness that is less than 10 mm;
a first electronic device supported by the inner surface;
a second electronic device supported by the outer substrate, wherein the first and second electronic devices are in an opposed configuration with respect to each other and separated by a thickness of the elastomeric substrate to form a pressure sensor whose output varies as a function of elastomeric substrate thickness;
each of the first and second electronic devices comprises one or more inorganic semiconductor components, one or more metallic components, or one or more inorganic semiconductor components and one or more metallic components, having a thickness less than 1 mm and a lateral dimension less than 5 mm.

* * * * *

UNITED STATES PATENT AND TRADEMARK OFFICE
CERTIFICATE OF CORRECTION

PATENT NO. : 9,554,484 B2
APPLICATION NO. : 13/853770
DATED : January 24, 2017
INVENTOR(S) : Rogers et al.

Page 1 of 1

It is certified that error appears in the above-identified patent and that said Letters Patent is hereby corrected as shown below:

Claim 1 should read:
1. An appendage mountable electronic system, said system comprising:
a flexible or stretchable substrate having an inner surface and an outer surface, wherein the inner surface defines an enclosure capable of receiving an appendage having a curved surface; and
a flexible or stretchable electronic device comprising one or more sensors, actuators or both supported by the inner surface or the outer surface of said flexible or stretchable substrate; said sensors, actuators or both comprising one or more inorganic semiconductor components, one or more metallic components, or one or more inorganic semiconductor components and one or more metallic components; wherein at least a portion of said inorganic semiconductor components, metallic components or both has a thickness less than or equal to 500 microns;
wherein said flexible or stretchable substrate and said electronic device provide a net bending stiffness of the system low enough such that the inner surface of the substrate is capable of establishing conformal contact with a surface of said appendage provided within said enclosure;
wherein said flexible or stretchable substrate and said electronic device provide said net bending stiffness of the system less than or equal to $1 \times 10^8$ GPa $\mu m^4$, a net flexural rigidity of the system less than or equal to $1 \times 10^{-4}$ Nm, or a net bending stiffness of the system low enough such that said one or more sensors, actuators or both supported by the inner surface of the substrate are capable of establishing conformal contact with said surface of said appendage provided within said enclosure.

Please replace the existing Claim 2 with:
2. The system of claim 1 comprising an instrumented glove for covering a hand or an instrumented finger-tube for covering a finger or finger-tip.

In Claim 11, the phrase "plurality of said electro-tactile stimulators" should read, --plurality of electro-tactile stimulators--, and the phrase "for electrically stimulating said appendage in the enclosure" should be deleted.

Signed and Sealed this
Sixteenth Day of May, 2017

Michelle K. Lee
*Director of the United States Patent and Trademark Office*